(12) United States Patent
Koeberl et al.

(10) Patent No.: US 9,873,868 B2
(45) Date of Patent: Jan. 23, 2018

(54) CONSTRUCTS FOR EXPRESSING LYSOSOMAL POLYPEPTIDES

(75) Inventors: Dwight D. Koeberl, Durham, NC (US); Baodong Sun, Morrisville, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 13/403,783

(22) Filed: Feb. 23, 2012

(65) Prior Publication Data

US 2012/0276072 A1 Nov. 1, 2012

Related U.S. Application Data

(63) Continuation of application No. 10/761,530, filed on Jan. 21, 2004, now abandoned.

(60) Provisional application No. 60/441,789, filed on Jan. 22, 2003.

(51) Int. Cl.

| A01N 63/00 | (2006.01) |
|---|---|
| C12N 9/24 | (2006.01) |
| C12N 1/20 | (2006.01) |
| C12N 1/00 | (2006.01) |
| C12N 15/00 | (2006.01) |
| C12P 21/06 | (2006.01) |
| C12P 19/34 | (2006.01) |
| C07H 21/04 | (2006.01) |
| C07K 1/00 | (2006.01) |
| A61K 48/00 | (2006.01) |
| C12N 9/26 | (2006.01) |

(52) U.S. Cl.
CPC ........ C12N 9/2408 (2013.01); C07K 2319/02 (2013.01); C07K 2319/036 (2013.01)

(58) Field of Classification Search
CPC .......... C07K 2319/02; C07K 2319/036; C12N 9/2408
USPC ..... 424/93.21, 93.2; 435/200, 252.3, 254.11, 435/320.1, 69.1, 91.1; 536/23.1, 23.2, 536/23.4; 530/350; 514/44 R
See application file for complete search history.

(56) References Cited

U.S. PATENT DOCUMENTS

| 4,407,956 A | 10/1983 | Howell et al. |
|---|---|---|
| 4,501,729 A | 2/1985 | Boucher et al. |
| 4,644,056 A | 2/1987 | Kothe et al. |
| 5,139,941 A | 8/1992 | Muzyczka et al. |
| 5,283,184 A | 2/1994 | Jorgensen et al. |
| 5,298,400 A | 3/1994 | Whitfeld et al. |
| 5,339,346 A | 8/1994 | White et al. |
| 5,482,852 A | 1/1996 | Yoder et al. |
| 5,521,070 A | 5/1996 | Meulien |
| 5,589,377 A | 12/1996 | Lebkowski et al. |
| 5,658,785 A | 8/1997 | Johnson et al. |
| 5,712,136 A | 1/1998 | Thomas et al. |
| 5,770,442 A | 6/1998 | Thomas et al. |
| 5,837,484 A | 11/1998 | Trempe et al. |
| 5,858,775 A | 1/1999 | Johnson et al. |
| 5,871,982 A | 2/1999 | Wilson et al. |
| 5,882,877 A | 3/1999 | Gregory et al. |
| 5,922,315 A | 7/1999 | Soumitra et al. |
| 5,962,313 A * | 10/1999 | Podsakoff et al. ......... 435/320.1 |
| 6,110,456 A | 8/2000 | During et al. |
| 6,118,045 A | 9/2000 | Reuser et al. |
| 6,146,874 A | 11/2000 | Zolotukhin et al. |
| 6,251,677 B1 | 6/2001 | Wilson et al. |
| 6,268,487 B1 | 7/2001 | Kutzko et al. |
| 6,328,958 B1 | 12/2001 | Amalfitano et al. |
| 6,387,368 B1 | 5/2002 | Wilson et al. |
| 6,410,049 B1 | 6/2002 | Papahadjopoulos et al. |
| 6,582,692 B1 | 6/2003 | Podsakoff et al. |
| 6,812,339 B1 * | 11/2004 | Venter et al. .............. 536/24.31 |
| 6,858,425 B1 | 2/2005 | Heus |
| 7,056,712 B2 | 6/2006 | Chen |

(Continued)

FOREIGN PATENT DOCUMENTS

| EP | 0043075 | 1/1982 |
|---|---|---|
| EP | 0693554 | 1/1996 |

(Continued)

OTHER PUBLICATIONS

Amalfitano et al., Systemic correction of the muscle disorder glycogen storage disease type II after hepatic targeting of a modified adenovirus vector encoding human acid-a-glucosidae. Proc. Natl. Acad. Sci., 1999, vol. 96: 8861-8866.*
Devos et al., Practical limits of function prediction. Proteins: Structure, Function, and Genetics. 2000, vol. 41: 98-107.*
Sun et al, "Enhanced Efficacy of an AAV Vector Encoding Chimeric, Highly Secreted Acid α-Glucosidase in Glycogen Storage Disease Type II", Molecular Therapy 14(6):822-830 (2006).
Xia et al, "The HIV Tat protein transduction domain improves the biodistribution of β-glucouronidase expressed from recombinant viral vectors", Nature Biotechnology 19:640-644 (2001).
Orii et al, "Defining the Pathway for Tat-mediated Delivery of β-Glucuronidase in Cultured Cells and MPS VII Mice", Molecular Therapy 12(2):345-352 (2005).

(Continued)

*Primary Examiner* — Ganapathirama Raghu
(74) *Attorney, Agent, or Firm* — McDonnell Boehnen Hulbert & Berghoff LLP

(57) ABSTRACT

Provided are isolated nucleic acids for expressing lysosomal polypeptides such as lysosomal acid α-glucosidase (GAA) and vectors comprising the same. The invention provides an isolated nucleic acid encoding a chimeric polypeptide comprising a secretory signal sequence operably linked to a lysosomal polypeptide. The invention also provides an isolated nucleic acid comprising a coding region encoding a GAA and a GAA 3' untranslated region (UTR), wherein the GAA 3' UTR comprises a deletion therein. The invention further provides an isolated nucleic acid comprising a coding region encoding a GAA and a 3' UTR wherein the 3' UTR is less than about 200 nucleotides in length and comprises a segment that is heterologous to the GAA coding region. Also provided are methods of making and using delivery vectors encoding lysosomal polypeptides to produce the lysosomal polypeptide to treat subjects afflicted with a deficiency in the lysosomal polypeptide.

11 Claims, 20 Drawing Sheets

(56) References Cited

U.S. PATENT DOCUMENTS

| | | | |
|---|---|---|---|
| 7,071,172 | B2 | 7/2006 | McCown et al. |
| 7,351,410 | B2 | 4/2008 | Van Bree et al. |
| 7,396,811 | B2 | 7/2008 | LeBowitz et al. |
| 7,858,367 | B2 | 12/2010 | Amalfitano et al. |
| 2003/0219414 | A1 | 11/2003 | Podsakoff et al. |
| 2003/0228284 | A1 | 12/2003 | McCown et al. |
| 2004/0081645 | A1 | 4/2004 | Van Bree et al. |
| 2005/0123531 | A1 | 6/2005 | Chen |
| 2008/0175833 | A1 | 7/2008 | Chen |

FOREIGN PATENT DOCUMENTS

| | | |
|---|---|---|
| JP | S 6447381 | 2/1989 |
| WO | WO1991006309 | 5/1991 |
| WO | WO1996017947 | 6/1996 |
| WO | WO 98/11206 A | 3/1998 |
| WO | WO1998027207 | 6/1998 |
| WO | WO2000012740 | 3/2000 |
| WO | WO 00/34451 | 6/2000 |
| WO | WO 0047741 A1 | 8/2000 |
| WO | WO 02/988466 A1 | 12/2002 |
| WO | WO2002098466 | 12/2002 |
| WO | WO 03/092594 | 11/2003 |
| WO | WO 03093295 A2 | 11/2003 |
| WO | WO 03093295 A3 | 11/2003 |
| WO | WO 2005/003296 A2 | 1/2005 |

OTHER PUBLICATIONS

Poenaru, L., Approach to Gene Therapy of Glycogenosis Type II (Pompe Disease), Molecular Genetics and Metabolism, 70 (3):163-169 (2000).
Hirschhorn, R., "Glycogen Storage Disease Type II: Acid .alpha.-Glucosidase (Acid Maltase) Deficiency", The Metabolic and Molecular Bases of Inherited Disease, (77) 11:2443-2464 (1995).
Barton, N.W., et al., "Therapeutic response to intravenous infusions of glucocerebrosidase in a patient with Gaucher disease", Proc. Natl. Acad. Sci, 87:1913-1916 (Mar. 1990).
Lauer, R.M., "Administration of a Mixture of Fungal Glucosidases to a Patient with Type II Glycogenosis (Pompe's Disease)", Pediatrics, 42:672-676 (1968).
Van den Hout, et al., "Enzyme therapy for Pompe disease with recombinant human .alpha.-glucosidase from rabbit milk", J. Inherit. Metab. Dis., 24:266-274 (2001).
Williams, J.C., et al., "Enzyme Replacement in Pompe Disease With an .alpha.-Glucosidase-Low Density Lipoprotein Complex", Birth Defects: Original Article Series, 16 (1):415-423 (1980).
Yang, H.W., et al., "Recombinant Human Acid .alpha.-Glucosidase Corrects Acid .alpha.-Glucosidase-Deficient Human Fibroblasts, Quail Fibroblasts, and Quail Myoblasts", Pediatric Research, 43 (3):374-380 (1998).
Amalfitano, A., et al., "Recombinant human acid .alpha.-glucosidase enzyme therapy for infantile glycogen storage disease type II: Results of a phase I/II clinical trial", Genetics in Medicine, 3 (2):132-138 (2001).
Ausems, M., et al., "Frequency of glycogen storage disease type II in The Netherlands: implications for diagnosis and genetic counselling", European Journal of Human Genetics, 7:713-716 (1999).
Bijvoet, A.G.A., et al., "Recombinant human acid .alpha.,-glucosidase: high level production in mouse milk, biochemical characteristics, correction of enzyme deficiency in GSDII KO mice", Human Molecular Genetics, 7 (11):1815-1824 (1998).
Bijvoet, A.G.A., et al., "Human acid .alpha.-glucosidase from rabbit milk has therapeutic effect in mice with glycogen storage disease type II", Human Molecular Genetics, 8 (12):2145-2153 (1999).
Brooks, D.A., "Immune Response to Enzyme Replacement Therapy in Lysosomal Storage Disorder Patients and Animal Models", Molecular Genetics and Metabolism, 68:268-275 (1999).
de Barsy, T., et al., "Enzyme Replacement in Pompe Disease: An Attempt with Purified Human Acid .alpha.-Glucosidase", Birth Defects:Original Article Series, 9 (2):184-190 (1973).

Fuller, M., et al., "Isolation and characterisation of a recombinant, precursor form of lysosomal acid .alpha.-glucosidase", Eur. J. Biochem, 234:903-909 (1995).
Hermans, M.M.P., et al., "The effect of a single base pair deletion (.DELTA.T525) and a C1634T missense mutation (pro545leu) on the expression of lysosomal .alpha.-glucosidase in patients with glycogen storage disease type II", Human Molecular Genetics, 3 (12):2213-2218 (1994).
Hermans, M.M.P., et al., "The conservative substitution Asp-645. fwdarw.Glu in lysosomal .alpha.-glucosidase affects transport and phosphorylation of the enzyme in an adult patient with glycogen-storage disease type II", Biochem. J., 289:687-693 (1993).
Hermans, M.M.P., et al., "Identification of a Point Mutation in the Human Lysosomal .alpha.-Glucosidase Gene Causing Infantile Glycogenosis Type II", Biochemical and Biophysical Research Communications, 179 (2):919-926 (1991).
Hoefsloot, L.H., et al., "Characterization of the human lysosomal .alpha.-glucosidase gene", Biochem. J., 272:493-497 (1990).
Hug, G., et al., "Treatment Related Observations in Solid Tissues, Fibroblast Cultures and Amniotic Fluid Cells of Type II Glycogenosis, Hurler Disease and Metachromatice Leukodystrophy", Birth Defects: Original Articles Series, 9 (2):160-183 (1973).
Kikuchi, T., et al., "Clinical and Metabolic Correction of Pompe Disease by Enzyme Therapy in Acid Maltase-deficient Quail", J. Clin. Invest., 101 (4):827-833 (1998).
Martiniuk, F., et al., "Recombinant Human Acid .alpha.-Glucosidase Generated in Bacteria: Antigenic, but Enzymatically Inactive", DNA and Cell Biology, 11 (9):701-706 (1992).
Reuser, A.J.J., et al., "Biochemical, Immunological, and Cell Genetic Studies in Glycogenosis Type II", Am J Hum Genet, 30:132-143 (1978).
Slonim, A.E., et al., "Improvement of muscle function in acid maltase deficiency by high-protein therapy", Neurology, 33:34-38 (1983).
Van der Ploeg, A.T., et al., "Intravenous Administration of Phosphorylated Acid .alpha.-Glucosidase Leads to Uptake of Enzyme in Heart and Skeletal Muscle of Mice", J. Clin. Invest., 87:513-518 (1991).
Wu, J-Y., et al., "Expression of Catalytically Active Human Multifunctional Glycogen-Debranching Enzyme and Lysosomal Acid Alpha-Glucosidase in Insect Cells", Biochemistry and Molecular Biology International, 39 (4):755-764 (1996).
Watson, J.G., et al., "Bone Marrow Transplantation for Glycogen Storage Disease Type II (Pompe's Disease)", N. Engl. J. Med., 314:385 (1986).
Martiniuk, F., et al., "Carrier Frequency for Glycogen Storage Disease Type II in New York and Estimates of Affected Individuals Born With the Disease", American Journal of Medical Genetics, 76:69-72 (1998).
Schiffmann, R., et al., "Infusion of .alpha.-galactosidase A reduces tissue globotriaosylceramide storage in patients with Fabry disease", Proc. Natl. Acad. Sci., 97 (1):365-370 (2000).
Van Hove, J.L.K, et al., "High-level production of recombinant human lysosomal acid .alpha.-glucosidase in Chinese hamster ovary cells which targets to heart muscle and corrects glycogen accumulation in fibroblasts from patients with Pompe disease", Proc. Natl. Acad. Sci., 93:65-70 (1996).
Lei, K.J., et al., "Genetic Basis of Glycogen Storage Disease Type 1a: Prevalent Mutations at the Glucose-6-Phosphatase Locus", Am. J. Hum. Gen., 57 (4):766-771 (1995).
Pauly, D.F., et al., "Complete correction of acid .alpha.-glucosidase deficiency in Pompe disease fibroblasts in vitro, and lysosomally targeted expression in neonatal rat cardic and skeletal muscle", Gene Therapy, 5 (4):473-480 (1998).
Chen, Y-T, et al., "Towards a molecular therapy for glycogen storage disease type II (Pompe disease)", Mol. Medicine Today, 6 (6):245-251 (2000).
Kakkis, E., et al., "Recombinant .alpha.-L-iduronidase replacement therapy in mucopolysaccharidosis 1: Results of a human clinical trial", Am. J. Hum. Genet., 63 (4):A25 (1998).

(56) References Cited

OTHER PUBLICATIONS

Byrne, B.J., et al., "Reconstitution of Acid .alpha.-glucosidase activity in a mouse model of cardioskeleton myopathy, Pompe's Disease", Circulation, vol. 98 (17):I737 (1998).
Elliger et al, "Enhanced Secretion and Uptake of β-Glucuronidase Improves Adeno-associated Viral-Mediated Gene Therapy of Mucopolysaccharidosis Type VII Mice", Molecular Therapy 5(5):617-626 (2002).
Synpac Press Release (Jun. 30, 1999) Duke University starts clinical trials for Pompe's disease.
Press Release (Apr. 19, 2000) Genezyme General Obtains Rights to Pompe Disease Therapy from Synpac.
Van den Hout et al, "Recombinant human α-glucosidase from rabbit milk in Pompe patients", The Lancet 356:397-398 (2000).
Ding et al, "Long-Term Efficacy after [E1, polymerase] Adenovirus-Mediated Transfer of Human Acid-α-Glucosidase Gene into Glycogen Storage Disease Type II Knockout Mice", Human Gene Therapy 12:955-965 (2001).
Barash et al, "Human secretory signal peptide description by hidden Markov model and generation of a strong artificial signal peptide for secreted protein expression", Biochemical and Biophysical Research Communication 294:835-842 (2002).
Chen, U.S. Appl. No. 11/889,457, filed Aug. 13, 2007.
Chen et al, Protein Expression and Purification 20:472-484 (2000).
Broun et al, "Catalytic plasticity of fatty acid modification enzymes underlying chemical diversity of plant lipids", Science 282:1315-1317 (1998).
Witkowski et al, "Conversion of b-ketoacyl synthase to a malonyl decarboxylase by replacement of the active-sitecysteine with glutamate", Biochemistry 38:11643-11650 (1999).
Seffernick et al, "Melamine deaminase and atrazine chlorophydrolase: 98 percent identical but functionally different", J. Bacteriol, 183(8):2405-2410 (2001).
Whisstock et al, "Prediction of protein function from protein sequence and structure", Q Rev. Biophys. 36(3):307-340 (2003).
Hoefsloot et al, "Primary structure and processing of lysosomal α-glucosidase; homology with the intestinal sucrase-isomaltase complex", EMBO 7(6):1697-1704 (1988).
Haberman et al, "Attenuation of seizures and neuronal death by adeno-associated virus vector galanin expression and secretion", Nature Medicine 9:1076-1080 (2003).
Haberman et al, "Regulated Suppression of Focal Seizure Sensitivity by Adeno-Associated Virus (AAV) Vector-Dependent Galanin Secretion", Abstract, Program No. 619.10, Washington, DC: Society for Neuroscience (2002).
International Search Report issued in connection with PCT/US2004/001453.
Barash et al, "Human secretory signal peptide description by hidden Markov model and generation of a strong artificial signal peptide for secreted protein expression", Biochemical and Biophysical Research Communications 294:835-842 (2002).
Cheng et al, "Gene therapy progress and prospects: gene therapy of lysomal storage disorders", Gene Therapy 10:1275-1281 (2003).
Fraites et al, Correction of the enzymatic and functional deficits in a model of pompe disease using adeno-associated virus vectors, Molecular Therapy 5 5:571-578 (2002).
Hirschhorn et al, "Glycogen Storage disease type II: acid α-glucosidase (acid maltase) deficiency", Wonsiewicz M, Noujaim S, Boyle P, eds., The Metabolic and Molecular Bases of Inherited Disease, 8th Edition, New York: McGraw Hill; pp. 3389-3420 (2001).
Koeberl et al, "Development of a hybrid adenovirus/adeno-associated virus for gene therapy in glycogen storage disease type II", Abstract presented at the Annual Meeting of the Pediatric Academic Societies; Seattle, WA (May 3-6, 2003).
Lin et al, "Adeno-associated virus-mediated transfer of human acid maltase gene results in a transient reduction of glycogen accumulation in muscle of Japanese quail with acid maltase deficiency", Gene Therapy 9:554-563 (2002).

Martin-Touaux et al, "Muscle as a putative producer of acid αglucosidase for glycogenosis type II gene therapy", Human Molecular Genetics 11(14):1637-1645 (2002).
Raben et al, "Enzyme replacement therapy in the mouse model of Pompe disease", Molecular Genetics and Metabolism 80:159-169 (2003).
Sun et al, "Correction of glycogen storage disease type II (GSD II) by intramuscular administration of an adeno-associated virus (AAV) vector pseudot7ped as AAV6", Abstrct presented at the 6th Annual Meeting of the American Society for Gene Therapy; Washington, D.C. (Jun. 4-8, 2003).
Sun et al,"Long-term correction of glycogen storage disease type II with a hybrid Ad-AAV vector", Molecular Therapy 7(2):193-201 (2003).
Sun et al, "Packaging of an AAV vector encoding human acid α-glucosidase for gene therapy in glycogen storage disease type II with a modified hybrid adenovirus-AAV vector", Molecular Therapy 7(4):467-477 (2003).
Wisselaar et al, "Structural and functional changes of lysomal acid αglucosidase during intracellular transport maturation", Journal of Biological Chemistry 268(3):2223-2231 (1993).
Guo et al., "Evaluation of promoter strength for hepatic gene expression in vivo following adenovirus-mediated gene transfer", Gene Ther., 3(9):802-10. (Sep. 1996).
Gorodetsky et al., "Isolation and characterization of the Bos taurus beta-casein gene", 66(1):87-96., (Jun. 1988).
Halbert et al., "Adeno-associated virus type 6 (AAV6) vectors mediate efficient transduction of airway epithelial cells in mouse lungs compared to that of AAV2 vectors", 75(14):6615-24. (Jul. 2001).
Haj-Ahmad et al., "Development of a helper-independent human adenovirus vector and its use in the transfer of the herpes simplex virus thymidine kinase gene", J Virol., 57(1):267-74. (Jan. 1986).
Hall et al., "Organization and sequence of the human alpha-lactalbumin gene", Biochem J., 242(3):735-42. (Mar. 1987).
He et al., "A simplified system for generating recombinant adenoviruses", Proc Natl Acad Sci USA, 95(5):2509-14. (Mar. 1998).
Hermonat et al., "Use of adeno-associated virus as a mammalian DNA cloning vector: transduction of neomycin resistance into mammalian tissue culture cells", Proc Natl Acad Sci USA, 81(20):6466-70. (Oct. 1984).
Herzog et al., "Stable gene transfer and expression of human blood coagulation factor IX after intramuscular injection of recombinant adeno-associated virus", Proc Natl Acad Sci USA, 94(11):5804-9. (May 1997).
Herzog et al., "Long-term correction of canine hemophilia B by gene transfer of blood coagulation factor IX mediated by adeno-associated viral vector", Nat Med., 5(1):56-63. (Jan. 1999).
Higgins et al., "Fast and sensitive multiple sequence alignments on a microcomputer", Comput Appl Biosci., 5 (2):151-3. (Apr. 1989).
Hodges et al., "Adenovirus vectors with the 100K gene deleted and their potential for multiple gene therapy applications", J Viral., 75(13):5913-20. (Jul. 2001).
Hodges et al., "Multiply deleted [E1, polymerase-, and pTP-] adenovirus vector persists despite deletion of the preterminal protein", J Gene Med., 2(4):250-9. (Jul. 2000).
Hohn et al., "Cauliflower Mosaic Virus: A potential vector for plant genetic engineering", Molecular Biology of Plant Tumors, 549-560 (1982).
Horsch et al., "Inheritance of functional foreign genes in plants", Science, 223(4635):496-8. (Feb. 1984).
Inoue et al., "Packaging cells based on inducible gene amplification for the production of adeno-associated virus vectors", J Virol., 72(9):7024-31. (Sep. 1998).
Ivanov et al., "Molecular cloning of bovine beta-lactoglobulin cDNA", Biol Chem Hoppe-Seyler, 369(6):425-9. (Jun. 1988).
Jamieson et al., "Cloning and nucleotide sequence of the bovine beta-lactoglobulin gene", Gene, 61(1):85-90. (1987).
Jones et al., "The rat casein multigene family. Fine structure and evolution of the beta-casein gene", JBC, 260(11) 7042-50. (Jun. 1985).

(56) References Cited

OTHER PUBLICATIONS

Karlin et al., "Applications and statistics for multiple high-scoring segments in molecular sequences", Proc Natl Acad Sci USA, 90(15):5873-7. (Jun. 1993).
Kaufman et al. "Translational efficiency of polycistronic mRNAs and their utilization to express heterologous genes in mammalian cells", EMBO J, 6(1):187-193. (Jan. 1987).
Kessler et al., "Gene delivery to skeletal muscle results in sustained expression and systemic delivery of a therapeutic protein", Proc Natl Acad Sci USA, 93(24):14082-7. (Nov. 1996).
Klein et al., "High-velocity microprojectiles for delivering nucleic acids into living cells", Nature, 327:70-73. (1987).
Koeberl et al., "Persistent, therapeutically relevant levels of human granulocyte colony-stimulating factor in mice after systemic delivery of adeno-associated virus vectors", Hum Gene Ther., 10(13):2133-40. (Sep. 1999).
Kunita et al., "Molecular cloning of acid alpha-glucosidase cDNA of Japanese quail (Coturnix coturnix japonica) and be lack of its mRNA in acid maltase deficient quails", Biochimi Biophys Acta., 1362(2-3):269-78. (Dec. 1997).
Kurjan et al., "Structure of a yeast pheromone gene (MF alpha): a putative alpha-factor precursor contains four tandem copies of mature alpha-factor", Cell, 30(3):933-43. (Oct. 1982).
Leiber et al., "Recombinant adenoviruses with large deletions generated by Cre-mediated excision exhibit different biological properties compared with first-generation vectors in vitro and in vivo", J Viral., 70(12):8944-60. (Dec. 1996).
Loeffler et al., "Gene transfer into primary and established mammalian cell lines with lipopolyamine-coated DNA", Methods in Enzyology, 217:599-618. (1993).
Luckow et al., "High level expression of nonfused foreign genes with Autographa califomica nuclear polyhedrosis virus expression vector", Virology, 170(1):31-9. (May 1989).
Martinuik et al., "Sequence of the cDNA and 5'-flanking region for human acid alpha-glucosidase, detection of an intron in the 5' untranslated leader sequence, definition of 18-bp polymorphisms, and differences with previous cDNA and amino acid sequences", DNA Cell Biol., 9(2):85-94. (Mar. 1990).
McLaughlin et al., "Adeno-associated virus general transduction vectors: analysis of proviral structures", J Virol., 62(6):1963-73. (Jun. 1988).
Mercier et al., "Structure and function of milk protein genes", J. Dairy Sci., 76(10):3079-98. (Oct. 1993).
Miller, "Progress toward human gene therapy", Blood, 76(2):271-8. (Jul. 1990).
Muzyczka., "Use of adeno-associated virus as a general transduction vector for mammalian cells", Curr Top Microbiol Immunol, 158:97-129. (1992).
Nakai et al., "Adeno-associated viral vector-mediated gene transfer of human blood coagulation factor IX into mouse liver", Blood, 91(12):4600-7. (Jun. 1995).
Needleman et al., "A general method applicable to the search for similarities in the amino acid sequence of two proteins", J Mol Biol, 48(3):443-53. (Mar. 1970).
Paszkowski et al., "Direct gene transfer to plants", EMBO J, 3(12):2717-22. (1984).
Pearson et al., "Improved tools for biological sequence comparison", Proc Natl Acad Sci USA, 85(8)2444-8. (Apr. 1988).
Raben et al., "Targeted disruption of the acid alpha-glucosidase gene in mice causes an illness with critical features of both infantile and adult human glycogen storage disease type II", JBC, 273(30):19086-92. (Jul. 1998).
Raebum et al., "Techniques for drug delivery to the airways, and the assessment of lung function in animal models", J Pharmacol toxicol methods, 27(3):143-59. (May 1992).
Rabinowitz et al., "Cross-packaging of a single adeno-associated virus (AAV) type 2 vector genome into multiple AAV serotypes enables transduction with broad specificity" J Viral., 76(2)191-801. (Jan. 2002).

Reeves et al., "Posttranslational gene regulation and specific binding of the nonhistone protein HMG-I by the 3' untranslated region of bovine interleukin 2 cDNA", Proc Natl Acad Sci USA 84(18):6531-35. (Sep. 1987).
Remy et al., "Gene transfer with a series of lipophilic DNA-binding molecules", Bioconjug Chem., 5(6):647-54. (Nov. 1994).
Richards et al., "Construction and Preliminary Characterization of the rat casein and alpha-lactalbumin cDNA clones", J. Biol. Chem, 256(1):526-332. (Jan. 1981).
Rosenfeld et al., "Adenovirus-mediated transfer of a recombinant alpha 1-antitrypsin gene to the lung epithelium in vivo", Science, 252(5004):431-4. (Apr. 1991).
Rosenfeld et al., "In vivo transfer of the human cystic fibrosis transmembrane conductance regulator gene to the airway epithelium", Cell, 68(1):143-55. (Jan. 1992).
Rutledge et al., "Infectious clones and vectors derived from adeno-associated virus (AAV) serotypes other than AAV type 2", J Viral., 72(1):309-19. (Jan. 1998).
Samulski et al., "Helper-free stocks of recombinant adeno-associated viruses: normal integration does not require viral gene expression", J Virol., 63(9):3822-8. (Sep. 1989).
Sang, "Transgenic chickens—methods and potential applications", Trends Biotechnol., 12(10):415-20. (Oct. 1994).
Seed, "An LFA-3 cDNA encodes a phospholipid-linked membrane protein homologous to its receptor CD2", Nature, 329(6142):840-2. (Oct. 1987).
Schwartz et al., "Distinct RNA sequences in the gag region of human immunodeficiency virus type 1 decrease RNA stability and inhibit expression in the absence of Rev protein", J Virol, 66(1):150-9. (Jan. 1992).
Schwartz et al., "Mutational inactivation of an inhibitory sequence in human immunodeficiency virus type 1 results in Rev-independent gag expression", J Virol., 66(12):7176-82. (Dec. 1992).
Schultz et al., "Expression and secretion in yeast of a 400-kDa envelope glycoprotein derived from Epstein-Barr virus", Gene, 54(1):113-23. (1987).
Shaw et al., "A conserved AU sequence from the 3' untranslated region of GM-CSF mRNA mediates selective mRNA Degradation", Cell, 46(5):659-67. (Aug. 1986).
Smith & Waterman, "Comparison of Biosequences", Adv. Appl. Math 2:482-9. (1981).
Smith et al., "Production of human beta interferon in insect cells infected with a baculovirus expression vector", Mol Cell Biol., 3(12):2156-65. (Dec. 1983).
Soulier et al., "Expression analysis of ruminant alpha-lactalbumin in transgenic mice: developmental regulation and general location of important cis-regulatory elements", FEBS Lett., 297(1-2):13-8. (Feb. 1992).
Snyder et al., "Correction of hemophilia B in canine and murine models using recombinant adeno-associated viral vectors", Nat Med., 5(1):64-70. (Jan. 1999).
Snyder et al., "Persistent and therapeutic concentrations of human factor IX in mice after hepatic gene transfer of recombinant AAV vectors", Nat Genet., 16(3):270-6. (Jul. 1997).
Stewart et al., "Nucleotide sequences of bovine alpha S1- and kappa-casein cDNAs", Nucleic Acids Res., 12 (9):3895-907. (May 1984).
Thierry et al., "Systemic gene therapy: biodistribution and long-term expression of a transgene in mice", Proc Natl Acad Sci USA, 92(21):9742-6. (Oct. 1995).
Tratschin et al., "Genetic analysis of adeno-associated virus: properties of deletion mutants constructed in vitro and evidence for an adeno-associated virus replication function", J Virol., 51(3):611-9. (Sep. 1984).
Tratschin et al., "A human parvovirus, adeno-associated virus, as a eucaryotic vector transient expression and encapsidation of the procaryotic gene for chloramphenicol acetyltransferase", Mol Cell Biol., 4(10):2072-81. (Oct. 1984).
Tsujino et al., "Adenovirus-mediated transfer of human acid maltase gene reduces glycogen accumulation in skeletal muscle of Japanese quail with acid maltase deficiency", Hum Gene Ther., 9(11):1609-16. (Jul. 1998).

(56) References Cited

OTHER PUBLICATIONS

Wang et al., "Persistent transgene expression in mouse liver following in vivo gene transfer with a delta E1/delta E4 adenovirus vector", Gene Ther., 4(5):393-400. (May 1997).
Whitbeck et al., "Glycoprotein D of herpes simplex virus (HSV) binds directly to HVEM, a member of the tumor necrosis factor receptor superfamily and a mediator of HSV entry", J Viral., 71(8):6083-93. (Aug. 1997).
Wolff et al., "Direct gene transfer into mouse muscle in vivo", Science, 247(4949 Pt 1):1465-8. (Mar. 1990).
Wondisford et al., "Cloning of the human thyrotropin beta-subunit gene and transient expression of biologically active human thyrotropin after gene transfection", Mol. Endocrinol., 2(1):32-39. (Jan. 1988).
Van der Ploeg et al., "Intravenous administration of phosphorylated acid alpha-glucosidase leads to uptake of enzyme in heart and skeletal muscle of mice", J Clin Invest., 87(2):513-8. (Feb. 1991).
Vilotte et al., "Complete nucleotide sequence of bovine alpha-lactalbumin gene: comparison with its rat counterpart", Biochimie., 69(6-7):609-20. (Jun. 1987).
Yu-Lee et al., "The rat casein multigene family. I. Fine structure of the gamma-casein gene", JBC, 258(17):10794-804. (Sep. 1983).
Zhu et al., "Systemic gene expression after intravenous DNA delivery into adult mice", Science, 261(5118):209-11 . (Jul. 1993).
Zolotukhin et al., "Recombinant adeno-associated virus purification using novel methods improves infectious titer and yield", Gene Ther., 6(6):973-85. (Jun. 1999).
GenBank Accession No. NM_000477 "*Homo sapiens* albumin (ALB), mRNA," published on Jul. 24, 2017 [retrieved on Aug. 29, 2017] [retrieved from the internet ncbi.nlm.nih.gov/nuccore/NM_000477] [6 pages].
GenBank Accession No. NM_000152 "*Homo sapiens* glucosidase alpha, acid (GAA), transcript variant 1, mRNA," published on Jul. 2, 2017 [retrieved on Aug. 29, 2017] [retrieved from the internet ncbi.nlm.nih.gov/nuccore/NM_000152] [3 pages].
GenBank Accession No. NM_008064 "Mus musculus glucosidase, alpha, acid (Gaa), transcript variant 1, mRNA," published on Aug. 27, 2017 [retrieved on Aug. 29, 2017] [retrieved from the internet ncbi.nlm.nih.gov/nuccore/NM_008064] [3 pages].
NCBI Accession No. NC_002067 "Human adenovirus D, complete genome," published on Jul. 1, 2008 [retrieved on Aug. 29, 2017] [retrieved from the internet ncbi.nlm.nih.gov/nuccore/NC_002067.1?report=genbank] [11 pages].
GenBank Accession No. M73260 "Mastadenovirus h5 gene, complete genome," published on Apr. 8, 1996 [retrieved on Aug. 29, 2017] [retrieved from the internet ncbi.nlm.nih.gov/nuccore/M73260] [7 pages].
GenBank Accession No. X73487 "Adenovirus type 12 DNA, complete genome," published on Oct. 23, 2008 [retrieved on Aug. 29, 2017] [retrieved from the internet ncbi.nlm.nih.gov/nuccore/X73487] [12 pages].
GenBank Accession No. AF108105 "Human adenovirus type 17 complete genome," published on Mar. 15, 1999 [retrieved on Aug. 29, 2017] [retrieved from the internet ncbi.nlm.nih.gov/nuccore/AF108105] [7 pages].
GenBank Accession No. L19443 "Human adenovirus F, complete genome," published on Apr. 27, 2012 [retrieved on Aug. 29, 2017] [retrieved from the internet ncbi.nlm.nih.gov/nuccore/L19443] [7 pages].
GenBank Accession No. NC_003466 "Andes virus segment S, complete sequence," published on Oct. 20, 2015 [retrieved on Aug. 29, 2017] [retrieved from the internet ncbi.nlm.nih.gov/nuccore/NC_003466] [2 pages].
NCBI Accession No. NC_001405 "Human adenovirus C, complete genome," published on Mar. 10, 2011 [retrieved on Aug. 29, 2017] [retrieved from the internet ncbi.nlm.nih.gov/nuccore/NC_001405] [17 pages].

NCBI Accession No. NC_001460 "Human adenovirus A, complete genome," published on Apr. 24, 2012 [retrieved on Aug. 29, 2017] [retrieved from the internet ncbi.nlm.nih.gov/nuccore/NC_001460] [15 pages].
Amalfitano et al., "Isolation and characterization of packaging cell lines that coexpress the adenovirus E1, DNA polymerase, and preterminal proteins: implications for gene therapy", Gene Ther. 4(3):258-63. (Mar. 1997).
Sun et al., "Immunomodulatory gene therapy prevents antibody formation and lethal hypersensitivity reactions in murine pompe disease", Mol Ther. 18(2):353-60. (Feb. 2010).
Wang et al., "Sustained correction of bleeding disorder in hemophilia B mice by gene therapy", Proc Natl Acad Sci USA 96(7):3906-10. (Mar. 1999).
Mizuno et al., "Basic research for interferon gene therapy against malignant glioma", No Shinkei Geka 20(5):547-51. (May 1992) [English abstract submitted].
Davey, "Recent Developments in the Culture and Regeneration of Plant Protoplasts", Protoplasts, pp. 19-29. (1983).
Dale, "Protoplast Culture and Plant Regeneration of Cereals and Other Recalcitrant Crops", Protoplasts, pp. 31-41 . (1983).
Allen et al., "Improved adeno-associated virus vector production with transfection of a single helper adenovirus gene, E4orf6", Mol Ther., 1(1):88-95. (Jan. 2000).
Allen et al., "Identification and elimination of replication-competent adeno-associated virus (AAV) that can arise by nonhomologous recombination during AAV vector production", J. Virol., 71(9):6816-22. (Sep. 1997).
Altschul et al., "Basic local alignment search tool", J. Mol Biol., 215(3):403-10. (Oct. 1990).
Altschul et al., "Local alignment statistics", Methods Enzymol., 266:460-80. (1996).
Altschul et al., "Gapped BLAST and PSI-BLAST: a new generation of protein database search programs", Nucleic Acids Res., 25(17):3389-402. (Sep. 1997).
Alexander et al., "Isolation and characterization of the bovine kappa-casein gene", Eur J Biochem., 178(2):395-401. (Dec. 1988).
Alexander et al., "Complete sequence of the bovine beta-lactoglobulin cDNA", Nucleic Acid Res., 17(16):6739. (Aug. 1989).
Amalfitano et al., "Systemic correction of the muscle disorder glycogen storage disease type II after hepatic targeting of a modified adenovirus vector encoding human acid-alpha-glucosidase", Proc Natl Acad Sci USA, 96(16):8861-6. (Aug. 1999).
Amalfitano et al., "Production and characterization of improved adenovirus vectors with the E1, E2b, and E3 genes deleted", J Viral., 72(2):926-33. (Feb. 1998).
Armentano et al., "Effect of the E4 region on the persistence of transgene expression from adenovirus vector", J Viral., 71(3):2408-16. (Mar. 1997).
Baldari et al., "A novel leader peptide which allows efficient secretion of a fragment of human interleukin 1 beta in *Saccharomyces* cerevisiae", EMBO J., 6(1):229-34. (Jan. 1987).
Behr, "Gene transfer with synthetic catonic amphiphiles: prospects for gene therapy", Bioconjug Chem., 5(5):382-9. (Sep. 1994).
Bergelson et al., "Isolation of a common receptor for Coxsackie B viruses and adenoviruses 2 and 5", Science, 275 (5304):1320-3. (Feb. 1997).
Berkner, "Development of adenovirus vectors for the expresssion of heterologous genes," Biotechniques, 6(7):616-29. (Jul. 1988).
Binding, "Regeneration of Plants", Plant Protoplasts, pp. 21-37. (1985).
Blaese et al., "Vectors in cancer therapy: how will they deliver?" Cancer Gene Therapy, 2(4):291-7. (Dec. 1995).
Brigham et al., "In vivo transfection of murine lungs with a functioning prokaryotic gene using a liposome vehicle", Am J Med Sci., 298(4):278-81. (Oct. 1989).
Brignon et al., "Complete Amino acid sequene of bovine alphaS2-casein", FEBS Lett., 76(2):274-279. (Apr. 1977).
Brinster et al., "Introns increase transcriptional efficiency in transgenic mice", PNAS, 85(3):836-40. (Feb. 1988).

(56) References Cited

OTHER PUBLICATIONS

Campbell et al., "Comparison of the whey acidic protein genes of the rat and mouse", Nucleic Acids Res., 12 (22):8685-97. (Nov. 1984).

Chao et al., "Several log increase in therapeutic transgene delivery by distinct adeno-associated viral serotype vectors", Mol Ther., 2(6):619-23. (Dec. 2000).

Clark et al., "Expression of Human anti-hemophilic factor IX in the milk of transgenic sheep", BioTechnology 7:487-92 (1989).

Crystal., "Transfer of genes to humans: early lessons and obstacles to success", Science, 270(5235):404-10. (Oct. 1995).

Daly et al., "Neonatal gene transfer leads to widespread correction of pathology in a murine model of lysosomal storage disease", Proc Natl Acad Sci USA, 96(5):2296-300. (Mar. 1999).

Daly et al., "Neonatal intramuscular injection with recombinant adeno-associated virus results in prolonged beta-glucuronidase expression in situ and correction of liver pathology in mucopolysaccharidosis type VII mice", Hum Gene Ther., 10(1):85-94. (Jan. 1999).

Devereux et al., "A comprehensive set of sequence analysis programs for the VAX", Nucleic Acids Res., 12(1 pt 1):387-95. (Jan. 1984).

Ding et al., "Efficacy of gene therapy for prototypical lysosomal storage disease (GSD-II) is critically dependent on vector dose, transgene promoter, and the tissues targeted for vector transduction", Mol Ther., 5(4):436-46. (Apr. 2002).

DiTullio et al., "Production of cycstic fibrosis transmembrane conductance regulator in the milk of transgenic mice", Biotechnology(N.Y), 10(11:74-7. (Jan. 1992).

Douglas et al., "Targeted gene delivery by tropism-modified adenoviral vectors", Nat Biotechnol., 14(11):1574-8. (Nov. 1996).

Felgner et al., "Enhanced gene delivery and mechanism studies with a novel series of cationic lipid formation", JBC, 269(4)2550-61. (Jan. 1994).

Felgner et al., "Cationic liposome-mediated transfection", Nature, 337(6205):387-8. (Jan. 1989).

Felgner et al., "Lipofection: a highly efficient, lipid-mediated DNA-transfection procedure", Proc Natl Acad Sci USA, 84 (21):7413-7. (Nov. 1987).

Feng et al., "Progressive sequence alignment as a prerequisite to correct phylogenetic trees", J Mol Evol., 25 (4):351-60. (1987).

Flotte et al., "Gene expression from adeno-associated virus vectors in airway epithelial cells", Am J Respir Cell Mol Biol., 7(3)349-56. (Sep. 1992).

Flotte et al., "Expression of the cystic fibrosis transmembrane conductance regulator from a novel adeno-associated virus promoter", JBC, 268(5):3781-90. (Feb. 1993).

Fraley et al., "Expression of bacterial genes in plant cells", PNAS, 80(15):4803-7. (Aug. 1983).

Fromm et al., "Expression of genes transferred into monocot and dicot plant cells by electroporation", Proc Natl Acad Sci USA, 82(17):5824-8. (Sep. 1985).

Gao et al., "Cationic liposome-mediated gene transfer", Gene Ther., 2(10):710-22. (Dec. 1995).

Gao et al., "Biology of adenovirus vectors with E1 and E4 deletions for liver-directed gene therapy", J Virol., 70 (12):8934-43. (Dec. 1996).

Gao et al., "High-titer adeno-associated viral vectors from Rep/Cap cell line and hybrid shuttle virus", Hum Gene Ther., 9(16):2353-62. (Nov. 1998).

Gondo et al., "Aerosols for delivery of therapeutic and diagnostic agents to the respiratory tract", Crit Rev Ther Drug Carrier Syst., 6(4):273-313. (1990).

Gordon et al., "Production of human tissue plasminogen activator in transgenic mouse milk", Nat Biotechnology, 5:1183-1187. (1987).

* cited by examiner

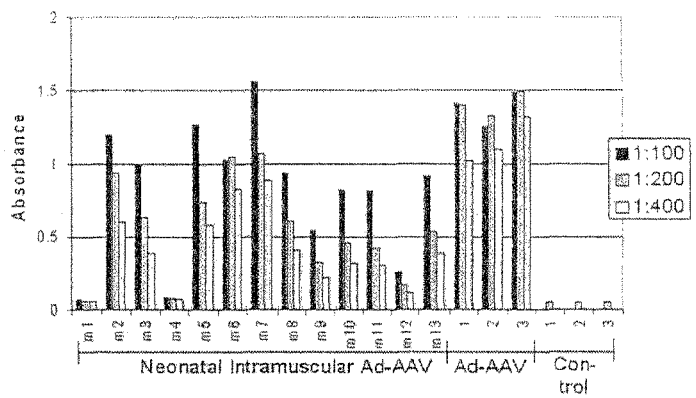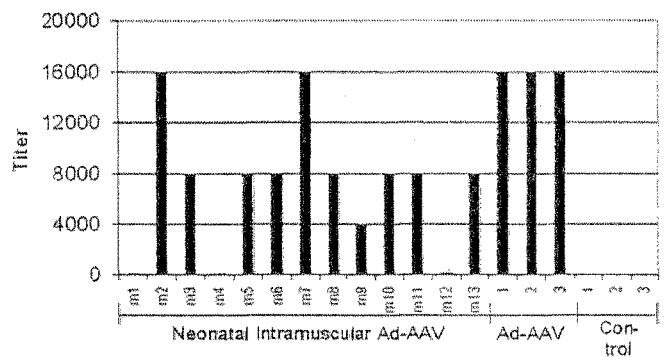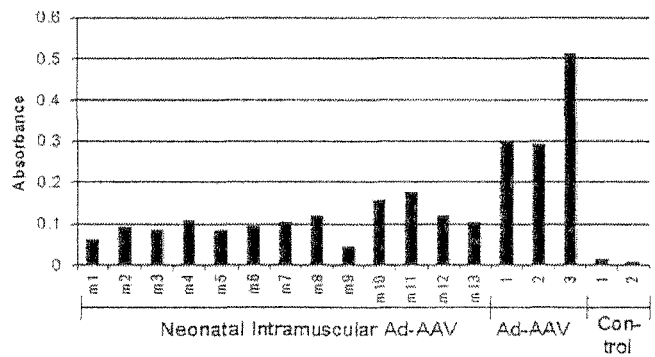
*FIG. 3*

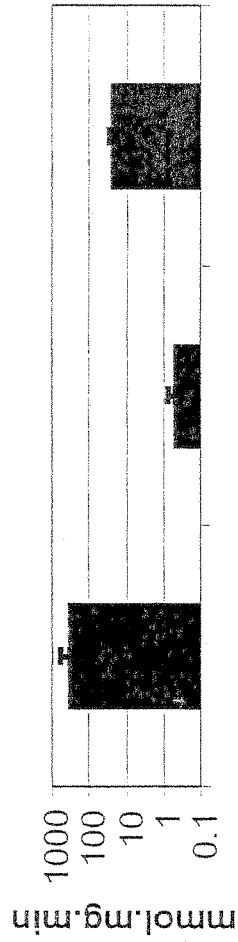 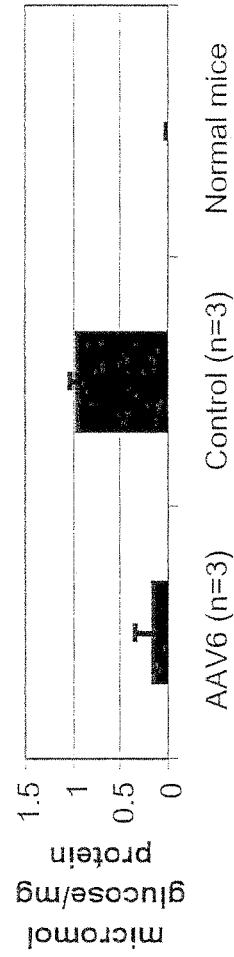
FIG. 6

FIG. 8A

The full-length human GAA cDNA sequence (3846 bp, Genebank number: NM_000152).

```
   1 gcgcctgcgc gggaggccgc gtcacgtgac ccaccgcggc cccgcccgc gacgagctcc
  61 cgccggtcac gtgacccgcc tctgcgcgcc cccgggcacg acccggagt ctccgcgggc
 121 ggccagggcg cgcgtgcgcg gaggtgagcc gggccggggc tgcggggctt ccctgagcgc
 181 gggccgggtc ggtggggcgg tcggctgccc gcgccggcct ctcagttggg aaagctgagg
 241 ttgtcgccgg ggccgcgggt ggaggtcggg gatgaggcag caggtaggac agtgacctcg
 301 gtgacgcgaa ggaccccggc cacctctagg ttctcctcgt ccgcccgttg ttcagcgagg
 361 gaggctctgg gcctgccgca gctgacgggg aaactgaggc acggagcggg cctgtaggag
 421 ctg tccaggc catctccaac catgggagtg aggcaccgc cctgctccca ccggctcctg
 481 gccgtctgcg ccctcgtgtc cttggcaacc gctgcactcc tggggcacat cctactccat
 541 gatttcctgc tggttcccg agagctgagt ggctcctccc cagtcctgga ggagactcac
 601 ccagctcacc agcagggagc cagcagacca gggccccggg atgcccaggc acacccggc
 661 cgtcccagag cagtgcccac acagtgcgac gtccccccca acagccgctt cgattgcgcc
 721 cctgacaagg ccatcaccca ggaacagtgc gaggccgcg gctgctgcta catccctgca
 781 aagcagggc tgcagggagc ccagatgggg cagccctggt gcttcttccc acccagctac
 841 cccagctaca agctgagaa cctgagctcc tctgaaatgg gctacacggc caccctgacc
 901 cgtaccaccc ccaccttctt ccccaaggac atcctgaccc tgcggctgga cgtgatgatg
 961 gagactgaga accgcctcca cttcacgatc aaagatccag ctaacaggcg ctacgaggtg
1021 cccttggaga ccccgcgtgt ccacagccgg gcaccgtccc cactctacag cgtggagttc
1081 tccgaggagc ccttcggggt gatcgtgcac cggcagctgg acggccgcgt gctgctgaac
1141 acgacggtgg cgcccctgtt ctttgcggac cagttcctc agctgccac ctcgctgccc
1201 tcgcagtata tcacaggcct cgccgagcac ctcagtcccc tgatgctcag caccagctgg
1261 accaggatca ccctgtggaa ccgggacctt gcccacgc ccggtgcgaa cctctacggg
1321 tctcacccctt tctacctggc gctggaggac ggcgggtcgg cacacggggt gttcctgcta
1381 aacagcaatg ccatggatgt ggtcctgcag ccgagccctg cccttagctg gaggtcgaca
1441 ggtgggatcc tggatgtcta catcttcctg ggcccagagc ccaagagcgt ggtgcagcag
1501 tacctggacg ttgtgggata cccgttcatg ccgccatact ggggcctggg cttccacctg
1561 tgccgctggg gctactcctc caccgctatc accgccagg tggtggagaa catgaccagg
1621 gcccacttcc cctggacgt ccaatggaac gacctggact acatggactc ccggagggac
1681 ttcacgttca acaaggatgg cttccgggac ttcccggcca tggtgcagga gctgcaccag
1741 ggcggccggc gctacatgat gatcgtggat cctgccatca gcagctcggg ccctgccggg
1801 agctacaggc cctacgacga gggtctgcgg agggggcttt tcatcaccaa cgagaccggc
1861 cagccgctga ttgggaaggt atggcccggg tccactgcct tccccgactt caccaacccc
1921 acagccctgg cctggtggga ggacatggtg gctgagttcc atgaccaggt gcccttcgac
1981 ggcatgtgga ttgacatgaa cgagccttcc aacttcatca gaggctctga ggacggctgc
2041 cccaacaatg agctggagaa cccaccctac gtgcctgggg tggttgggg gaccctccag
2101 gcggccacca tctgtgcctc cagccaccag tttctctcca cacactacaa cctgcacaac
2161 ctctacggcc tgaccgaagc catcgcctcc cacagggcgc tggtgaaggc tcgggggaca
2221 cgcccatttg tgatctcccg ctcgaccttt gctggccacg gccgatacgc cggccactgg
2281 acggggacg tgtggagctc ctgggagcag ctcgcctcct ccgtgccaga aatcctgcag
```

FIG. 8B

```
2341 tttaacctgc tgggggtgcc tctggtcggg gccgacgtct gcggcttcct gggcaacacc
2401 tcagaggagc tgtgtgtgcg ctggacccag ctgggggcct tctaccccct catgcggaac
2461 cacaacagcc tgctcagtct gccccaggag ccgtacagct tcagcgagcc ggcccagcag
2521 gccatgagga aggccctcac cctgcgctac gcactcctcc cccacctcta cacactgttc
2581 caccaggccc acgtcgcggg ggagaccgtg gcccggcccc tcttcctgga gttccccaag
2641 gactctagca cctggactgt ggaccaccag ctcctgtggg gggaggccct gctcatcacc
2701 ccagtgctcc aggccgggaa ggccgaagtg actggctact tccccttggg cacatggtac
2761 gacctgcaga cggtgccaat agaggccctt ggcagcctcc cacccccacc tgcagctccc
2821 cgtgagccag ccatccacag cgaggggcag tgggtgacgc tgccggcccc cctggacacc
2881 atcaacgtcc acctccgggc tgggtacatc atccccctgc agggccctgg cctcacaacc
2941 acagagtccc gccagcagcc catggccctg gctgtggccc tgaccaaggg tggagaggcc
3001 cgaggggagc tgttctggga cgatggagag agcctggaag tgctggagcg aggggcctac
3061 acacaggtca tcttcctggc caggaataac acgatcgtga atgagctggt acgtgtgacc
3121 agtgagggag ctggcctgca gctgcagaag gtgactgtcc tgggcgtggc cacggcgccc
3181 cagcaggtcc tctccaacgg tgtccctgtc tccaacttca cctacagccc cgacaccaag
3241 gtcctggaca tctgtgtctc gctgttgatg ggagagcagt ttctcgtcag ctggtgttag
3301 ccgggcggag tgtgttagtc tctccagagg gaggctggtt ccccagggaa gcagagcctg
3361 tgtgcgggca gcagctgtgt gcgggcctgg gggttg catg tgtcacctgg agctgggcac
3421 taaccattcc aagccgccgc atcgcttgtt tccacctcct gggccggggc tctggccccc
3481 aacgtgtcta ggagagcttt ctccctagat cgcactgtgg gccggggcct ggagggctgc
3541 tctgtgttaa taagattgta aggtttgccc tcctcacctg ttgccggcat gcgggtagta
3601 ttagccacce ccctccatct gttcccagca ccggagaagg gggtgctcag gtggaggtgt
3661 ggggtatgca cctgagctcc tgcttcgcgc ctgctgctct gccccaacgc gaccgcttcc
3721 cggctgccca gagggctgga tgcctgccgg tccccgagca agcctgggaa ctcaggaaaa
3781 ttcacaggac ttgggagatt ctaaatc tta agtgcaatta ttttaataaa aggggcattt
3841 ggaatc
```

FIG. 9A

5' and 3' deleted GAA

```
   1 .................................................... 409  410 g cctgtaggag
 421 ctg tccaggc catctccaac catgggagtg aggcacccgc cctgctccca ccggctcctg
 481 gccgtctgcg ccctcgtgtc cttggcaacc gctgcactcc tggggcacat cctactccat
 541 gatttcctgc tggttccccg agagctgagt ggctcctccc cagtcctgga ggagactcac
 601 ccagctcacc agcagggagc cagcagacca gggcccgggg atgcccaggc acacccggc
 661 cgtcccagag cagtgcccac acagtgcgac gtcccccca acagccgctt cgattgcgcc
 721 cctgacaagg ccatcaccca ggaacagtgc gaggcccgcg gctgctgcta catccctgca
 781 aagcaggggc tgcagggagc ccagatgggg cagccctggt gcttcttccc acccagctac
 841 cccagctaca agctggagaa cctgagctcc tctgaaatgg gctacacggc cacccctgacc
 901 cgtaccaccc ccaccttctt ccccaaggac atcctgaccc tgcggctgga cgtgatgatg
 961 gagactgaga accgcctcca cttcacgatc aaagatccag ctaacaggcg ctacgaggtg
1021 cccttggaga ccccgcgtgt ccacagccgg gcaccgtccc cactctacag cgtggagttc
1081 tccgaggagc ccttcgggt gatcgtgcac cggcagctgg acggccgcgt gctgctgaac
1141 acgacggtgg cgccctgtt ctttgcggac cagttcctc agctgtccac ctcgctgccc
1201 tgcagtata tcacaggcct cgccgagcac ctcagtcccc tgatgctcag caccagctgg
1261 accaggatca ccctgtggaa ccgggacctt gcgcccacgc ccggtgcgaa cctctacggg
1321 tctcaccctt tctacctggc gctggaggac ggcgggtcgg cacacggggt gttcctgcta
1381 aacagcaatg ccatggatgt ggtcctgcag ccgagccctg cccttagctg gaggtcgaca
1441 ggtgggatcc tggatgtcta catcttcctg ggcccagagc caagagcgt ggtgcagcag
1501 tacctggacg ttgtgggata cccgttcatg ccgccatact ggggcctggg cttccacctg
1561 tgccgctggg gctactcctc caccgctatc acccgccagg tggtggagaa catgaccagg
1621 gcccacttcc ccctggacgt ccaatggaac gacctggact acatggactc ccggagggac
1681 ttcacgttca acaaggatgg cttccgggac ttccggcca tggtgcagga gctgcaccag
1741 ggcggccggc gctacatgat gatcgtggat cctgccatca gcagctcggg ccctgccggg
1801 agctacaggc cctacgacga gggtctgcgg agggggttt tcatcaccaa cgagaccggc
1861 cagccgctga ttgggaaggt atggcccggg tccactgcct tcccgactt caccaaccc
1921 acagccctgg cctggtggga ggacatggtg gctgagttcc atgaccaggt gcccttcgac
1981 ggcatgtgga ttgacatgaa cgagcctcc aacttcatca gaggctctga ggacggctgc
2041 cccaacaatg agctggagaa cccaccctac gtgcctgggg tggttggggg gaccctccag
2101 gcggccacca tctgtgcctc cagccaccag tttctctcca cacactacaa cctgcacaac
2161 ctctacggcc tgaccgaagc catcgcctcc cacagggcgc tggtgaaggc tcgggggaca
2221 cgcccatttg tgatctcccg ctcgaccttt gctggccacg ccgatacgc cggccactgg
2281 acggggggacg tgtggagctc ctgggagcag ctcgcctcct ccgtgccaga aatcctgcag
2341 tttaacctgc tgggggtgcc tctggtcggg gccgacgtct gcggcttcct gggcaacacc
2401 tcagaggagc tgtgtgtgcg ctggaccag ctgggggcct ctacccctt catgcggaac
2461 cacaacagcc tgctcagtct gccccaggag ccgtacagct cagcgagcc ggcccagcag
```

FIG. 9B

```
2521 gccatgagga aggccctcac cctgcgctac gcactcctcc cccacctcta cacactgttc
2581 caccaggccc acgtcgcggg ggagaccgtg gcccggcccc tcttcctgga gttccccaag
2641 gactctagca cctggactgt ggaccaccag ctcctgtggg gggaggccct gctcatcacc
2701 ccagtgctcc aggccgggaa ggccgaagtg actggctact tcccttggg cacatggtac
2761 gacctgcaga cggtgccaat agaggccctt ggcagcctcc caccccacc tgcagctccc
2821 cgtgagccag ccatccacag cgaggggcag tgggtgacgc tgccggcccc cctggacacc
2881 atcaacgtcc acctccgggc tgggtacatc atcccctgc agggccctgg cctcacaacc
2941 acagagtccc gccagcagcc catggccctg gctgtggccc tgaccaaggg tggagaggcc
3001 cgaggggagc tgttctggga cgatggagag agcctggaag tgctggagcg aggggcctac
3061 acacaggtca tcttcctggc caggaataac acgatcgtga atgagctggt acgtgtgacc
3121 agtgagggag ctggcctgca gctgcagaag gtgactgtcc tgggcgtggc cacggcgccc
3181 cagcaggtcc tctccaacgg tgtccctgtc tccaacttca cctacagccc cgacaccaag
3241 gtcctggaca tctgtgtctc gctgttgatg ggagagcagt ttctcgtcag ctggtgttag
3301 ccgggcggag tgtgttagtc tctccagagg gaggctggtt ccccagggaa gcagagcctg
3361 tgtgcgggca gcagctgtgt gcgggcctgg gggttg 3397................3807
3808 tta agtgcaatta ttttaataaa aggggcatttggaatc
```

Human GAA with Alpha-1-antitrypsin signal peptide

SEQUENCE LISTING

```
<160> NUMBER OF SEQ ID NOS: 17

<210> SEQ ID NO 1
<211> LENGTH: 3846
<212> TYPE: DNA
<213> ORGANISM: Homo sapiens
<220> FEATURE:
<221> NAME/KEY: CDS
<222> LOCATION: (442)..(3300)

<400> SEQUENCE: 1
gcgcctgcgc gggaggccgc gtcacgtgac ccaccgcggc cccgccccgc gacgagctcc      60
cgccggtcac gtgacccgcc tctgcgcgcc cccgggcacg accccggagt ctccgcgggc     120
ggccagggcg cgcgtgcgcg gaggtgagcc gggccggggc tgcggggctt ccctgagcgc     180
gggccgggtc ggtggggcgg tcggctgccc gcgccggcct ctcagttggg aaagctgagg     240
ttgtcgccgg ggccgcgggt ggaggtcggg gatgaggcag caggtaggac agtgacctcg     300
gtgacgcgaa ggacccccggc cacctctagg ttctcctcgt ccgcccgttg ttcagcgagg     360
gaggctctgg gcctgccgca gctgacgggg aaactgaggc acggagcggg cctgtaggag     420
ctgtccaggc catctccaac c atg gga gtg agg cac ccg ccc tgc tcc cac       471
                        Met Gly Val Arg His Pro Pro Cys Ser His
                        1               5                   10 cgg ctc ctg gcc gtc tgc gcc ctc gtg tcc ttg gca acc gct gca ctc        519
Arg Leu Leu Ala Val Cys Ala Leu Val Ser Leu Ala Thr Ala Ala Leu
                15                  20                  25 ctg ggg cac atc cta ctc cat gat ttc ctg ctg gtt ccc cga gag ctg        567
Leu Gly His Ile Leu Leu His Asp Phe Leu Leu Val Pro Arg Glu Leu
        30                  35                  40
```

```
                                                          -continued agt ggc tcc tcc cca gtc ctg gag gag act cac cca gct cac cag cag      615
Ser Gly Ser Ser Pro Val Leu Glu Glu Thr His Pro Ala His Gln Gln
            45                  50                  55 gga gcc agc aga cca ggg ccc cgg gat gcc cag gca cac ccc ggc cgt      663
Gly Ala Ser Arg Pro Gly Pro Arg Asp Ala Gln Ala His Pro Gly Arg
 60                  65                  70 ccc aga gca gtg ccc aca cag tgc gac gtc ccc ccc aac agc cgc ttc      711
Pro Arg Ala Val Pro Thr Gln Cys Asp Val Pro Pro Asn Ser Arg Phe
 75                  80                  85                  90 gat tgc gcc cct gac aag gcc atc acc cag gaa cag tgc gag gcc cgc      759
Asp Cys Ala Pro Asp Lys Ala Ile Thr Gln Glu Gln Cys Glu Ala Arg
                 95                 100                 105 ggc tgc tgc tac atc cct gca aag cag ggg ctg cag gga gcc cag atg      807
Gly Cys Cys Tyr Ile Pro Ala Lys Gln Gly Leu Gln Gly Ala Gln Met
            110                 115                 120 ggg cag ccc tgg tgc ttc ttc cca ccc agc tac ccc agc tac aag ctg      855
Gly Gln Pro Trp Cys Phe Phe Pro Pro Ser Tyr Pro Ser Tyr Lys Leu
        125                 130                 135 gag aac ctg agc tcc tct gaa atg ggc tac acg gcc acc ctg acc cgt      903
Glu Asn Leu Ser Ser Ser Glu Met Gly Tyr Thr Ala Thr Leu Thr Arg
    140                 145                 150 acc acc ccc acc ttc ttc ccc aag gac atc ctg acc ctg cgg ctg gac      951
Thr Thr Pro Thr Phe Phe Pro Lys Asp Ile Leu Thr Leu Arg Leu Asp
155                 160                 165                 170 gtg atg atg gag act gag aac cgc ctc cac ttc acg atc aaa gat cca      999
Val Met Met Glu Thr Glu Asn Arg Leu His Phe Thr Ile Lys Asp Pro
                175                 180                 185 gct aac agg cgc tac gag gtg ccc ttg gag acc ccg cgt gtc cac agc     1047
Ala Asn Arg Arg Tyr Glu Val Pro Leu Glu Thr Pro Arg Val His Ser
            190                 195                 200 cgg gca ccg tcc cca ctc tac agc gtg gag ttc tcc gag gag ccc ttc     1095
Arg Ala Pro Ser Pro Leu Tyr Ser Val Glu Phe Ser Glu Glu Pro Phe
        205                 210                 215 ggg gtg atc gtg cac cgg cag ctg gac ggc cgc gtg ctg ctg aac acg     1143
Gly Val Ile Val His Arg Gln Leu Asp Gly Arg Val Leu Leu Asn Thr
    220                 225                 230 acg gtg gcg ccc ctg ttc ttt gcg gac cag ttc ctt cag ctg tcc acc     1191
Thr Val Ala Pro Leu Phe Phe Ala Asp Gln Phe Leu Gln Leu Ser Thr
235                 240                 245                 250 tcg ctg ccc tcg cag tat atc aca ggc ctc gcc gag cac ctc agt ccc     1239
Ser Leu Pro Ser Gln Tyr Ile Thr Gly Leu Ala Glu His Leu Ser Pro
                255                 260                 265 ctg atg ctc agc acc agc tgg acc agg atc acc ctg tgg aac cgg gac     1287
Leu Met Leu Ser Thr Ser Trp Thr Arg Ile Thr Leu Trp Asn Arg Asp
            270                 275                 280 ctt gcg ccc acg ccc ggt gcg aac ctc tac ggg tct cac cct ttc tac     1335
Leu Ala Pro Thr Pro Gly Ala Asn Leu Tyr Gly Ser His Pro Phe Tyr
        285                 290                 295 ctg gcg ctg gag gac ggg ggg tcg gca cac ggg gtg ttc ctg cta aac     1383
Leu Ala Leu Glu Asp Gly Gly Ser Ala His Gly Val Phe Leu Leu Asn
    300                 305                 310 agc aat gcc atg gat gtg gtc ctg cag ccg agc cct gcc ctt agc tgg     1431
Ser Asn Ala Met Asp Val Val Leu Gln Pro Ser Pro Ala Leu Ser Trp
315                 320                 325                 330 agg tcg aca ggt ggg atc ctg gat gtc tac atc ttc ctg ggc cca gag     1479
Arg Ser Thr Gly Gly Ile Leu Asp Val Tyr Ile Phe Leu Gly Pro Glu
                335                 340                 345 ccc aag agc gtg gtg cag cag tac ctg gac gtt gtg gga tac ccg ttc     1527
Pro Lys Ser Val Val Gln Gln Tyr Leu Asp Val Val Gly Tyr Pro Phe
```

```
                        350                 355                 360
atg ccg cca tac tgg ggc ctg ggc ttc cac ctg tgc cgc tgg ggc tac       1575
Met Pro Pro Tyr Trp Gly Leu Gly Phe His Leu Cys Arg Trp Gly Tyr
        365                 370                 375 tcc tcc acc gct atc acc cgc cag gtg gtg gag aac atg acc agg gcc       1623
Ser Ser Thr Ala Ile Thr Arg Gln Val Val Glu Asn Met Thr Arg Ala
380                 385                 390 cac ttc ccc ctg gac gtc caa tgg aac gac ctg gac tac atg gac tcc       1671
His Phe Pro Leu Asp Val Gln Trp Asn Asp Leu Asp Tyr Met Asp Ser
395                 400                 405                 410 cgg agg gac ttc acg ttc aac aag gat ggc ttc cgg gac ttc ccg gcc       1719
Arg Arg Asp Phe Thr Phe Asn Lys Asp Gly Phe Arg Asp Phe Pro Ala
            415                 420                 425 atg gtg cag gag ctg cac cag ggc ggc cgg cgc tac atg atg atc gtg       1767
Met Val Gln Glu Leu His Gln Gly Gly Arg Arg Tyr Met Met Ile Val
                430                 435                 440 gat cct gcc atc agc agc tcg ggc cct gcc ggg agc tac agg ccc tac       1815
Asp Pro Ala Ile Ser Ser Ser Gly Pro Ala Gly Ser Tyr Arg Pro Tyr
                    445                 450                 455 gac gag ggt ctg cgg agg ggg gtt ttc atc acc aac gag acc ggc cag       1863
Asp Glu Gly Leu Arg Arg Gly Val Phe Ile Thr Asn Glu Thr Gly Gln
460                 465                 470 ccg ctg att ggg aag gta tgg ccc ggg tcc act gcc ttc ccc gac ttc       1911
Pro Leu Ile Gly Lys Val Trp Pro Gly Ser Thr Ala Phe Pro Asp Phe
475                 480                 485                 490 acc aac ccc aca gcc ctg gcc tgg tgg gag gac atg gtg gct gag ttc       1959
Thr Asn Pro Thr Ala Leu Ala Trp Trp Glu Asp Met Val Ala Glu Phe
                495                 500                 505 cat gac cag gtg ccc ttc gac ggc atg tgg att gac atg aac gag cct       2007
His Asp Gln Val Pro Phe Asp Gly Met Trp Ile Asp Met Asn Glu Pro
                    510                 515                 520 tcc aac ttc atc aga ggc tct gag gac ggc tgc ccc aac aat gag ctg       2055
Ser Asn Phe Ile Arg Gly Ser Glu Asp Gly Cys Pro Asn Asn Glu Leu
                525                 530                 535 gag aac cca ccc tac gtg cct ggg gtg gtt ggg ggg acc ctc cag gcg       2103
Glu Asn Pro Pro Tyr Val Pro Gly Val Val Gly Gly Thr Leu Gln Ala
540                 545                 550 gcc acc atc tgt gcc tcc agc cac cag ttt ctc tcc aca cac tac aac       2151
Ala Thr Ile Cys Ala Ser Ser His Gln Phe Leu Ser Thr His Tyr Asn
555                 560                 565                 570 ctg cac aac ctc tac ggc ctg acc gaa gcc atc gcc tcc cac agg gcg       2199
Leu His Asn Leu Tyr Gly Leu Thr Glu Ala Ile Ala Ser His Arg Ala
                575                 580                 585 ctg gtg aag gct cgg ggg aca cgc cca ttt gtg atc tcc cgc tcg acc       2247
Leu Val Lys Ala Arg Gly Thr Arg Pro Phe Val Ile Ser Arg Ser Thr
                590                 595                 600 ttt gct ggc cac ggc cga tac gcc ggc cac tgg acg ggg gac gtg tgg       2295
Phe Ala Gly His Gly Arg Tyr Ala Gly His Trp Thr Gly Asp Val Trp
                    605                 610                 615 agc tcc tgg gag cag ctc gcc tcc tcc gtg cca gaa atc ctg cag ttt       2343
Ser Ser Trp Glu Gln Leu Ala Ser Ser Val Pro Glu Ile Leu Gln Phe
620                 625                 630 aac ctg ctg ggg gtg cct ctg gtc ggg gcc gac gtc tgc ggc ttc ctg       2391
Asn Leu Leu Gly Val Pro Leu Val Gly Ala Asp Val Cys Gly Phe Leu
635                 640                 645                 650 ggc aac acc tca gag gag ctg tgt gtg cgc tgg acc cag ctg ggg gcc       2439
Gly Asn Thr Ser Glu Glu Leu Cys Val Arg Trp Thr Gln Leu Gly Ala
                655                 660                 665 ttc tac ccc ttc atg cgg aac cac aac agc ctg ctc agt ctg ccc cag       2487
```

-continued

```
            Phe Tyr Pro Phe Met Arg Asn His Asn Ser Leu Leu Ser Leu Pro Gln
                            670                 675                 680 gag ccg tac agc ttc agc gag ccg gcc cag cag gcc atg agg aag gcc        2535
Glu Pro Tyr Ser Phe Ser Glu Pro Ala Gln Gln Ala Met Arg Lys Ala
            685                 690                 695 ctc acc ctg cgc tac gca ctc ctc ccc cac ctc tac aca ctg ttc cac        2583
Leu Thr Leu Arg Tyr Ala Leu Leu Pro His Leu Tyr Thr Leu Phe His
700                 705                 710 cag gcc cac gtc gcg ggg gag acc gtg gcc cgg ccc ctc ttc ctg gag        2631
Gln Ala His Val Ala Gly Glu Thr Val Ala Arg Pro Leu Phe Leu Glu
715                 720                 725                 730 ttc ccc aag gac tct agc acc tgg act gtg gac cac cag ctc ctg tgg        2679
Phe Pro Lys Asp Ser Ser Thr Trp Thr Val Asp His Gln Leu Leu Trp
                735                 740                 745 ggg gag gcc ctc ctc atc acc cca gtg ctc cag gcc ggg aag gcc gaa        2727
Gly Glu Ala Leu Leu Ile Thr Pro Val Leu Gln Ala Gly Lys Ala Glu
            750                 755                 760 gtg act ggc tac ttc ccc ttg ggc aca tgg tac gac ctg cag acg gtg        2775
Val Thr Gly Tyr Phe Pro Leu Gly Thr Trp Tyr Asp Leu Gln Thr Val
        765                 770                 775 cca ata gag gcc ctt ggc agc ctc cca ccc cca cct gca gct ccc cgt        2823
Pro Ile Glu Ala Leu Gly Ser Leu Pro Pro Pro Ala Ala Pro Arg
    780                 785                 790 gag cca gcc atc cac agc gag ggg cag tgg gtg acg ctg ccg gcc ccc        2871
Glu Pro Ala Ile His Ser Glu Gly Gln Trp Val Thr Leu Pro Ala Pro
795                 800                 805                 810 ctg gac acc atc aac gtc cac ctc cgg gct ggg tac atc atc ccc ctg        2919
Leu Asp Thr Ile Asn Val His Leu Arg Ala Gly Tyr Ile Ile Pro Leu
                815                 820                 825 cag ggc cct ggc ctc aca acc aca gag tcc cgc cag cag ccc atg gcc        2967
Gln Gly Pro Gly Leu Thr Thr Thr Glu Ser Arg Gln Gln Pro Met Ala
            830                 835                 840 ctg gct gtg gcc ctg acc aag ggt gga gag gcc cga ggg gag ctg ttc        3015
Leu Ala Val Ala Leu Thr Lys Gly Gly Glu Ala Arg Gly Glu Leu Phe
        845                 850                 855 tgg gac gat gga gag agc ctg gaa gtg ctg gag cga ggg gcc tac aca        3063
Trp Asp Asp Gly Glu Ser Leu Glu Val Leu Glu Arg Gly Ala Tyr Thr
    860                 865                 870 cag gtc atc ttc ctg gcc agg aat aac acg atc gtg aat gag ctg gta        3111
Gln Val Ile Phe Leu Ala Arg Asn Asn Thr Ile Val Asn Glu Leu Val
875                 880                 885                 890 cgt gtg acc agt gag gga gct ggc ctg cag ctg cag aag gtg act gtc        3159
Arg Val Thr Ser Glu Gly Ala Gly Leu Gln Leu Gln Lys Val Thr Val
                895                 900                 905 ctg ggc gtg gcc acg gcg ccc cag cag gtc ctc tcc aac ggt gtc cct        3207
Leu Gly Val Ala Thr Ala Pro Gln Gln Val Leu Ser Asn Gly Val Pro
            910                 915                 920 gtc tcc aac ttc acc tac agc ccc gac acc aag gtc ctg gac atc tgt        3255
Val Ser Asn Phe Thr Tyr Ser Pro Asp Thr Lys Val Leu Asp Ile Cys
        925                 930                 935 gtc tcg ctg ttg atg gga gag cag ttt ctc gtc agc tgg tgt tag           3300
Val Ser Leu Leu Met Gly Glu Gln Phe Leu Val Ser Trp Cys
    940                 945                 950 ccgggcggag tgtgttagtc tctccagagg gaggctggtt ccccagggaa gcagagcctg      3360
tgtgcgggca gcagctgtgt gcgggcctgg gggttgcatg tgtcacctgg agctgggcac      3420
taaccattcc aagccgccgc atcgcttgtt tccacctcct gggccggggc tctggccccc      3480
aacgtgtcta ggagagcttt ctccctagat cgcactgtgg gccggggcct ggagggctgc      3540
```

```
tctgtgttaa taagattgta aggtttgccc tcctcacctg ttgccggcat gcgggtagta    3600
ttagccaccc ccctccatct gttcccagca ccggagaagg gggtgctcag gtggaggtgt    3660
ggggtatgca cctgagctcc tgcttcgcgc ctgctgctct gccccaacgc gaccgcttcc    3720
cggctgccca gagggctgga tgcctgccgg tccccgagca agcctgggaa ctcaggaaaa    3780
ttcacaggac ttgggagatt ctaaatctta agtgcaatta ttttaataaa agggcatttt    3840
ggaatc                                                               3846

<210> SEQ ID NO 2
<211> LENGTH: 952
<212> TYPE: PRT
<213> ORGANISM: Homo sapiens

<400> SEQUENCE: 2
```

| | | | | | | | | | | | | | | | |
|---|---|---|---|---|---|---|---|---|---|---|---|---|---|---|---|
| Met | Gly | Val | Arg | His | Pro | Pro | Cys | Ser | His | Arg | Leu | Leu | Ala | Val | Cys |
| 1 | | | | 5 | | | | | 10 | | | | | 15 | |
| Ala | Leu | Val | Ser | Leu | Ala | Thr | Ala | Ala | Leu | Leu | Gly | His | Ile | Leu | Leu |
| | | | 20 | | | | | 25 | | | | | 30 | | |
| His | Asp | Phe | Leu | Leu | Val | Pro | Arg | Glu | Leu | Ser | Gly | Ser | Ser | Pro | Val |
| | | | 35 | | | | | 40 | | | | | 45 | | |
| Leu | Glu | Glu | Thr | His | Pro | Ala | His | Gln | Gln | Gly | Ala | Ser | Arg | Pro | Gly |
| 50 | | | | | 55 | | | | | 60 | | | | | |
| Pro | Arg | Asp | Ala | Gln | Ala | His | Pro | Gly | Arg | Pro | Arg | Ala | Val | Pro | Thr |
| 65 | | | | | 70 | | | | | 75 | | | | | 80 |
| Gln | Cys | Asp | Val | Pro | Pro | Asn | Ser | Arg | Phe | Asp | Cys | Ala | Pro | Asp | Lys |
| | | | | 85 | | | | | 90 | | | | | 95 | |
| Ala | Ile | Thr | Gln | Glu | Gln | Cys | Glu | Ala | Arg | Gly | Cys | Cys | Tyr | Ile | Pro |
| | | | 100 | | | | | 105 | | | | | 110 | | |
| Ala | Lys | Gln | Gly | Leu | Gln | Gly | Ala | Gln | Met | Gly | Gln | Pro | Trp | Cys | Phe |
| | | | 115 | | | | | 120 | | | | | 125 | | |
| Phe | Pro | Pro | Ser | Tyr | Pro | Ser | Tyr | Lys | Leu | Glu | Asn | Leu | Ser | Ser | Ser |
| 130 | | | | | 135 | | | | | 140 | | | | | |
| Glu | Met | Gly | Tyr | Thr | Ala | Thr | Leu | Thr | Arg | Thr | Thr | Pro | Thr | Phe | Phe |
| 145 | | | | | 150 | | | | | 155 | | | | | 160 |
| Pro | Lys | Asp | Ile | Leu | Thr | Leu | Arg | Leu | Asp | Val | Met | Met | Glu | Thr | Glu |
| | | | | 165 | | | | | 170 | | | | | 175 | |
| Asn | Arg | Leu | His | Phe | Thr | Ile | Lys | Asp | Pro | Ala | Asn | Arg | Arg | Tyr | Glu |
| | | | 180 | | | | | 185 | | | | | 190 | | |
| Val | Pro | Leu | Glu | Thr | Pro | Arg | Val | His | Ser | Arg | Ala | Pro | Ser | Pro | Leu |
| | | | 195 | | | | | 200 | | | | | 205 | | |
| Tyr | Ser | Val | Glu | Phe | Ser | Glu | Glu | Pro | Phe | Gly | Val | Ile | Val | His | Arg |
| 210 | | | | | 215 | | | | | 220 | | | | | |
| Gln | Leu | Asp | Gly | Arg | Val | Leu | Leu | Asn | Thr | Thr | Val | Ala | Pro | Leu | Phe |
| 225 | | | | | 230 | | | | | 235 | | | | | 240 |
| Phe | Ala | Asp | Gln | Phe | Leu | Gln | Leu | Ser | Thr | Ser | Leu | Pro | Ser | Gln | Tyr |
| | | | | 245 | | | | | 250 | | | | | 255 | |
| Ile | Thr | Gly | Leu | Ala | Glu | His | Leu | Ser | Pro | Leu | Met | Leu | Ser | Thr | Ser |
| | | | 260 | | | | | 265 | | | | | 270 | | |
| Trp | Thr | Arg | Ile | Thr | Leu | Trp | Asn | Arg | Asp | Leu | Ala | Pro | Thr | Pro | Gly |
| | | | 275 | | | | | 280 | | | | | 285 | | |
| Ala | Asn | Leu | Tyr | Gly | Ser | His | Pro | Phe | Tyr | Leu | Ala | Leu | Glu | Asp | Gly |
| | | | 290 | | | | | 295 | | | | | 300 | | |
| Gly | Ser | Ala | His | Gly | Val | Phe | Leu | Leu | Asn | Ser | Asn | Ala | Met | Asp | Val |
| 305 | | | | | 310 | | | | | 315 | | | | | 320 |

-continued

```
Val Leu Gln Pro Ser Pro Ala Leu Ser Trp Arg Ser Thr Gly Gly Ile
                325                 330                 335

Leu Asp Val Tyr Ile Phe Leu Gly Pro Glu Pro Lys Ser Val Val Gln
            340                 345                 350

Gln Tyr Leu Asp Val Val Gly Tyr Pro Phe Met Pro Pro Tyr Trp Gly
        355                 360                 365

Leu Gly Phe His Leu Cys Arg Trp Gly Tyr Ser Ser Thr Ala Ile Thr
    370                 375                 380

Arg Gln Val Val Glu Asn Met Thr Arg Ala His Phe Pro Leu Asp Val
385                 390                 395                 400

Gln Trp Asn Asp Leu Asp Tyr Met Asp Ser Arg Arg Asp Phe Thr Phe
                405                 410                 415

Asn Lys Asp Gly Phe Arg Asp Phe Pro Ala Met Val Gln Glu Leu His
            420                 425                 430

Gln Gly Gly Arg Arg Tyr Met Met Ile Val Asp Pro Ala Ile Ser Ser
        435                 440                 445

Ser Gly Pro Ala Gly Ser Tyr Arg Pro Tyr Asp Glu Gly Leu Arg Arg
    450                 455                 460

Gly Val Phe Ile Thr Asn Glu Thr Gly Gln Pro Leu Ile Gly Lys Val
465                 470                 475                 480

Trp Pro Gly Ser Thr Ala Phe Pro Asp Phe Thr Asn Pro Thr Ala Leu
                485                 490                 495

Ala Trp Trp Glu Asp Met Val Ala Glu Phe His Asp Gln Val Pro Phe
            500                 505                 510

Asp Gly Met Trp Ile Asp Met Asn Glu Pro Ser Asn Phe Ile Arg Gly
        515                 520                 525

Ser Glu Asp Gly Cys Pro Asn Asn Glu Leu Glu Asn Pro Pro Tyr Val
    530                 535                 540

Pro Gly Val Val Gly Gly Thr Leu Gln Ala Ala Thr Ile Cys Ala Ser
545                 550                 555                 560

Ser His Gln Phe Leu Ser Thr His Tyr Asn Leu His Asn Leu Tyr Gly
                565                 570                 575

Leu Thr Glu Ala Ile Ala Ser His Arg Ala Leu Val Lys Ala Arg Gly
            580                 585                 590

Thr Arg Pro Phe Val Ile Ser Arg Ser Thr Phe Ala Gly His Gly Arg
        595                 600                 605

Tyr Ala Gly His Trp Thr Gly Asp Val Trp Ser Ser Trp Glu Gln Leu
    610                 615                 620

Ala Ser Ser Val Pro Glu Ile Leu Gln Phe Asn Leu Leu Gly Val Pro
625                 630                 635                 640

Leu Val Gly Ala Asp Val Cys Gly Phe Leu Gly Asn Thr Ser Glu Glu
                645                 650                 655

Leu Cys Val Arg Trp Thr Gln Leu Gly Ala Phe Tyr Pro Phe Met Arg
            660                 665                 670

Asn His Asn Ser Leu Leu Ser Leu Pro Gln Glu Pro Tyr Ser Phe Ser
        675                 680                 685

Glu Pro Ala Gln Gln Ala Met Arg Lys Ala Leu Thr Leu Arg Tyr Ala
    690                 695                 700

Leu Leu Pro His Leu Tyr Thr Leu Phe His Gln Ala His Val Ala Gly
705                 710                 715                 720

Glu Thr Val Ala Arg Pro Leu Phe Leu Glu Phe Pro Lys Asp Ser Ser
                725                 730                 735
```

```
Thr Trp Thr Val Asp His Gln Leu Leu Trp Gly Glu Ala Leu Leu Ile
            740                 745                 750

Thr Pro Val Leu Gln Ala Gly Lys Ala Glu Val Thr Gly Tyr Phe Pro
        755                 760                 765

Leu Gly Thr Trp Tyr Asp Leu Gln Thr Val Pro Ile Glu Ala Leu Gly
    770                 775                 780

Ser Leu Pro Pro Pro Ala Ala Pro Arg Glu Pro Ala Ile His Ser
785                 790                 795                 800

Glu Gly Gln Trp Val Thr Leu Pro Ala Pro Leu Asp Thr Ile Asn Val
                805                 810                 815

His Leu Arg Ala Gly Tyr Ile Ile Pro Leu Gln Gly Pro Gly Leu Thr
            820                 825                 830

Thr Thr Glu Ser Arg Gln Gln Pro Met Ala Leu Ala Val Ala Leu Thr
        835                 840                 845

Lys Gly Gly Glu Ala Arg Gly Glu Leu Phe Trp Asp Asp Gly Glu Ser
    850                 855                 860

Leu Glu Val Leu Glu Arg Gly Ala Tyr Thr Gln Val Ile Phe Leu Ala
865                 870                 875                 880

Arg Asn Asn Thr Ile Val Asn Glu Leu Val Arg Val Thr Ser Glu Gly
                885                 890                 895

Ala Gly Leu Gln Leu Gln Lys Val Thr Val Leu Gly Val Ala Thr Ala
            900                 905                 910

Pro Gln Gln Val Leu Ser Asn Gly Val Pro Val Ser Asn Phe Thr Tyr
        915                 920                 925

Ser Pro Asp Thr Lys Val Leu Asp Ile Cys Val Ser Leu Leu Met Gly
    930                 935                 940

Glu Gln Phe Leu Val Ser Trp Cys
945                 950

<210> SEQ ID NO 3
<211> LENGTH: 3026
<212> TYPE: DNA
<213> ORGANISM: Homo sapiens

<400> SEQUENCE: 3
gcctgtagga gctgtccagg ccatctccaa ccatgggagt gaggcacccg ccctgctccc     60
accggctcct ggccgtctgc gccctcgtgt ccttggcaac cgctgcactc ctggggcaca    120
tcctactcca tgatttcctg ctggttcccc gagagctgag tggctcctcc ccagtcctgg    180
aggagactca cccagctcac cagcagggag ccagcagacc agggccccgg gatgcccagg    240
cacaccccgg ccgtcccaga gcagtgccca cacagtgcga cgtccccccc aacagccgct    300
tcgattgcgc cctgacaag gccatcaccc aggaacagtg cgaggcccgc ggctgctgct    360
acatccctgc aaagcagggg ctgcaggag cccagatggg gcagccctgg tgcttcttcc    420
cacccagcta cccagctac aagctggaga acctgagctc ctctgaaatg ggctacacgg    480 ccacctgac ccgtaccacc cccaccttct tccccaagga catcctgacc ctgcggctgg    540
acgtgatgat ggagactgag aaccgcctcc acttcacgat caaagatcca gctaacaggc    600
gctacgaggt gcccttggag accccgcgtg tccacagccg ggcaccgtcc ccactctaca    660
gcgtggagtt ctccgaggag cccttcgggg tgatcgtgca ccggcagctg gacggccgcg    720
tgctgctgaa cacgacggtg gcgcccctgt tctttgcgga ccagttcctt cagctgtcca    780
cctcgctgcc ctcgcagtat atcacaggcc tcgccgagca cctcagtccc tgatgctca    840 gcaccagctg gaccaggatc accctgtgga accgggacct tgcgcccacg cccggtgcga    900
```

```
acctctacgg gtctcaccct ttctacctgg cgctggagga cggcgggtcg gcacacgggg    960
tgttcctgct aaacagcaat gccatggatg tggtcctgca ccgagccct gcccttagct    1020 ggaggtcgac aggtgggatc ctggatgtct acatcttcct gggcccagag cccaagagcg    1080
tggtgcagca gtacctggac gttgtgggat acccgttcat gccgccatac tggggcctgg    1140
gcttccacct gtgccgctgg ggctactcct ccaccgctat cacccgccag gtggtggaga    1200
acatgaccag ggcccacttc cccctggacg tccaatggaa cgacctggac tacatggact    1260
cccggaggga cttcacgttc aacaaggatg gcttccggga cttcccggcc atggtgcagg    1320
agctgcacca gggcggccgg cgctacatga tgatcgtgga tcctgccatc agcagctcgg    1380
gccctgccgg gagctacagg ccctacgacg agggtctgcg gaggggggtt ttcatcacca    1440
acgagaccgg ccagccgctg attgggaagg tatggcccgg gtccactgcc ttccccgact    1500
tcaccaaccc cacagccctg gcctggtggg aggacatggt ggctgagttc catgaccagg    1560
tgcccttcga cggcatgtgg attgacatga acgagccttc caacttcatc agaggctctg    1620
aggacggctg ccccaacaat gagctggaga acccacccta cgtgcctggg gtggttgggg    1680
ggaccctcca ggcggccacc atctgtgcct ccagccacca gttttctctcc acacactaca    1740 acctgcacaa cctctacggc ctgaccgaag ccatcgcctc ccacagggcg ctggtgaagg    1800
ctcgggggac acgcccattt gtgatctccc gctcgacctt tgctggccac ggccgatacg    1860
ccggccactg gacgggggac gtgtggagct cctgggagca gctcgcctcc tccgtgccag    1920
aaatcctgca gtttaacctg ctgggggtgc tctggtcgg ggccgacgtc tgcggcttcc    1980
tgggcaacac ctcagaggag ctgtgtgtgc gctggaccca gctgggggcc ttctacccct    2040
tcatgcggaa ccacaacagc ctgctcagtc tgccccagga gccgtacagc ttcagcgagc    2100
cggcccagca ggccatgagg aaggccctca ccctgcgcta cgcactcctc ccccacctct    2160
acacactgtt ccaccaggcc cacgtcgcgg gggagaccgt ggcccggccc ctcttcctgg    2220
agttccccaa ggactctagc acctggactg tggaccacca gctcctgtgg ggggaggccc    2280
tgctcatcac cccagtgctc caggccggga aggccgaagt gactggctac ttccccttgg    2340
gcacatggta cgacctgcag acggtgccaa tagaggccct tggcagcctc ccacccccac    2400
ctgcagctcc ccgtgagcca gccatccaca gcgaggggca gtgggtgacg ctgccggccc    2460
ccctggacac catcaacgtc cacctccggg ctgggtacat catcccctg cagggccctg    2520 gcctcacaac cacagagtcc cgccagcagc ccatggccct ggctgtggcc ctgaccaagg    2580
gtggagaggc ccgaggggag ctgttctggg acgatgagag gagcctggaa gtgctggagc    2640
gaggggccta cacacaggtc atcttcctgg ccaggaataa cacgatcgtg aatgagctgg    2700
tacgtgtgac cagtgaggga gctggcctgc agctgcagaa ggtgactgtc ctgggcgtgg    2760
ccacggcgcc ccagcaggtc ctctccaacg gtgtccctgt ctccaacttc acctacagcc    2820
ccgacaccaa ggtcctggac atctgtgtct cgctgttgat gggagagcag tttctcgtca    2880
gctggtgtta gccgggcgga gtgtgttagt ctctccagag ggaggctggt tccccaggga    2940
agcagagcct gtgtgcgggc agcagctgtg tgcgggcctg ggggttgtta agtgcaatta    3000
ttttaataaa aggggcattt ggaatc                                        3026
```

<210> SEQ ID NO 4
<211> LENGTH: 27
<212> TYPE: PRT
<213> ORGANISM: Homo sapiens

-continued

```
<400> SEQUENCE: 4

Met Gly Val Arg His Pro Pro Cys Ser His Arg Leu Leu Ala Val Cys
1               5                   10                  15

Ala Leu Val Ser Leu Ala Thr Ala Ala Leu Leu
            20                  25

<210> SEQ ID NO 5
<211> LENGTH: 21
<212> TYPE: PRT
<213> ORGANISM: Artificial Sequence
<220> FEATURE:
<223> OTHER INFORMATION: Artificial secretory signal

<400> SEQUENCE: 5

Met Trp Trp Arg Leu Trp Trp Leu Leu Leu Leu Leu Leu Leu Leu Trp
1               5                   10                  15

Pro Met Val Trp Ala
            20

<210> SEQ ID NO 6
<211> LENGTH: 27
<212> TYPE: PRT
<213> ORGANISM: Homo sapiens

<400> SEQUENCE: 6

Met Gly Val His Glu Cys Pro Ala Trp Leu Trp Leu Leu Leu Ser Leu
1               5                   10                  15

Leu Ser Leu Pro Leu Gly Leu Pro Val Leu Gly
            20                  25

<210> SEQ ID NO 7
<211> LENGTH: 18
<212> TYPE: PRT
<213> ORGANISM: Homo sapiens

<400> SEQUENCE: 7

Met Lys Trp Val Thr Phe Ile Ser Leu Leu Phe Leu Phe Ser Ser Ala
1               5                   10                  15

Tyr Ser

<210> SEQ ID NO 8
<211> LENGTH: 24
<212> TYPE: PRT
<213> ORGANISM: Homo sapiens

<400> SEQUENCE: 8

Met Pro Ser Ser Val Ser Trp Gly Ile Leu Leu Leu Ala Gly Leu Cys
1               5                   10                  15

Cys Leu Val Pro Val Ser Leu Ala
            20

<210> SEQ ID NO 9
<211> LENGTH: 46
<212> TYPE: PRT
<213> ORGANISM: Homo sapiens

<400> SEQUENCE: 9

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30
```

```
Asp His Glu Asn Ala Asn Lys Ile Leu Asn Arg Pro Lys Arg
        35                  40                  45
```

<210> SEQ ID NO 10
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 10
gctgcaaagc ttgggcacat cctactccat                                    30

<210> SEQ ID NO 11
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 11
cctgcagccc ctgctttgca gggatgtagc                                    30

<210> SEQ ID NO 12
<211> LENGTH: 105
<212> TYPE: DNA
<213> ORGANISM: Artificial Sequence
<220> FEATURE:
<223> OTHER INFORMATION: Synthetic oligonucleotide

<400> SEQUENCE: 12
agctgctgag gtacctcagc caccatgtgg tggcgcctgt ggtggctgct gctgctgctg    60
ctgctgctgt ggcccatggt gtgggccaag cttcgatgct acgtc                  105

<210> SEQ ID NO 13
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 13
gacgtagcat cgaagctt                                                 18

<210> SEQ ID NO 14
<211> LENGTH: 123
<212> TYPE: DNA
<213> ORGANISM: Artificial Sequence
<220> FEATURE:
<223> OTHER INFORMATION: Synthetic oligonucleotide

<400> SEQUENCE: 14
agctgctgag gtacctcagc caccatgggg gtgcacgaat gtcctgcctg gctgtggctt    60
ctcctgtccc tgctgtcgct ccctctgggc ctcccagtcc tgggcaagct tcgatgctac   120
gtc                                                                123

<210> SEQ ID NO 15
<211> LENGTH: 99
<212> TYPE: DNA
<213> ORGANISM: Artificial Sequence
<220> FEATURE:
<223> OTHER INFORMATION: Synthetic oligonucleotide

<400> SEQUENCE: 15

```
ctgaggtacc tgccaccatg ccgtcttctg tctcgtgggg catcctcctg ctggcaggcc      60
tgtgctgcct ggtccctgtc tccctggcta agcttcgat                             99

<210> SEQ ID NO 16
<211> LENGTH: 81
<212> TYPE: DNA
<213> ORGANISM: Artificial Sequence
<220> FEATURE:
<223> OTHER INFORMATION: Synthetic oligonucleotide

<400> SEQUENCE: 16
ctgaggtacc tgccaccatg aagtgggtaa cctttatttc ccttcttttt ctctttagct      60
cggcttattc caagcttcga t                                                81

<210> SEQ ID NO 17
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 17
ctgaggtacc tgccaccatg cagcgcgtga acatgatcat ggca                       44
```

CONSTRUCTS FOR EXPRESSING LYSOSOMAL POLYPEPTIDES

RELATED APPLICATION INFORMATION

This application is a continuation of U.S. application Ser. No. 10/761,530, filed Jan. 21, 2004 (abandoned), which claims the benefit of U.S. Provisional Application Nos. 60/441,789, filed Jan. 22, 2003, the entire contents of each of which are hereby incorporated by reference.

FIELD OF THE INVENTION

The present invention relates to novel nucleic acid constructs encoding lysosomal polypeptides, in particular lysosomal acid α-glucosidase, as well as methods of using the same to produce recombinant lysosomal polypeptides and to treat lysosomal polypeptide deficiencies.

BACKGROUND OF THE INVENTION

Glycogen storage disease type II (GSD II) is a classical lysosomal storage disorder, characterized by lysosomal accumulation of glycogen and tissue damage, primarily in muscle and heart (Hirschhorn, R. and Reuser, A. J. (2001) In *The Metabolic and Molecular Basis for Inherited Disease* (Scriver, C. R., Beaudet, A. L., Sly, W. S. & Valle, D. Eds.), pp. 3389-3419. McGraw-Hill, New York). The underlying enzyme deficiency is acid α-glucosidase (GAA). In severe, infantile GSD II progressive cardiomyopathy and myopathy lead to cardiorespiratory failure and death by 1 year of age. In milder, juvenile and adult-onset GSD II, progressive weakness and respiratory failure are disabling and death from respiratory failure occurs.

Animal models for human lysosomal acid α-glucosidase (hGAA) deficiency accurately mimic GSD II, and the efficacy of approaches to gene therapy for GSD II can be evaluated in these systems. The GAA knockout (GAA-KO) mouse model accumulated glycogen in skeletal and cardiac muscle, and developed weakness and reduced mobility (Raben, N., et al. (1998) *J. Biol. Chem.* 273:19086-19092, Bijvoet, A. G., et al. (1998) *Hum. Mol. Genet.* 7:53-62). The administration of recombinant GAA to a GAA-KO mouse demonstrated uptake of GAA by skeletal muscle, presumably through receptor-mediated uptake and delivery of GAA to the lysosomes (Bijvoet, A. G. et al., (1998) *Hum. Mol. Genet.* 7:1815-1824). The Japanese quail model is similar to juvenile-onset GSD II, and has been treated successfully with recombinant enzyme replacement (Kikuchi, T., et al. (1998) *J. Clin. Invest.* 101:827-833). Enzyme therapy has demonstrated efficacy for severe, infantile GSD II; however the benefit of enzyme therapy is limited by the need for frequent infusions and the development of inhibitor antibodies against recombinant hGAA (Amalfitano, A., et al. (2001) *Genet. In Med.* 3:132-138). As an alternative or adjunct to enzyme therapy, the feasibility of gene therapy approaches to treat GSD-II have been investigated (Amalfitano, A., et al., (1999) *Proc. Natl. Acad. Sci. USA* 96:8861-8866, Ding, E., et al. (2002) *Mol. Ther.* 5:436-446, Fraites, T. J., et al., (2002) *Mol. Ther.* 5:571-578, Tsujino, S., et al. (1998) *Hum. Gene Ther.* 9:1609-1616).

Administration of an adenovirus (Ad) vector encoding hGAA that was targeted to mouse liver in the GAA-KO mouse model reversed the glycogen accumulation in skeletal and cardiac muscle within 12 days through secretion of hGAA from the liver and uptake in other tissues (Amalfitano, A., et al., (1999) *Proc. Natl. Acad. Sci. USA* 96:8861-8866). Antibodies against hGAA abbreviated the duration of hGAA secretion with an Ad vector in liver, although vector DNA and hGAA persisted in tissues at reduced levels for many weeks (Ding, E., et al., (2002) *Mol. Ther.* 5:436-446). Introduction of adeno-associate virus 2 (AAV2) vectors encoding GAA normalized the GAA activity in the injected skeletal muscle and the injected cardiac muscle, and glycogen content was normalized in muscle when an AAV1-pseudotyped vector was administered with improved muscle transduction (Fraites, T. J., et al. (2002) *Mol. Ther.* 5:571-578). Muscle-targeted Ad vector gene therapy was attempted in the Japanese quail model, although only localized reversal of glycogen accumulation at the site of vector injection was achieved (Tsujino, S., et al. (1998) *Hum. Gene Ther.* 9:1609-1616).

Neonatal gene therapy may have greater efficacy than administration later in life, as evidenced by experiments in several rodent disease models. An AAV vector administered intravenously on the second day of life in β-glucoronidase deficient (Sly disease) mice produced therapeutically relevant levels of β-glucoronidase and corrected lysosomal storage in multiple tissues, including liver and kidney (Daly, T. M., et al. (1999) *Proc. Natl. Acad. Sci. USA* 96:2296-2300). Similarly, intramuscular injection of the AAV vector produced sustained, therapeutic levels of expression of β-glucoronidase and eliminated lysosomal storage in muscle and liver (Daly, T. M., et al., (1999) *Hum. Gene Ther.* 10:85-94). AAV vector DNA persisted in muscle and in transduced areas of the liver following neonatal intramuscular injection in the Sly disease mouse (Daly, T. M., et al. (1999) *Hum. Gene Ther.* 10:85-94). The number of AAV vector particles administered to neonatal Sly mice was approximately 100-fold less than was needed to produce therapeutically relevant levels of proteins in adult mice (Kessler, P. D., et al. (1996) *Proc. Natl. Acad. Sci. USA* 93:14082-14087, Herzog, R. W., et al. (1997) *Proc. Natl. Acad. Sci. USA* 94:5804-5809, Nakai, H., et al. (1998) *Blood* 91:4600-4607, Snyder, R. O., et al. (1997) *Nat. Genet.* 16:270-276, Koeberl, D. D., et al. (1999) *Hum. Gene Ther.* 10:2133-2140, Snyder, R. O., et al. (1999) *Nat. Med.* 5:64-70, Herzog, R. W. et al. (1999) *Nat. Med.* 5:56-63).

There is a need in the art for improved methods of producing lysosomal polypeptides such as GAA in vitro and in vivo, for example, to treat lysosomal polypeptide deficiencies. Further, there is a need for methods that result in systemic delivery of GAA and other lysosomal polypeptides to affected tissues and organs.

SUMMARY OF THE INVENTION

The present invention is based, in part, on the discovery of improved nucleic acid constructs for expressing lysosomal polypeptides such as GAA. One aspect of the invention provides an isolated nucleic acid encoding a chimeric polypeptide comprising a lysosomal polypeptide operably linked to a secretory signal sequence such that targeting of the lysosomal polypeptide to the secretory pathway (i.e., instead of to the lysosome) is enhanced. As another aspect, the invention encompasses isolated nucleic acids comprising a coding sequence for GAA and an "abbreviated" 3' untranslated region (3' UTR). The isolated nucleic acids of the invention can be used to produce recombinant lysosomal polypeptides in vitro (e.g., in cultured cells) or in vivo (e.g., in an animal or plant based protein production system or in methods of therapeutic treatment). In addition, improved (i.e., higher) titers of viral vectors encoding lysosomal polypeptides can be produced with the isolated nucleic acids of the invention.

Accordingly, as one aspect, the present invention provides an isolated nucleic acid encoding a chimeric polypeptide comprising a secretory signal sequence operably linked to a lysosomal polypeptide (e.g., GAA). Also provided is the chimeric polypeptide comprising the secretory signal sequence operably linked to the lysosomal polypeptide.

As another aspect, the present invention provides isolated nucleic acids comprising a GAA coding sequence and an "abbreviated" 3' UTR. In one representative embodiment, the invention provides an isolated nucleic acid encoding a GAA, the isolated nucleic acid comprising: (a) a coding region encoding a GAA, and (b) an abbreviated 3' UTR, wherein the 3' untranslated region is a GAA 3' UTR comprising a deletion therein (e.g., a deletion of at least 25 consecutive nucleotides), so that upon introduction into a cell, GAA polypeptide is produced at a higher level from the isolated nucleic acid as compared with GAA polypeptide production from an isolated nucleic acid comprising a full-length GAA 3' UTR. In an exemplary embodiment, the 3' UTR comprises a deletion in the region shown as nucleotides 3301 through 3846 of SEQ ID NO:1 (FIG. 8).

In another representative embodiment, the invention provides an isolated nucleic acid encoding a GAA, the isolated nucleic acid comprising: (a) a coding region encoding a GAA, and (b) an abbreviated 3' UTR, wherein the 3' UTR is less than about 200 nucleotides in length and comprises a segment that is heterologous to the GAA coding region, so that upon introduction into a cell, GAA polypeptide is produced at a higher level from the isolated nucleic acid as compared with GAA polypeptide production from an isolated nucleic acid comprising a full-length GAA 3' UTR.

In other particular embodiments, the lysosomal polypeptide is a human polypeptide and/or the isolated nucleic acid is operatively associated with a transcriptional control element that is operable in liver cells (optionally, with a liver-specific transcriptional control element).

As additional aspects, the present invention further provides vectors (including nonviral and viral vectors, the latter including adenovirus, AAV and hybrid adenovirus-AAV vectors), cells and pharmaceutical formulations comprising the isolated nucleic acids of this invention.

As still further aspects, the present invention provides methods of making delivery vectors (e.g., viral vectors) comprising the isolated nucleic acids of this invention.

Also provided are methods of using the isolated nucleic acids, vectors, cells, and pharmaceutical formulations of the invention to treat deficiencies of lysosomal polypeptides (e.g., GAA) and to produce recombinant lysosomal polypeptides (e.g., in vitro in cultured cells or in vivo in an animal or plant-based recombinant protein expression system or for therapeutic purposes).

In illustrative embodiments, the present invention is practiced to administer an isolated nucleic acid encoding a lysosomal polypeptide such as GAA to a subject (for example, a subject diagnosed with or suspected of having a deficiency of the lysosomal polypeptide). In particular representative embodiments, an isolated nucleic acid of the invention encoding a lysosomal polypeptide can be administered to one depot tissue or organ (e.g., liver, skeletal muscle, lung and the like) and the polypeptide expressed therein at levels sufficient to result in secretion into the systemic circulation, from which the secreted polypeptide is taken up by distal target tissues (e.g., skeletal, cardiac and/or diaphragm muscle). Similarly, the isolated nucleic acid can be delivered to brain cells (e.g., to treat MPS disorders such as Sly disease), where the lysosomal polypeptide can be expressed, secreted and taken up by non-transformed or non-transduced brain cells (e.g., neurons and glial cells).

In another particular embodiment, a recombinant adeno-associated virus (AAV) vector expressing an isolated nucleic acid encoding GAA of the invention is administered to the liver of a subject having GAA deficiency, which results in GAA polypeptide production at sufficiently high levels such that GAA polypeptide is secreted from the liver and taken up by skeletal muscle and/or other tissues, which advantageously leads to a reduction in glycogen content and/or an improvement in other clinical indicia of GAA deficiency in affected tissues.

As yet a further aspect, the present invention provides the use of the isolated nucleic acids, vectors, cells and pharmaceutical formulations of the invention in the manufacture of medicaments for the treatment of lysosomal polypeptide deficiencies (e.g., GAA deficiency).

These and other aspects of the invention are described in more detail in the description of the invention set forth below.

BRIEF DESCRIPTION OF THE DRAWINGS

FIG. 3. Antibodies in GAA-KO mouse plasma following neonatal Ad-AAV vector administration. (Panel A) The absorbance for anti-hGAA antibodies in an ELISA of GAA-KO mouse plasma at 6 weeks following neonatal Ad-AAV vector administration (Neonatal Intramuscular Ad-AAV), and of GAA-KO mouse plasma at 6 weeks following intravenous Ad-AAV vector administration ($4 \times 10^{10}$ particles) in adult mice (Ad-AAV). Controls consisted of untreated, GAA-KO mice (Control). Each column represents the mean and standard deviation for an individual mouse. Each dilution of plasma (1:100, 1:200, and 1:400) was analyzed in triplicate. (Panel B) The titer for anti-hGAA antibodies by ELISA, representing the same mice in the same order as in FIG. 1 Panel B. Each sample was analyzed in duplicate at each dilution. (Panel C) The absorbance for anti-Ad antibodies in an ELISA of GAA-KO mouse plasma for the same samples as described for the ELISA for anti-hGAA antibodies above, except that only 2 untreated controls were analyzed. Each sample was analyzed in duplicate at each dilution. The order of loading was the same as in FIG. 1 Panel B.

FIG. 6. hGAA synthesis (top panel) and glycogen content (lower panel) in muscle of GAA-KO/SCID mice administered an AAV2/6 (AAV6) vector expressing GAA intramuscularly.

FIG. 8A-8B. A full-length hGAA cDNA sequence; Genebank Accession No. NM_000152 (SEQ ID NO:1). The encoded protein is shown in SEQ ID NO:2. The ORF is nt 442 . . . 3300. The GAA 3' UTR sequence is from nt 3301 to 3846, total 546 bp.

FIG. 9A-9B. A hGAA sequence with a deleted 3' UTR (SEQ ID NO:3). The 411 bp from nt 3397 through to nt 3807 in the 3' UTR of the sequence shown in FIG. 8A-8B (SEQ ID NO:1) were deleted (bold italic). Note that the polyA signal (bold, 3825 . . . 3830) and polyA site (3846) are not deleted. The 5' UTR sequence of nt 1 through nt 409 was also deleted.

DETAILED DESCRIPTION OF THE PREFERRED EMBODIMENTS

Figure 1:
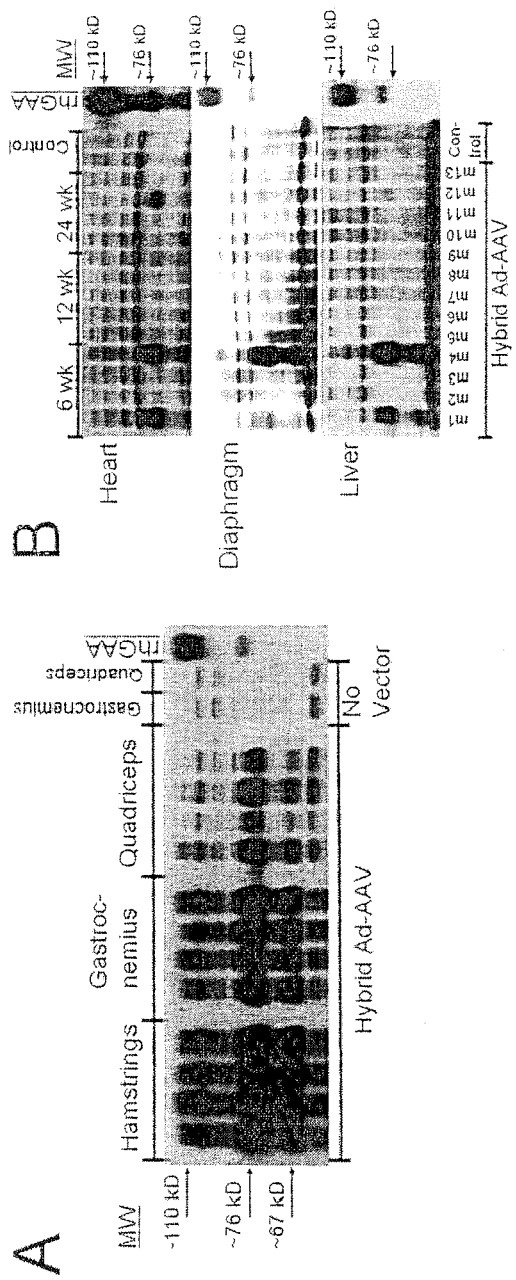
FIG. 1. Detection of hGAA following neonatal intramuscular administration of an Ad-AAV vector in GAA-KO mice. (Panel A) Western blot analysis of muscle after gastrocnemius of GAA-KO mice was injected with the Ad-AAV vector ($4 \times 10^{10}$ DRP) encoding hGAA at 3 days of age. All samples were obtained 24 weeks following vector administration. Recombinant human GAA (rhGAA) was the standard. Each lane for the indicated muscle groups represents one GAA-KO mouse. The ~67 kD, ~76 kD, and ~110 kD hGAA species were detected in transduced muscle as expected (Amalfitano, A., et al. (1999) *Proc. Natl. Acad. Sci. USA* 96:8861-8866, Ding, E., et al., (2002) Mol. Ther. 5:436-446). (Panel B) Western blot analysis of heart, liver and diaphragm following neonatal administration of the Ad-AAV vector. Each lane represents one GAA-KO mouse analyzed at the indicated time following vector administration. The samples for individual mice were loaded in the same order for the Western blot of each tissue.

The present invention is based, in part, on the discovery of improved nucleic acid constructs for expressing lysosomal polypeptides such as GAA. One aspect of the invention provides an isolated nucleic acid encoding a chimeric polypeptide comprising a lysosomal polypeptide operably linked to a secretory signal sequence such that targeting of the lysosomal polypeptide to the secretory pathway (i.e., instead of to the lysosome) is enhanced. As another aspect, the invention encompasses isolated nucleic acids comprising a coding sequence for GAA and an "abbreviated" 3' UTR.

The isolated nucleic acids of the invention are advantageous for delivery of lysosomal polypeptides (e.g., GAA) to target cells or for recombinant protein production in cultured cells or tissues or whole animal systems (e.g., for enzyme replacement therapy). In particular embodiments, the present invention can be practiced to deliver a coding sequence for a lysosomal polypeptide to a "depot" tissue or organ (e.g., liver, skeletal muscle, lung), where the polypeptide is expressed in the depot tissue or organ, secreted into the systemic circulation, and taken up by target tissues (e.g., skeletal muscle, cardiac muscle and/or diaphragm muscle in GAA deficient individuals). In representative embodiments, uptake of GAA polypeptide secreted from the liver by skeletal muscle and/or other tissues affected by GAA deficiency results in a reduction in glycogen stores or improvement in other clinical indicia of GAA deficiency. In other embodiments, the isolated nucleic acid is delivered to cells (e.g., neurons and/or glial cells) in the brain, the lysosomal polypeptide is produced and secreted by the transformed or transduced cells and taken up by other brain cells.

The present invention will now be described with reference to the accompanying drawings, in which preferred embodiments of the invention are shown. The terminology used in the description of the invention herein is for the purpose of describing particular embodiments only and is not intended to be limiting of the invention. This invention may be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment may be incorporated into other embodiments, and features illustrated with respect to a particular embodiment may be deleted from that embodiment. In addition, numerous variations and additions to the embodiments suggested herein will be apparent to those skilled in the art in light of the instant disclosure, which do not depart from the instant invention.

Unless otherwise defined, all technical and scientific terms used herein have the same meaning as commonly understood by one of ordinary skill in the art to which this invention belongs.

All publications, patent applications, patents, and other references mentioned herein are incorporated by reference in their entirety.

Except as otherwise indicated, standard methods may be used for the production of viral and non-viral vectors, manipulation of nucleic acid sequences, production of transformed cells, recombinant protein production, and the like according to the present invention. Such techniques are known to those skilled in the art. See, e.g., SAMBROOK et al., MOLECULAR CLONING: A LABORATORY MANUAL 2nd Ed. (Cold Spring Harbor, N.Y., 1989); F. M. AUSUBEL et al. CURRENT PROTOCOLS IN MOLECULAR BIOLOGY (Green Publishing Associates, Inc. and John Wiley & Sons, Inc., New York).

Definitions

Unless indicated otherwise, explicitly or by context, the following terms are used herein as set forth below:

As used in the description of the invention and the appended claims, the singular forms "a," "an" and "the" are intended to include the plural forms as well, unless the context clearly indicates otherwise.

As used herein, a "vector" or "delivery vector" may be a viral or non-viral vector that is used to deliver a nucleic acid to a cell, tissue or subject.

A "recombinant" vector or delivery vector refers to a viral or non-viral vector that comprises one or more heterologous nucleoli sequences (i.e., transgenes), e.g., two, three, four, five or more heterologous nucleotide sequences. The recombinant vectors of the invention comprise nucleotide sequences that encode GAA, but may also comprise one or more additional heterologous sequences.

As used herein, the term "viral vector" or "viral delivery vector" may refer to a virus particle that functions as a nucleic acid delivery vehicle, and which comprises the recombinant vector genome packaged within a virion. Alternatively, these terms may be used to refer to the vector genome when used as a nucleic acid delivery vehicle in the absence of the virion.

A viral "vector genome" refers to the viral genomic DNA or RNA, in either its naturally occurring or modified form. A "recombinant vector genome" is a viral genome (e.g., vDNA) that comprises one or more heterologous nucleotide sequence(s).

A "heterologous nucleotide sequence" will typically be a sequence that is not naturally-occurring in the vector. Alternatively, a heterologous nucleotide sequence may refer to a sequence that is placed into a non-naturally occurring environment (e.g., by association with a promoter with which it is not naturally associated).

By "infectious," as used herein, it is meant that a virus can enter a cell by natural transduction mechanisms and express viral genes (including heterologous nucleotide sequence(s)). Alternatively, an "infectious" virus is one that can enter the cell by other mechanisms and express the genes encoded by the viral genome. As one illustrative example, the vector can enter a target cell by expressing a ligand or binding protein for a cell-surface receptor in the virion or by using an antibody(ies) directed against molecules on the cell-surface followed by internalization of the complex.

As used herein, "transduction" of a cell by AAV means that the AAV enters the cell to establish a latent infection. See, e.g., BERNARD N. FIELDS et al., VIROLOGY, volume 2, chapter 69 (3d ed., Lippincott-Raven Publishers).

The term "replication" as used herein in reference to viral vectors refers specifically to replication (i.e., making new copies of) of the vector genome (i.e., virion DNA or RNA).

The term "propagation" as used herein in reference to viral vectors refers to a productive viral infection wherein the viral genome is replicated and packaged to produce new virions, which typically can "spread" by infection of cells beyond the initially infected cell. A "propagation-defective" virus is impaired in its ability to produce a productive viral infection and spread beyond the initially infected cell.

As used herein, the term "polypeptide" encompasses both peptides and proteins, unless indicated otherwise.

A "chimeric polypeptide" is a polypeptide produced when two heterologous genes or fragments thereof coding for two (or more) different polypeptides or fragments thereof not found fused together in nature are fused together in the correct translational reading frame. Illustrative chimeric polypeptides include fusions of GAA or other lysosomal polypeptides to all or a portion of glutathione-S-transferase, maltose-binding protein, or a reporter protein (e.g., Green Fluorescent Protein, β-glucuronidase, and β-galactosidase, luciferase). In particular embodiments of the invention, the chimeric polypeptide comprises a secretory signal sequence operably linked to a lysosomal polypeptide (e.g., GAA).

As used herein, a "functional" polypeptide is one that retains at least one biological activity normally associated with that polypeptide. Preferably, a "functional" polypeptide retains all of the activities possessed by the unmodified polypeptide. By "retains" biological activity, it is meant that the polypeptide retains at least about 50%, 60%, 75%, 85%, 90%, 95%, 97%, 98%, 99%, or more, of the biological activity of the native polypeptide (and may even have a higher level of activity than the native polypeptide). A "non-functional" polypeptide is one that exhibits essentially no detectable biological activity normally associated with the polypeptide (e.g., at most, only an insignificant amount, e.g., less than about 10% or even 5%).

As used herein, an "isolated" nucleic acid (e.g., an "isolated DNA" or an "isolated vector genome") means a nucleic acid separated or substantially free from at least some of the other components of the naturally occurring organism or virus, for example, the cell or viral structural components or other polypeptides or nucleic acids commonly found associated with the nucleic acid.

Likewise, an "isolated" polypeptide means a polypeptide that is separated or substantially free from at least some of the other components of the naturally occurring organism or virus, for example, the cell or viral structural components or other polypeptides or nucleic acids commonly found associated with the polypeptide.

A "therapeutically effective" amount as used herein is an amount that is sufficient to provide some improvement or benefit to the subject. Alternatively stated, a "therapeutically-effective" amount is an amount that will provide some alleviation, mitigation or decrease in at least one clinical symptom in the subject. To illustrate, in the case of GAA deficiency, an amount that provides some alleviation, mitigation or decrease in at least one clinical symptom of GAA deficiency (e.g., reduced glycogen stores in skeletal, diaphragm and/or cardiac muscle, improved muscle strength and function, improved pulmonary function, improved motor development or attainment of motor developmental milestones, reduction in need for or prevention of need for ventilator support, prevention of cardiac or cardiorespiratory failure, reduced premature mortality, and the like). Those skilled in the art will appreciate that the therapeutic effects need not be complete or curative, as long ad some benefit is provided to the subject.

By the terms "treating" or "treatment of," it is intended that the severity of the patient's condition is reduced or at least partially improved and that some alleviation, mitigation, delay or decrease in at least one clinical symptom is achieved.

A "reduction in glycogen stores" in a tissue is intended to indicate about a 25%, 35%, 40%, 50%, 60%, 75%, 85%, 90% 95% or more reduction in total glycogen in a particular tissue, unless otherwise indicated (e.g., a reduction in lysosomal glycogen stores or in pooled tissues).

By the term "express" or "expression" of a nucleic acid coding sequence, in particular a GAA coding sequence, it is meant that the sequence is transcribed, and optionally, translated. Generally, however, according to the present invention, the term "express" or "expression" is intended to refer to transcription and translation of the coding sequence resulting in production of the encoded polypeptide.

By "enhanced" or "enhancement" (or grammatical variations thereof) with respect to nucleic acid expression or polypeptide production, it is meant an increase and/or prolongation of steady-state levels of the indicated nucleic acid or polypeptide, e.g., by at least about 20%, 25%, 40%, 50%, 60%, 75%, 2-fold, 2.5-fold, 3-fold, 5-fold, 10-fold, 15-fold, 20-fold, 30-fold, 50-fold, 100-fold or more.

Unless indicated otherwise, the terms "enhanced" or "enhancement" (or grammatical variations thereof) with respect to polypeptide secretion indicates an increase in the relative proportion of polypeptide that is secreted from the cell, e.g., by at least about 20%, 25%, 40%, 50%, 60%, 75%, 2-fold, 2.5-fold, 3-fold, 5-fold, 10-fold, 15-fold, 20-fold, 30-fold, 50-fold, 100-fold or more.

II. Improved Constructs for Producing Lysosomal Polypeptides.

As described in more detail below, the present invention provides improved constructs for producing lysosomal polypeptides, e.g., polypeptides that are targeted to the lysosomes. As known in the art, many lysosomal proteins are characterized by the presence of mannose-6-phosphate residues, and in embodiments of the invention the lysosomal polypeptide comprises mannose-6-phosphate glycosylation. In other representative embodiments, the lysosomal polypeptide is one that is associated with a lysosomal storage disease (e.g., because of a deficiency or defect in the lysosomal polypeptide). By "associated with a lysosomal storage disease", it is meant that the lysosomal polypeptide is one that is deficient or defective in a lysosomal storage disorder, or is otherwise a causative agent in a lysosomal storage disorder.

As known in the art, there are a multitude of lysosomal storage diseases. Exemplary lysosomal storage disease include, but are not limited to, glycogen storage disease type II (GSD II or Pompe Disease), GM1 gangliosidosis, Tay-Sachs disease, GM2 gangliosidosis (AB variant), Sandhoff disease, Fabry disease, Gaucher disease, metachromatic leukodystrophy, Krabbe disease, Niemann-Pick disease (Types A-D), Farber disease, Wolman disease, Hurler Syndrome (MPS III), Scheie Syndrome (MPS IS), Hurler-Scheie Syndrome (MPS IH/S), Hunter Syndrome (MPS II), Sanfilippo A Syndrome (MPS IIIA), Sanfilippo B Syndrome (MPS IIIB), Sanfilippo C Syndrome (MPS IIIC), Sanfilippo D Syndrome (MPS IIID), Morquio A disease (MPS IVA), Morquio B disease (MPS IV B), Maroteaux-Lamy disease (MPS VI), Sly Syndrome (MPS VII), α-mannosidosis, β-mannosidosis, fucosidosis, aspartylglucosaminuria, sialidosis (mucolipidosis I), mucolipidosis II (I-Cell disease), mucolipidosis III (pseudo-Hurler polydystrophy), mucolipidosis IV, galactosialidosis (Goldberg Syndrome), Schindler disease, cystinosis, Salla disease, infantile sialic acid storage disease, Batten disease (juvenile neuronal ceroid lipofuscinosis), infantile neuronal ceroid lipofuscinosis, and prosaposin.

Lysosomal polypeptides that are associated with lysosomal storage diseases according to the present invention include, but are not limited to, lysosomal acid α-glucosidase (GAA; also known as acid maltase), α-galactosidase A, β-galactosidase, β-hexosaminidase A, β-hexosaminidase B, $GM_2$ activator protein, glucocerebrosidase, arylsulfatase A, galactosylceramidase, acid sphingomyelinase, acid ceramidase, acid lipase, α-L-iduronidase, iduronate sulfatase, heparan N-sulfatase, α-N-acetylglucosaminidase, glucosaminide acetyltransferase, N-acetylglucosamine-6-sulfatase, arylsulfatase B, β-glucuronidase, α-mannosidase, β-mannosidase, α-L-fucosidase, N-aspartyl-β-glucosaminidase, N-acetylgalactosamine 4-sulfatase, α-neuraminidase, lysosomal protective protein, α-N-acetyl-galactosaminidase, N-acetylglucosamine-1-phosphotransferase, cystine transport protein, sialic acid transport protein, the CLN3 gene product, palmitoyl-protein thioesterase, saposin A, saposin B, saposin C, and saposin D.

Lysosomal acid α-glucosidase or "GAA" (E.C. 3.2.1.20) (1,4-α-D-glucan glucohydrolase), is an exo-1,4-α-D-glucosidase that hydrolyses both α-1,4 and α-1,6 linkages of oligosaccharides to liberate glucose. A deficiency in GAA results in glycogen storage disease type II (GSDII), also referred to as Pompe disease (although this term formally refers to the infantile onset form of the disease). It catalyzes the complete degradation of glycogen with slowing at branching points. The 28 kb human acid α-glucosidase gene on chromosome 17 encodes a 3.6 kb mRNA which produces a 951 amino acid polypeptide (Hoefsloot et al., (1988) EMBO J. 7:1697; Martiniuk et al., (1990) DNA and Cell Biology 9:85). The enzyme receives co-translational N-linked glycosylation in the endoplasmic reticulum. It is synthesized as a 110-kDa precursor form, which matures by extensive glycosylation modification, phosphorylation and by proteolytic processing through an approximately 90-kDa endosomal intermediate into the final lysosomal 76 and 67 kDa forms (Hoefsloot, (1988) EMBO J. 7:1697; Hoefsloot et al., (1990) Biochem. J. 272:485; Wisselaar et al., (1993) J. Biol. Chem. 268:2223; Hermans et al., (1993) Biochem. J. 289:681).

In patients with GSD II, a deficiency of acid α-glucosidase causes massive accumulation of glycogen in lysosomes, disrupting cellular function (Hirschhorn, R. and Reuser, A. J. (2001), in The Metabolic and Molecular Basis for Inherited Disease, (eds, Scriver, C. R. et al.) pages 3389-3419 (McGraw-Hill, New York). In the most common infantile form, patients exhibit progressive muscle degeneration and cardiomyopathy and die before two years of age. Severe debilitation is present in the juvenile and adult onset forms.

The term "GAA" or "GAA polypeptide," as used herein, encompasses mature (~76 or ~67 kDa) and precursor (e.g., ~110 kDa) GAA as well as modified (e.g., truncated or mutated by insertion(s), deletion(s) and/or substitution(s)) GAA proteins or fragments thereof that retain biological function (i.e., have at least one biological activity of the native GAA protein, e.g., can hydrolyze glycogen, as defined above) and GAA variants (e.g., GAA II as described by Kunita et al., (1997) Biochemica et Biophysica Acta 1362:269; GAA polymorphisms and SNPs are described by Hirschhorn, R. and Reuser, A. J. (2001) in The Metabolic and Molecular Basis for Inherited Disease (Scriver, C. R., Beaudet. A. L., Sly, W. S. & Valle, D. Eds.), pp. 3389-3419, McGraw-Hill, New York, see pages 3403-3405; each incorporated herein by reference in its entirety). Any GAA coding sequence known in the art may be used, for example, see the coding sequences of FIGS. 8 and 9; GenBank Accession number NM_00152 and Hoefsloot et al., (1988) EMBO J. 7:1697 and Van Hove et al., (1996) Proc. Natl. Acad. Sci. USA 93:65 (human), GenBank Accession number NM_008064 (mouse), and Kunita et al., (1997) Biochemica et Biophysics Acta 1362:269 (quail); the disclosures of which are incorporated herein by reference for their teachings of GAA coding and noncoding sequences.

Likewise, the term "lysosomal polypeptide," as used herein, encompasses mature and precursor lysosomal polypeptides as well as modified (e.g., truncated or mutated by insertion(s), deletion(s) and/or substitution(s)) lysosomal polypeptides or fragments thereof that retain biological function (i.e., have at least one biological activity of the native lysosomal polypeptide) and lysosomal polypeptide variants.

The coding sequence of the lysosomal polypeptide can be derived from any source, including avian and mammalian species. The term "avian" as used herein includes, but is not limited to, chickens, ducks, geese, quail, turkeys and pheasants. The term "mammal" as used herein includes, but is not limited to, humans, simians and other non-human primates, bovines, ovines, caprines, equines, felines, canines, lagomorphs, etc. In embodiments of the invention, the nucleic acids of the invention encode a human, mouse or quail lysosomal polypeptide.

A. Constructs for Targeting Lysosomal Polypeptides to the Secretory Pathway.

Lysosomal proteins generally have amino-terminal signal peptides that co-translationally transfer the nascent proteins to the lumen of the endoplasmic reticulum. It is believed that lysosomal polypeptides diverge from the secretory pathway and are directed to the lysosome by at least three distinct pathways (see, e.g., Wisselaar et al., (1993) J. Biol. Chem. 268:2223-31). The best studied of these involves the post-translational addition of mannose-6-phosphate residues that are recognized by the phosphomannosyl receptor, which directs the transport of the polypeptide to the lysosome.

The first 27 amino acids of the human GAA polypeptide are typical of signal peptides of lysosomal and secretory proteins. GAA may be targeted to lysosomes via the phosphomannosyl receptor and/or by sequences associated with the delayed cleavage of the signal peptide (Hirschhorn, R. and Reuser, A. J. (2001), in The Metabolic and Molecular Basis for Inherited Disease, (eds, Scriver, C. R. et al.) pages 3389-3419 (McGraw-Hill, New York). A membrane-bound precursor form of the enzyme (i.e., anchored by the uncleaved signal peptide) has been identified in the lumen of the endoplasmic reticulum (see, e.g., Wisselaar et al., (1993) J. Biol. Chem. 268:2223-31).

The present invention provides isolated nucleic acids encoding lysosomal polypeptides (e.g., GAA) that are fused to a signal peptide that enhances targeting of the polypeptide to the secretory pathway. Secretion of lysosomal polypeptides from the cell provides a number of advantages. For example, in recombinant protein production systems (both cultured cells/tissues or whole animals systems), it is generally preferable to purify a secreted polypeptide from the extracellular medium or fluids rather than harvesting the cells and isolating intracellular protein. With respect to therapeutic methods, it has been shown that administration of an Ad vector encoding hGAA that was targeted to liver in a GAA knock-out mouse model reversed glycogen accumulation in skeletal and cardiac muscle by secretion of hGAA from the liver and uptake by affected tissues (Amalfitano et al., Proc. Natl. Acad. Sci. USA 96:8861-8866). Presumably, secretion of significant amounts of GAA (i.e., rather than lysosomal targeting) was a result of over-expression of the GAA transgene delivered by the Ad vector and saturation of the "scavenger" system that normally redirects extracellular lysosomal proteins to the lysosome.

The present invention advantageously provides improved constructs that enhance secretion of lysosomal polypeptides from the transduced or transfected cell. These constructs facilitate the use of alternative delivery systems (e.g., AAV vectors for liver delivery), enhance the secretion of lysosomal polypeptides (e.g., for in vivo gene delivery or in vitro enzyme production), and can reduce or avoid cytotoxicity or organ toxicity (e.g., hepatotoxicity) that may result from over-accumulation of recombinant protein in the depot organ.

Accordingly, the invention encompasses isolated nucleic acids encoding a chimeric polypeptide comprising a secretory signal sequence operably linked to a lysosomal polypeptide (e.g., GAA) as well as the chimeric polypeptides. The secretory signal sequence is foreign to (e.g., exogenous to) the lysosomal polypeptide. While those skilled in the art will appreciate that secretory signal sequences are typically at the amino-terminus of the nascent polypeptide, the secretory signal sequence according to the present invention can be located at any position within the chimeric polypeptide (e.g., N-terminal, within the mature polypeptide, or C-terminal) as long as it functions as a secretory signal sequence (e.g., enhances secretion of the lysosomal polypeptide) and does not render the lysosomal polypeptide non-functional.

As used herein, the term "secretory signal sequence" or variations thereof are intended to refer to amino acid sequences that function to enhance (as defined above) secretion of an operably linked lysosomal polypeptide from the cell as compared with the level of secretion seen with the native lysosomal polypeptide. As defined above, by "enhanced" secretion, it is meant that the relative proportion of lysosomal polypeptide synthesized by the cell that is secreted from the cell is increased; it is not necessary that the absolute amount of secreted protein is also increased. In particular embodiments of the invention, essentially all (i.e., at least 95%, 97%, 98%, 99% or more) of the polypeptide is secreted. It is not necessary, however, that essentially all or even most of the lysosomal polypeptide is secreted, as long as the level of secretion is enhanced as compared with the native lysosomal polypeptide.

In particular embodiments, at least about 50%, 60%, 75%, 85%, 90%, 95%, 98% or more of the lysosomal polypeptide is secreted from the cell.

The relative proportion of newly-synthesized lysosomal polypeptide that is secreted from the cell can be routinely determined by methods known in the art and as described in the Examples. Secreted proteins can be detected by directly measuring the protein itself (e.g., by Western blot) or by protein activity assays (e.g., enzyme assays) in cell culture medium, serum, milk, etc.

Generally, secretory signal sequences are cleaved within the endoplasmic reticulum and, in particular embodiments of the invention, the secretory signal sequence is cleaved prior to secretion. It is not necessary, however, that the secretory signal sequence is cleaved as long as secretion of the lysosomal polypeptide from the cell is enhanced and the lysosomal polypeptide is functional. Thus, in embodiments of the invention, the secretory signal sequence is partially or entirely retained.

Thus, in particular embodiments of the invention, an isolated nucleic acid encoding a chimeric polypeptide comprising a lysosomal polypeptide operably linked to a secretory signal sequence is delivered to a cell, and the chimeric polypeptide is produced and the lysosomal polypeptide secreted from the cell. The lysosomal polypeptide can be secreted after cleavage of all or part of the secretory signal sequence. Alternatively, the lysosomal polypeptide can retain the secretory signal sequence (i.e., the secretory signal is not cleaved). Thus, in this context, the "lysosomal polypeptide" can be a chimeric polypeptide.

Those skilled in the art will further understand that the chimeric polypeptide can contain additional amino acids, e.g., as a result of manipulations of the nucleic acid construct such as the addition of a restriction site, as long as these additional amino acids do not render the secretory signal sequence or the lysosomal polypeptide non-functional. The additional amino acids can be cleaved or can be retained by the mature polypeptide as long as retention does not result in a nonfunctional polypeptide.

In representative embodiments, the secretory signal peptide replaces most, essentially all or all of the leader sequence found in the native lysosomal polypeptide. In particular embodiments, most or all of the native leader sequence is retained, as long as secretion of the lysosomal polypeptide is enhanced and the mature lysosomal polypeptide is functional.

The secretory signal sequence can be derived in whole or in part from the secretory signal of a secreted polypeptide (i.e., from the precursor) and/or can be in whole or in part synthetic. The secretory signal sequence can be from any species of origin, including animals (e.g., avians and mammals such as humans, simians and other non-human primates, bovines, ovines, caprines, equines, porcines, canines, felines, rats, mice, lagomorphs), plants, yeast, bacteria, protozoa or fungi. The length of the secretory signal sequence is not critical; generally, known secretory signal sequences are from about 10-15 to 50-60 amino acids in length. Further, known secretory signals from secreted polypeptides can be altered or modified (e.g., by substitution, deletion, truncation or insertion of amino acids) as long as the resulting secretory signal sequence functions to enhance secretion of an operably linked lysosomal polypeptide.

The secretory signal sequences of the invention can comprise, consist essentially of or consist of a naturally occurring secretory signal sequence or a modification thereof (as described above). Numerous secreted proteins and sequences that direct secretion from the cell are known in the art. Exemplary secreted proteins (and their secretory signals) include but are not limited to: erythropoietin, coagulation Factor IX, cystatin, lactotransferrin, plasma protease C1 inhibitor, apolipoproteins (e.g., APO A, C, E), MCP-1, $\alpha$-2-HS-glycoprotein, $\alpha$-1-microgolubilin, complement (e.g., C1Q, C3), vitronectin, lymphotoxin-$\alpha$, azurocidin, VIP, metalloproteinase inhibitor 2, glypican-1, pancreatic hormone, clusterin, hepatocyte growth factor, insulin, $\alpha$-1-antichymotrypsin, growth hormone, type IV collagenase, guanylin, properdin, proenkephalin A, inhibin $\beta$ (e.g., A chain), prealbumin, angiocenin, lutropin (e.g., $\beta$ chain), insulin-like growth factor binding protein 1 and 2, proactivator polypeptide, fibrinogen (e.g., $\beta$ chain), gastric triacylglycerol lipase, midkine, neutrophil defensins 1, 2, and 3, $\alpha$-1-antitrypsin, matrix gla-protein, $\alpha$-tryptase, bile-salt-activated lipase, chymotrypsinogen B, elastin, IG lambda chain V region, platelet factor 4 variant, chromogranin A, WNT-1 proto-oncogene protein, oncostatin M, $\beta$-neoendorphin-dynorphin, von Willebrand factor, plasma serine protease inhibitor, serum amyloid A protein, nidogen, fibronectin, rennin, osteonectin, histatin 3, phospholipase A2, cartilage matrix Protein, GM-CSF, matrilysin, neuroendocrine protein 7B2, placental protein 11, gelsolin, IGF 1 and 2, M-CSF, transcobalamin I, lactase-phlorizin hydrolase, elastase 2B, pepsinogen A, MIP 1-$\beta$, prolactin, trypsinogen II, gastrin-releasing peptide II, atrial natriuretic factor, secreted alkaline phosphatase, pancreatic $\alpha$-amylase, secretogranin I, $\beta$-casein, serotransferrin, tissue factor pathway inhibitor, follitropin $\beta$-chain, coagulation factor XII, growth hormone-releasing factor, prostate seminal plasma protein, interleukins (e.g., 2, 3, 4, 5, 9, 11), inhibin (e.g., alpha chain), angiotensinogen, thyroglobulin, IG heavy or light chains, plasminogen activator inhibitor-1, lysozyme C, plasminogen activator, antileukoproteinase 1, statherin, fibulin-1, isoform B, uromodulin, thyroxine-binding globulin, axonin-1, endometrial $\alpha$-2 globulin, interferon (e.g., alpha, beta, gamma), $\beta$-2-microglobulin, procholecystokinin, progastricsin, prostatic acid phosphatase, bone sialoprotein II, colipase, Alzheimer's amyloid A4 protein, PDGF (e.g., A or B chain), coagulation factor V, triacylglycerol lipase, haptoglobuin-2, corticosteroid-binding globulin, triacylglycerol lipase, prorelaxin H2, follistatin 1 and 2, platelet glycoprotein IX, GCSF, VEGF, heparin cofactor II, antithrombin-III, leukemia inhibitory factor, interstitial collagenase, pleiotrophin, small inducible cytokine A1, melanin-concentrating hormone, angiotensin-converting enzyme, pancreatic trypsin inhibitor, coagulation factor VIII, $\alpha$-fetoprotein, $\alpha$-lactalbumin, senogelin II, kappa casein, glucagon, thyrotropin beta chain, transcobalamin II, thrombospondin 1, parathyroid hormone, vasopressin copeptin, tissue factor, motilin, MPIF-1, kininogen, neuroendocrine convertase 2, stem cell factor procollagen $\alpha$1 chain, plasma kallikrein keratinocyte growth factor, as well as any other secreted hormone, growth factor, cytokine, enzyme, coagulation factor, milk protein, immunoglobulin chain, and the like.

In other particular embodiments, the secretory signal sequence is derived in part or in whole from a secreted polypeptide that is produced by liver cells.

The secretory signal sequence of the invention can further be in whole or in part synthetic or artificial. Synthetic or artificial secretory signal peptides are known in the art, see e.g., Barash et al., "Human secretory signal peptide description by hidden Markov model and generation of a strong artificial signal peptide for secreted protein expression," *Biochem. Biophys. Res. Comm.* 294:835-42 (2002); the disclosure of which is incorporated herein in its entirety. In particular embodiments, the secretory signal sequence comprises, consists essentially of, or consists of the artificial secretory signal: MWWRLWWLLLLLLLLWPMVWA (SEQ ID NO: 5) or variations thereof having 1, 2, 3, 4, or 5 amino acid substitutions (optionally, conservative amino acid substitutions, conservative amino acid substitutions are known in the art).

The isolated nucleic acid encoding the chimeric polypeptide can further comprise an "abbreviated" 3' UTR as described in more detail below.

B. "Abbreviated" GAA Constructs.

The present invention is based, in part, on the discovery that constructs expressing lysosomal acid α-glucosidase (GAA) that are deleted or altered (e.g., substituted) in the 3' untranslated region (UTR), can have advantageous properties as compared with non-deleted or non-altered constructs. For example, the efficiency of packaging a 3' UTR deleted or otherwise "abbreviated" 3' UTR GAA construct (as discussed in more detail below) into viral vectors (e.g., AAV vectors) can be improved. Further, the level of expression of the GAA mRNA and/or polypeptide can be enhanced (e.g., as a result of a higher level of transcription and/or translation and/or longer half-life of the mRNA transcript and/or polypeptide) as compared with a full-length construct (e.g., SEQ ID NO:1, FIG. 8).

The present invention provides isolated nucleic acids encoding GAA, comprising a coding, sequence for GAA and an "abbreviated" 3' untranslated region (UTR). The "abbreviated" 3' UTR are altered as compared with the native GAA 3' UTR sequence (e.g., the 3' UTR of SEQ ID NO:1 is from nt 3301 through 3846; see also FIG. 8). In representative embodiments, the abbreviated 3' UTR comprises, consists essentially of or consists of a deleted GAA 3' UTR. In other embodiments, the abbreviated 3' UTR is shortened as compared with the native GAA 3' UTR and has been altered to contain a region from a heterologous 3' UTR, which can be a partially or wholly synthetic 3' UTR sequence. These embodiments of the invention are discussed in more detail below. The isolated nucleic acids encoding GAA and comprising an abbreviated 3' UTR of the invention can provide for higher levels of GAA polypeptide expression. In particular embodiments, the abbreviated constructs can also be more efficiently packaged into viral vectors (e.g., rAAV vectors).

The abbreviated 3' UTR of the invention encode functional 3' UTR that, in the presence of all other necessary regulatory elements, permit the expression of a functional GAA polypeptide from a GAA coding sequence operably associated therewith. In illustrative embodiments, the isolated nucleic acid comprising a coding sequence for GAA and an abbreviated 3' UTR further comprises a secretory signal sequence operably linked to the GAA coding sequence, as described hereinabove.

While not wishing to be held to any particular theory of the invention, the improved properties of "abbreviated" 3' UTR nucleic acids encoding GAA may be a result of their shorter total size and/or removal of an inhibitory region, e.g., a region that reduces transcription, destabilizes the mRNA transcript and/or inhibits translation. Examples of small sequences that destabilize mRNA for cytokines (see, e.g., Shaw and Kamen, (1986) *Cell* 46:659-67; Reeves et al., (1987) *Proc. Natl. Acad. Sci. USA* 84:6531-35) and the HIV gag gene (see, e.g., Schwartz et al. (1992) *J. Virology* 66:150-59; Schwartz et al., (1992) *J. Virol.* 66:7175-82) have been described.

In particular embodiments, the isolated nucleic acid comprising the GAA coding sequence and abbreviated 3' UTR is less than about 4.5, 4.4, 4.3, 4.2, 4.1, 4, 3.9 or 3.8 kb in length. To illustrate, according to representative embodiments, a GAA expression construct including 5' and 3' UTR sequences is less than about 4.5, 4.4, 4.3, 4.2, 4.1, 4, 3.9 or 3.8 kb in length.

The isolated nucleic acid encoding GAA can further comprise a 5' UTR, which can further include all or a portion of the 5' UTR of a GAA gene. Human GAA sequences with deletions in the 5' UTR have been described, see, e.g., Van Hove et al. (1996) *Proc. Natl. Acad. Sci. USA* 93:65, in which nt 1-409 of the 5' UTR of SEQ ID NO:1 (FIG. 8) have been deleted (see also SEQ ID NO:3; FIG. 9). Alternatively, the 5' UTR can be derived in whole or in part from a heterologous gene (i.e., a gene other than a GAA gene) and/or can comprise in whole or in part synthetic sequences.

As one aspect, the present invention provides isolated nucleic acids that encode GAA, where the isolated nucleic acid comprises (i) a GAA coding sequence encoding a GAA and (ii) a GAA 3' UTR region having a deletion therein.

A "coding region encoding a GAA polypeptide" comprises nucleotide sequences that can be transcribed and translated to yield a functional GAA polypeptide or functional fragment thereof (see above). Such coding sequences may include non-translated sequences (e.g., intron sequences).

A "GAA 3' UTR region" refers to the non-translated nucleic acid sequences of a GAA gene that are located downstream of (i.e., 3' to) the regions of the gene that encode the GAA protein.

By "deleted" GAA 3' UTR, it is intended that there is an omission of at least one nucleotide from the 3' UTR region of the GAA expression construct. Deletions can be greater than about 25, 50, 100, 150, 200, 300, 400 consecutive nucleotides, or more. In particular embodiments, essentially all of the 3' UTR is deleted. By "essentially all" it is meant that only an insignificant fragment of the intact 3' UTR remains (i.e., less than 10, 20 or 30 nucleotides). For example, essentially all, but not necessarily all, of the 3' UTR can be conveniently removed using restriction enzymes (i.e., there may be some residual nucleotides left after restriction enzyme cleavage) or some untranslated nucleotides may remain 3' of the coding sequence as an artifact of cloning procedures.

Alternatively stated, at least 25%, 50%, 60%, 70%, 80%, 90%, 95%, 99% or more of the GAA 3' UTR can be deleted. As still a further alternative, in embodiments of the invention, the "deleted" GAA 3' UTR is less than about 300, 250, 200, 175, 150, 125, 100, 75, 50, 30, 20 or 10 nucleotides in length or less.

In particular embodiments of the invention, the deleted 3' UTR comprises, consists essentially of or consists of a deleted form of the 3' UTR in the human GAA sequence provided in SEQ ID NO:1 (i.e., the 3' UTR of SEQ ID NO:1 is from nt 3301 through 3846; see also FIG. 8). For example, the deleted 3' UTR can comprise, consist essentially of or consist of the 3' UTR shown in SEQ ID NO:3 (i.e., the 3' UTR of SEQ ID NO:3 is from nt 2878 through 3012; see also, FIG. 9).

Referring to the 3' UTR in the GAA sequence of SEQ ID NO:1 and FIG. 8 (nt 3301 through 3846), the deleted 3 UTR can comprise a deletion from nt 3301 through 3846 of SEQ ID NO:1. The deletion can also encompass from about nt 3400 through nt 3500, nt 3500 through nt 3600, nt 3600 through nt 3700, nt 3700 through nt 3800, nt 3800 through nt3846, nt 3301 through nt 3450, nt 3450 through nt 3600, nt 3600 through nt 3750, nt 3750 through nt 3846, nt 3301 through nt 3500, nt 3400 through nt 3600, nt 3500 through nt 3700, nt 3600 through nt 3800, nt 3700 through nt 3846, nt 3301 through nt 3600, nt 3400 through nt 3700, nt 3500 through nt 3800, nt 3600 through nt 3846, nt 3301 through nt 3700, nt 3400 through nt 3800, nt 3500 through nt 3845, nt 3300 through nt 3800, or nt 3400 through nt 3486.

Deletions can be intermittent, i.e., more than one region of the nucleotide sequence can be deleted to impart the functional improvements described herein. Alternatively, consecutive nucleotides can be deleted. Further, the deletion can be internal or start at either end of the 3' UTR. For example, the 3' UTR sequence can be truncated from the 5' or 3' end of the 3' UTR by 50, 100, 200, 300 or 400 nt or more.

Those skilled in the art will readily appreciate that the deleted and intact (i.e., from which the deleted 3' UTR are derived) GAA 3' UTR regions within the scope of the present invention can deviate from those specifically disclosed herein and that any suitable GAA coding sequence or GAA 3' UTR may be employed. The GAA coding sequences and 3' UTR can contain other alterations such as substitutions or insertions therein. For example, It will be understood that the GAA 3' UTR can contain some heterologous sequence(s) (e.g., the polyA signal may be from another gene, such as the human or bovine growth hormone gene).

In embodiments of the invention, the 3' UTR deleted nucleic acid encoding GAA will hybridize to the 3' UTR deleted nucleic acid sequences specifically disclosed herein (i.e., SEQ ID NO:3) under standard conditions as known by those skilled in the art and encode a functional GAA polypeptide (as defined above).

In other embodiments, the deleted GAA 3' UTR of the invention will hybridize to the deleted GAA 3' UTR sequences specifically disclosed herein (e.g., nt 2878 to 3012 of SEQ ID NO:3) under standard conditions as known by those skilled in the art and permit the expression of a functional GAA polypeptide from a GAA coding sequence operably associated therewith.

In still further embodiments, the coding sequence of the isolated nucleic acid encoding GAA will hybridize to the sequences encoding GAA specifically disclosed herein (e.g., nt 442 to nt 3300 of SEQ ID NO:1) under standard conditions as known by those skilled in the art and encode a functional GAA polypeptide.

For example, hybridization of such sequences can be carried out under conditions of reduced stringency, medium stringency or even stringent conditions (e.g., conditions represented by a wash stringency of 35-40% formamide with 5×Denhardt's solution, 0.5% SDS and 1×SSPE at 37° C.; conditions represented by a wash stringency of 40-45% formamide with 5×Denhardt's solution. 0.5% SDS, and 1×SSPE at 42° C. and conditions represented by a wash stringency of 50% formamide with 5×Denhardt's solution, 0.5% SDS and 1×SSPE at 42° C., respectively) to the sequences specifically disclosed herein. See, e.g., Sambrook et al., *Molecular Cloning, A Laboratory Manual* (2d Ed. 1989) (Cold Spring Harbor Laboratory).

Alternatively stated, in embodiments of the invention, 3' UTR deleted nucleic acid encoding GAA of the invention have at least about 60%, 70%, 80%, 90%, 95%, 97%, 98% or higher nucleotide sequence homology with the isolated nucleic acid sequences specifically disclosed herein (or fragments thereof) and encode a functional GAA protein (mature or precursor forms).

Likewise, in embodiments of the invention, the deleted 3' UTR according to the present invention have at least about 60%, 70%, 80%, 90%, 95%, 97%, 98%, or higher nucleotide sequence homology with the isolated nucleic acid sequences specifically disclosed herein (or fragments thereof) and permit the expression of a functional GAA polypeptide from a GAA coding sequence operably associated therewith.

Further, in embodiments of the invention, the coding region of the isolated nucleic acids encoding GAA of the invention have at least about 60%, 70%, 80%, 90%, 95%, 97%, 98% or higher nucleotide sequence homology with the isolated nucleic acid sequences specifically disclosed herein (or fragments thereof) and encode a functional GAA polypeptide.

It will be appreciated by those skilled in the art that there may be variability in the polynucleotides that encode the GAA proteins of the present invention due to the degeneracy of the genetic code. The degeneracy of the genetic code, which allows different nucleic acid sequences to code for the same polypeptide, is well known in the literature (see Table 1).

TABLE 1

| Amino Acids | | | Codons |
| --- | --- | --- | --- |
| Alanine | Ala | A | GCA GCC GCG GCT |
| Cysteine | Cys | C | TGC TGT |
| Aspartic acid | Asp | D | GAC GAT |
| Glutamic acid | Glu | E | GAA GAG |
| Phenylalanine | Phe | F | TTC TTT |
| Glycine | Gly | G | GGA GGC GGG GGT |
| Histidine | His | H | CAC CAT |
| Isoleucine | Ile | I | ATA ATC ATT |
| Lysine | Lys | K | AAA AAG |
| Leucine | Leu | L | TTA TTG CTA CTC CTG CTT |
| Methionine | Met | M | ATG |
| Asparagine | Asn | N | AAC AAT |
| Proline | Pro | P | CCA CCC CCG CCT |
| Glutamine | Gln | Q | CAA CAG |
| Arginine | Arg | R | AGA AGG CGA CGC CGG CGT |
| Serine | Ser | S | AGC ACT TCA TCC TCG TCT |
| Threonine | Thr | T | ACA ACC ACG ACT |
| Valine | Val | V | GTA GTC GTG GTT |
| Tryptophan | Trp | W | TGG |
| Tyrosine | Tyr | Y | TAC TAT |

Further, in other embodiments, the isolated nucleic acids of the invention encompass those nucleic acids encoding GAA polypeptides that have at least about 60%, 70%, 80%, 90%, 95%, 97%, 98%, 99% or higher amino acid sequence homology with the polypeptide sequences specifically disclosed herein (or fragments thereof) and encode a functional GAA polypeptide.

As is known in the art, a number of different programs can be used to identify whether a nucleic acid or polypeptide has sequence identity or similarity to a known sequence. Sequence identity and/or similarity can be determined using standard techniques known in the art, including, but not limited to, the local sequence identity algorithm of Smith & Waterman, *Adv. Appl. Math.* 2, 482 (1981), by the sequence identity alignment algorithm of Needleman & Wunsch, *J. Mol. Biol.* 48, 443 (1970), by the search for similarity method of Pearson & Lipman, *Proc. Natl. Acad. Sci. USA* 85, 2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., *Nucl. Acid Res.* 12, 387-395 (1984), preferably using the default settings, or by inspection.

An example of a useful algorithm is PILEUP, which creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35, 351-360 (1987); the method is similar to that described by Higgins & Sharp, *CABIOS* 5, 151-153 (1989).

Another example of a useful algorithm is the BLAST algorithm, described in Altschul et al., *J. Mol. Biol.* 215, 403-410, (1990) and Karlin et al., *Proc. Natl. Acad. Sci. USA* 90, 5873-5787 (1993). A particularly useful BLAST program is the WU-BLAST-2 program which was obtained from Altschul et al., *Methods in Enzymology,* 266, 460-480 (1996); http://blast.wustl/edu/blast/README.html. WU-BLAST-2 uses several search parameters, which are preferably set to the default values. The parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al. *Nucleic Acids Res.* 25, 3389-3402.

A percentage amino acid sequence identity value can be determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

The alignment can include the introduction of gaps in the sequences to be aligned. In addition, for sequences which contain either more or fewer amino acids than the polypeptides specifically disclosed herein, it is understood that in one embodiment, the percentage of sequence identity will be determined based on the number of identical amino acids in relation to the total number of amino acids. Thus, for example, sequence identity of sequences shorter than a sequence specifically disclosed herein, will be determined using the number of amino acids in the shorter sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of "0," which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

In a further representative embodiment of the invention, the isolated nucleic acid encoding GAA comprises an abbreviated 3' UTR that is shorter than the 3 UTR found in the native gene (e.g., nt 3301 to nt 3846 of SEQ ID NO:1), to illustrate, is less than about 75%, 50%, 40%, 30%, 20%, 10%, 5%, 4%, or less, of the size of the 3' UTR found in the native GAA gene, and comprises a heterologous region that is substituted for all or a portion of the native 3' UTR. According to this embodiment, all or at least a portion of the 3' UTR is heterologous to the GAA coding region (i.e., is not derived from the 3' UTR of a GAA gene). The heterologous segment can include all or a portion of a 3' UTR of another gene and/or can be partially or completely synthetic. In particular embodiments, the heterologous region can be about 300, 250, 200, 175, 125, 100, 75, 50, 30, 20 or 10 nucleotides in length or less. To illustrate, the substituted 3' UTR can include all or a portion of the bovine or human growth hormone 3' UTR.

According to some embodiments of the invention, the total size of the abbreviated 3' UTR is less than about 300, 250, 200, 175, 150, 125, 100, 75, 50, 30, 20 or 10 nucleotides.

By "substitute," "substituted" or "substitution" in reference to the 3' UTR is meant that a portion of the naturally-occurring nucleotide sequence of the GAA 3' UTR has been replaced by a heterologous nucleotide sequence, resulting in a nucleic acid encoding GAA having the advantages described herein.

According to the present invention, an "abbreviated" 3' UTR encompasses both deleted GAA 3' UTR (described at length above) and the substituted/shortened 3' UTR described in the preceding paragraphs. The abbreviated 3' UTR of the invention may be DNA or RNA, or a chimera thereof.

It still other embodiments of the invention, the "abbreviated" 3' UTR is less than about 300, 250, 200, 150 or 100 nucleotides in length and is derived in whole or in part from a native GAA 3' UTR and/or in whole or in part from a heterologous 3' UTR. Further, the heterologous 3' UTR sequences can be derived from another gene or can be in whole or in part a synthetic sequence.

As described in more detail below, the abbreviated 3' UTR nucleic acids of the invention can, upon introduction into a target cell (e.g., a liver cell), express GAA polypeptide at an enhanced (as defined above) level as compared with a cell expressing GAA polypeptide from a comparable construct that contains a full-length GAA 3' UTR (e.g., SEQ ID NO:1).

III. Nucleic Acid Delivery Vectors.

The methods of the present invention provide a means for delivering and, optionally, expressing lysosomal polypeptides such as GAA in a broad range of host cells, including both dividing and non-dividing cells in vitro or in vivo. In embodiments of the invention, the nucleic acid may be stably introduced into the target cell, for example, by integration into the genome of the cell or by persistent expression from stably maintained episomes (e.g., derived from Epstein Barr Virus). Alternatively, the isolated nucleic acid can be transiently expressed in the cell.

The isolated nucleic acids, vectors, cells, methods and pharmaceutical formulations of the present invention are additionally useful in a method of administering lysosomal polypeptides such as GAA to a subject in need thereof. In this manner, the polypeptide can thus be produced in vivo in the subject. The subject may have a deficiency of the polypeptide, or the production of a foreign polypeptide in the subject may impart some therapeutic effect. Pharmaceutical formulations and methods of delivering lysosomal polypeptides such as GAA for therapeutic purposes are described in more detail in Section V below.

Alternatively, a polynucleotide encoding and expressing the lysosomal polypeptide (e.g., GAA) can be administered to a subject so that the polypeptide is expressed by the subject and purified therefrom, i.e., as a source of recombinant polypeptide. According to this embodiment, it is preferred that the polypeptide is secreted into the systemic circulation or into another body fluid (e.g., milk, lymph, spinal fluid, urine) that is easily collected and from which the polypeptide can be further purified. Alternatively, the polypeptide can be expressed in avian species and deposited in, and conveniently isolated from, egg proteins.

Likewise, the polypeptide can be expressed transiently or stably in a cell culture system. In particular embodiments, the polypeptide is secreted into the medium and can be purified therefrom using routine techniques known in the art. Additionally, or alternatively, the cells can be lysed and the recombinant polypeptide can be purified from the cell lysate. The cell may be a bacterial, protozoan, plant, yeast, fungus, or animal cell. The cell can be an animal cell (e.g., insect, avian or mammalian). Representative mammalian cells include but are not limited to fibroblasts, CHO cells, 293 cells, HT1080 cells, HeLa cells and C10 cells.

in the case of GAA, the recombinant GAA polypeptide can be isolated using standard techniques and administered to subjects with GAA deficiency using enzyme replacement protocols (see, e.g., Van der Ploeg et al., (1991) *J. Clin. Invest.* 87:513).

Transfer of a nucleic acid encoding a lysosomal polypeptide (e.g., GAA) to a cell in culture or to a subject also finds use as a model for understanding disease states such as GSD II and for investigating the biology of these polypeptides.

Still further, the instant invention finds use in screening methods, whereby the polypeptide is transiently or stably expressed in a cell culture system or animal model and used as a target for drug discovery.

Methods of producing lysosomal polypeptides such as GAA in cultured cells or organisms for the purposes described above are set forth in more detail in Section IV below.

It will be apparent to those skilled in the art that any suitable vector may be used to deliver the isolated nucleic acids of the invention to the target cell(s) or subject of interest. The choice of delivery vector may be made based on a number of factors known in the art, including age and species of the target host, in vitro vs. in vivo delivery, level and persistence of expression desired, intended purpose (e.g., for therapy or enzyme production), the target cell or organ, route of delivery, size of the isolated nucleic acid, safety concerns, and the like.

Any suitable vector known in the art can be used to deliver, and optionally, express the isolated nucleic acids of the invention, including, virus vectors (e.g., retrovirus, adenovirus, adeno-associated virus, or herpes simplex virus), lipid vectors, poly-lysine vectors, synthetic polyamino polymer vectors that are used with nucleic acid molecules, such as a plasmid, and the like.

Any viral vector that is known in the art may be used in the present invention. Examples of such viral vectors include, but are not limited to vectors derived from: Adenoviridae; Birnaviridae; Bunyaviridae; Caliciviridae, Capillovirus group; Carlavirus group; Carmovirus virus group; Group Caulimovirus; Closterovirus Group; Commelina yellow mottle virus group; Comovirus virus group; Coronaviridae; PM2 phage group; Corcicoviridae; Group Cryptic virus; group Cryptovirus; Cucumovirus virus group family ([PHgr]6 phage group; Cysioviridae; Group Carnation ringspot; Dianthovirus virus group; Group Broad bean wilt; Fabavirus virus group; Filoviridae; Flaviviridae; Furovirus group; Group Germinivirus; Group Giardiavirus; Hepadnaviridae; Herpesviridae; Hordeivirus virus group; Illarvirus virus group; Inoviridae; Iridoviridae; Leviviridae; Lipothrixviridae; Luteovirus group; Marafivirus virus group; Maize chlorotic dwarf virus group; icroviridae; Myoviridae; Necrovirus group; Nepovirus virus group; Nodaviridae; Orthomyxoviridae; Papovaviridae; Paramyxoviridae; Parsnip yellow fleck virus group; Partitiviridae; Parvoviridae; Pea enation mosaic virus group; Phycodnaviridae; Picornaviridae; Plasmaviridae; Prodoviridae; Polydnaviridae; Potexvirus group; Potyvirus; Poxyiridae; Reoviridae; Retroviridae; Rhabdoviridae; Group Rhizidiovirus; Siphoviridae; Sobemovirus group; SSV 1-Type Phages; Tectiviridae; Tenuivirus; Tetraviridae; Group Tobamovirus; Group Tobravirus; Togaviridae; Group Tombusvirus; Group Torovirus; Totiviridae; Group Tymovirus; and plant virus satellites.

Protocols for producing recombinant viral vectors and for using viral vectors for nucleic acid delivery can be found in *Current Protocols in Molecular Biology*; Ausubel, F. M. et al. (eds.) Greene Publishing Associates; (1989) and other standard laboratory manuals (e.g., Vectors for Gene Therapy, In: *Current Protocols in Human Genetics*, John Wiley and Sons, Inc.; 1997).

Particularly preferred viral vectors are those previously employed for the delivery of transgenes including, for example, retrovirus, adenovirus, AAV, herpes virus, hybrid adenovirus-AAV, and poxvirus vectors. In particular embodiments, the vector is an adenovirus vector, AAV vector or hybrid Ad-AAV vector.

In certain preferred embodiments of the present invention, the delivery vector is an adenovirus vector. The term "adenovirus" as used herein is intended to encompass all adenoviruses, including the *Mastadenovirus* and *Aviadenovirus* genera. To date, at least forty-seven human serotypes of adenoviruses have been identified (see, e.g., FIELDS et al., VIROLOGY, volume 2, chapter 67 (3d ed., Lippincott-Raven Publishers)). Preferably, the adenovirus is a serogroup C adenovirus, still more preferably the adenovirus is serotype 2 (Ad2) or serotype 5 (Ad5).

The various regions of the adenovirus genome have been mapped and are understood by those skilled in the art (see, e.g., FIELDS et al., VIROLOGY, volume 2, chapters 67 and 68 (3d ed., Lippincott-Raven Publishers)). The genomic sequences of the various Ad serotypes, as well as the nucleotide sequence of the particular coding regions of the Ad genome, are known in the art and may be accessed, e.g., from GenBank and NCBI (see, e.g., GenBank Accession Nos. J0917, M73260, X73487, AF108105, L19443, NC 003266 and NCBI Accession Nos. NC 001405, NC 001460, NC 002067, NC 00454).

Those skilled in the art will appreciate that the inventive adenovirus vectors may be modified or "targeted" as described in Douglas et al., (1996) Nature Biotechnology 14:1574; U.S. Pat. No. 5,922,315 to Roy et al.; U.S. Pat. No. 5,770,442 to Wickham et al.; and/or U.S. Pat. No. 5,712,136 to Wickham et al.

An adenovirus vector genome or rAd vector genome will typically comprise the Ad terminal repeat sequences and packaging signal. An "adenovirus particle" or "recombinant adenovirus particle" comprises an adenovirus vector genome or recombinant adenovirus vector genome, respectively, packaged within an adenovirus capsid. Generally, the adenovirus vector genome is most stable at sizes of about 28 kb to 38 kb (approximately 75% to 105% of the native genome size). In the case of an adenovirus vector containing large deletions and a relatively small transgene, "stutter DNA" can be used to maintain the total size of the vector within the desired range by methods known in the art.

Normally adenoviruses bind to a cell surface receptor (CAR) of susceptible cells via the knob domain of the fiber protein on the virus surface. The fiber knob receptor is a 45 kDa cell surface protein which has potential sites for both glycosylation and phosphorylation. (Bergelson, et al., (1997) Science 275:1320-1323. A secondary method of entry for adenovirus is through integrins present on the cell surface. Arginine-Glycine-Aspartic Acid (RGD) sequences of the adenoviral penton base protein bind integrins on the cell surface.

The genome of an adenovirus can be manipulated such that it encodes and expresses a gene product of interest but is inactivated in terms of its ability to replicate in a normal lytic viral life cycle. See, for example. Berkner et al. (1988) BioTechniques 6:616; Rosenfeld et al. (1991) Science 252: 431-434; and Rosenfeld et al. (1992) Cell 68:143-155. Suitable adenoviral vectors derived from the adenovirus strain Ad type 5 d 1324 or other strains of adenovirus (e.g., Ad2, Ad3, Ad7, etc.) are known to those skilled in the art. Recombinant adenoviruses can be advantageous in certain circumstances in that they are not capable of infecting nondividing cells and can be used to infect a wide variety of cell types, including epithelial cells. Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large relative to other nucleic acid delivery vectors (Haj-Ahmand and Graham (1986) J. Virol. 57:267).

In particular embodiments, the adenovirus genome contains a deletion therein, so that at least one of the adenovirus gene regions does not encode a functional protein. For example, first-generation adenovirus vectors are typically deleted for the E1 genes and packaged using a cell that expresses the E1 proteins (e.g., 293 cells). The E3 region is also frequently deleted as well, as there is no need for complementation of this deletion. In addition, deletions in the E4, E2a, protein IX, and fiber protein regions have been described, e.g., by Armentano et al, (1997) J. Virology 71:2408, Gao et al., (1996) J. Virology 70:8934, Dedieu et al., (1997) J. Virology 71; 4526, Wang et al., (1997) Gene Therapy 4:393, and U.S. Pat. No. 5,882,877 to Gregory et al. (the disclosures of which are incorporated herein in their entirety). Preferably, the deletions are selected to avoid toxicity to the packaging cell. Wang et al., (1997) Gene Therapy 4:393, has described toxicity from constitutive co-expression of the E4 and E1 genes by a packaging cell line. Toxicity may be avoided by regulating expression of the E1 and/or E4 gene products by an inducible, rather than a constitutive, promoter. Combinations of deletions that avoid toxicity or other deleterious effects on the host cell can be routinely selected by those skilled in the art.

As further examples, in particular embodiments, the adenovirus is deleted in the polymerase (pol), preterminal protein (pTP), IVa2 and/or 100K regions (see, e.g., U.S. Pat. No. 6,328,958; PCT publication WO 00/12740; and PCT publication WO 02/098466; Ding et al., (2002) Mol. Ther. 5:436; Hodges et al., J. Virol. 75:5913; Ding et al., (2001) Hum Gene Ther 12:955; the disclosures of which are incorporated herein by reference in their entireties for the teachings of how to make and use deleted adenovirus vectors for nucleic acid delivery). In representative embodiments, the vector is a [E1−, E3−, pol−]Ad, [E1−, E3−, pTP−]Ad, [E1−, E3−, pol1, pTP−]Ad, [E1+, 100K−]Ad or [E1a+, E1b−, 100K]Ad.

The term "deleted" adenovirus as used herein refers to the omission of at least one nucleotide from the indicated region of the adenovirus genome. Deletions can be greater than about 1, 2, 3, 5, 10, 20, 50, 100, 200, or even 500 nucleotides. Deletions in the various regions of the adenovirus genome may be about at least 1%, 5%, 10%, 25%, 50%, 75%, 90%, 95%, 99%, or more of the indicated region. Alternately, the entire region of the adenovirus genome is deleted. Preferably, the deletion will prevent or essentially prevent the expression of a functional protein from that region. For example, it is preferred that the deletion in the 100K region results in the loss of expression of a functional 100K protein from that region. In other words, even if there is transcription across the deleted 100K region and translation of the resulting RNA transcripts, the resulting protein will be essentially non-functional, more preferably, completely non-functional. Alternatively, an insignificant amount of a functional protein is expressed. In general, larger deletions are preferred as these have the additional advantage that they will increase the carrying capacity of the deleted adenovirus for a heterologous nucleotide sequence of interest. The various regions of the adenovirus genome have been mapped and are understood by those skilled in the art (see, e.g., FIELDS et al., VIROLOGY, volume 2, chapters 67 and 68 (3d ed., Lippincott-Raven Publishers)).

Those skilled in the art will appreciate that typically, with the exception of the E3 genes, any deletions will need to be complemented in order to propagate (replicate and package) additional virus, e.g., by transcomplementation with a packaging cell.

In particular embodiments, the present invention excludes "gutted adenovirus" vectors (as that term is understood in the art, see e.g., Lieber, et al., (1996) J. Virol. 70:8944-60) in which essentially all of the adenovirus genomic sequences are deleted. In alternate embodiments, such gutted adenovirus vectors may be an aspect of the invention.

Adeno-associated viruses (AAV) have also been employed as nucleic acid delivery vectors. For a review, see Muzyczka et al. Curr. Topics in Micro. and Immunol. (1992) 158:97-129). AAV are parvoviruses and have small icosahedral virions, 18-26 nanometers in diameter and contain a single stranded DNA molecule 4-5 kilobases in size. The viruses contain either the sense or antisense strand of the DNA molecule and either strand is incorporated into the virion. Two open reading frames encode a series of Rep and Cap polypeptides. Rep polypeptides (Rep50, Rep52, Rep68 and Rep78) are involved in replication, rescue and integration of the AAV genome, although significant activity may be observed in the absence of all four Rep polypeptides. The Cap proteins (VP1, VP2, VP3) form the virion capsid. Flanking the rep and cap open reading frames at the 5' and 3' ends of the genome are 145 basepair inverted terminal repeats (ITRs), the first 125 basepairs of which are capable of forming Y- or T-shaped duplex structures. It has been shown that the ITRs represent the minimal cis sequences required for replication, rescue, packaging and integration of the AAV genome. Typically, in recombinant AAV vectors (rAAV), the entire rep and cap coding regions are excised and replaced with a transgene of interest.

AAV are among the few viruses that may integrate their DNA into non-dividing cells, and exhibit a high frequency of stable integration into human chromosome 19 (see, for example, Flotte et al. (1992) *Am. J. Respir. Cell. Mol. Biol.* 7:349-356; Samulski et al., (1989) *J Virol.* 63:3822-3828; and McLaughlin et al., (1989) *J. Virol,* 62:1963-1973). A variety of nucleic acids have been introduced into different cell types using AAV vectors (see, for example, Hermonat et al., (1984) *Proc. Natl. Acad. Sci. USA* 81:6466-6470; Tratschin et al., (1985) *Mol. Cell. Biol.* 4:2072-2081; Wondisford et al., (1988) *Mol. Endocrinol.* 2:32-39; Tratschin et al., (1984) *J. Virol.* 51:611-619; and Flotte et al., (1993) *J. Biol. Chem.* 268:3781-3790).

A rAAV vector genome will typically comprise the AAV terminal repeat sequences and packaging signal. An "AAV particle" or "rAAV particle" comprises an AAV vector genome or rAAV vector genome, respectively, packaged within an AAV capsid. The rAAV vector itself need not contain AAV genes encoding the capsid and Rep proteins. In particular embodiments of the invention, the rep and/or cap genes are deleted from the AAV genome. In a representative embodiment, the rAAV vector retains only the terminal AAV sequences (ITRs) necessary for integration, excision, replication.

Sources for the AAV capsid genes may include serotypes AAV-1, AAV-2, AAV-3 (including 3a and 3b), AAV-4, AAV-5, AAV-6, AAV-7, AAV-8, as well as bovine AAV and avian AAV, and any other virus classified by the International Committee on Taxonomy of Viruses (ICTV) as an AAV (see, e.g., BERNARD N. FIELDS et al., VIROLOGY, volume 2, chapter 69 (4th ed., Lippincott-Raven Publishers)).

In particular embodiments, the AAV capsid genes are derived from AAV serotypes 1, 2, 5, 6 or 8.

Because of packaging limitations, the total size of the rAAV genome will preferably be less than about 5.2, 5, 4.8, 4.6 or 4.5 kb in size.

Any suitable method known in the art may be used to produce AAV vectors (see, e.g., U.S. Pat. Nos. 5,139,941; 5,858,775; 6,146,874 for illustrative methods). In one particular method, AAV stocks may be produced by co-transfection of a rep/cap vector encoding AAV packaging functions and the template encoding the AAV vDNA into human cells infected with the helper adenovirus (Samulski et al., (1989) *J. Virology* 63:3822).

In other particular embodiments, the adenovirus helper virus is a hybrid helper virus that encodes AAV Rep and/or capsid proteins. Hybrid helper Ad/AAV vectors expressing AAV rep and/or cap genes and methods of producing AAV stocks using these reagents are known in the art (see, e.g., U.S. Pat. Nos. 5,589,377; and 5,871,982, 6,251,677; and 6,387,368). Preferably, the hybrid Ad of the invention expresses the AAV capsid proteins (i.e., VP1, VP2, and VP3). Alternatively, or additionally, the hybrid adenovirus may express one or more of AAV Rep proteins (i.e., Rep40, Rep52, Rep68 and/or Rep78). The AAV sequences may be operatively associated with a tissue-specific or inducible promoter.

The AAV rep and/or cap genes may alternatively be provided by a packaging cell that stably expresses the genes (see, e.g., Gao et al., (1998) *Human Gene Therapy* 9:2353; Inoue et al., (1998) *J. Virol.* 72:7024; U.S. Pat. No. 5,837,484; WO 98/27207; U.S. Pat. No. 5,658,785: WO 96/17947).

In a representative embodiment, the present invention provides a method of producing a rAAV particle comprising an isolated nucleic acid according to the invention, comprising providing to a cell: (a) a nucleic acid encoding a rAAV genome comprising (i) 5' and/or 3' AAV ITR sequences, (ii) an isolated nucleic acid as described above (e.g., a nucleic acid encoding GAA and comprising an abbreviated 3' UTR or a nucleic acid encoding a chimeric lysosomal polypeptide comprising a secretory signal sequence), and (iii) an AAV packaging signal; (b) AAV rep coding sequences sufficient for replication of the recombinant AAV genome; (c) AAV cap coding sequences sufficient to produce a functional AAV capsid; wherein (a) to (c) are provided to the cell under conditions sufficient for replication and packaging of the rAAV genome into the AAV capsid, whereby AAV particles comprising the AAV capsid packaging the rAAV genome are produced in the cell. Typically, the adenovirus or HSV helper functions for AAV replication and packaging are also provided. The method may further include the step of collecting the rAAV particles.

In still further embodiments, the delivery vector is a hybrid Ad-AAV delivery vector, for example, as described in the working Examples and in U.S. Provisional Application 60/376,397 (incorporated by reference herein in its entirety for its teaching of how to make and use hybrid Ad-AAV delivery vectors). Briefly, the hybrid Ad-AAV vector comprises an adenovirus vector genome comprising adenovirus (i) 5' and 3' cis-elements for viral replication and encapsidation and, further, (ii) a recombinant AAV vector genome comprising the AAV 5' and 3' inverted terminal repeats (ITRs), an AAV packaging sequence, and a heterologous sequence(s) flanked by the AAV ITRs, where the recombinant AAV vector genome is flanked by the adenovirus 5' and 3' cis-elements. The adenovirus vector genome may further be deleted, as described above.

Another vector for use in the present invention comprises Herpes Simplex Virus (HSV). Herpes simplex virions have an overall diameter of 150 to 200 nm and a genome consisting of one double-stranded DNA molecule that is 120 to 200 kilobases in length. Glycoprotein D (gD) is a structural component of the HSV envelope that mediates virus entry into host cells. The initial interaction of HSV with cell surface heparin sulfate proteoglycans is mediated by another glycoprotein, glycoprotein C (gC) and/or glycoprotein B (gB). This is followed by interaction with one or more of the viral glycoproteins with cellular receptors. Recently it has been shown that glycoprotein D of HSV binds directly to Herpes virus entry mediator (HVEM) of host cells. HVEM is a member of the tumor necrosis factor receptor superfamily (Whitbeck, J. C. et al., 1997, *J. Virol.;* 71:6083-6093). Finally, gD, gB and the complex of gH and gL act individually or in combination to trigger pH-independent fusion of the viral envelope with the host cell plasma membrane. The virus itself is transmitted by direct contact and replicates in the skin or mucosal membranes before infecting cells of the nervous system for which HSV has particular tropism. It exhibits both a lytic and a latent function. The lytic cycle results in viral replication and cell death. The latent function allows for the virus to be maintained in the host for an extremely long period of time.

HSV can be modified for the delivery of transgenes to cells by producing a vector that exhibits only the latent function for long-term gene maintenance. HSV vectors are useful for nucleic acid delivery because they allow for a large DNA insert of up to or greater than 20 kilobases; they can be produced with extremely high titers; and they have been shown to express transgenes for a long period of time in the central nervous system as long as the lytic cycle does not occur.

In other preferred embodiments of the present invention, the delivery vector of interest is a retrovirus. Retroviruses normally bind to a species specific cell surface receptor, e.g., CD4 (for HIV); CAT (for MLV-E; ecotropic Murine leukemic virus E); RAM1/GLVR2 (for murine leukemic virus-A; MLV-A); GLVR1 (for Gibbon Ape leukemia virus (GALV) and Feline leukemia virus B (FeLV-B)). The development of specialized cell lines (termed "packaging cells") which produce only replication-defective retroviruses has increased the utility of retroviruses for gene therapy, and defective retroviruses are characterized for use in gene transfer for gene therapy purposes (for a review, see Miller, (1990) *Blood* 76:271). A replication-defective retrovirus can be packaged into virions which can be used to infect a target cell through the use of a helper virus by standard techniques.

Yet another suitable vector is a poxvirus vector. These viruses are very complex, containing more than 100 proteins, although the detailed structure of the virus is presently unknown. Extracellular forms of the virus have two membranes while intracellular particles only have an inner membrane. The outer surface of the virus is made up of lipids and proteins that surround the biconcave core. Poxviruses are very complex antigenically, inducing both specific and cross-reacting antibodies after infection. Poxvirus receptors are not presently known, but it is likely that there exists more than one given the ability of poxvirus to infect a wide range of cells. Poxvirus gene expression is well studied due to the interest in using vaccinia virus as a vector for expression of transgenes.

In addition to viral transfer methods, such as those illustrated above, non-viral methods can also be employed. Many non-viral methods of gene transfer rely on normal mechanisms used by mammalian cells for the uptake and intracellular transport of macromolecules. In particular embodiments, non-viral delivery systems rely on endocytic pathways for the uptake of the nucleic acid molecule by the targeted cell. Exemplary nucleic acid delivery systems of this type include liposomal derived systems, poly-lysine conjugates, and artificial viral envelopes.

In particular embodiments, plasmid vectors are used in the practice of the present invention. Naked plasmids can be introduced into muscle cells by injection into the tissue. Expression can extend over many months, although the number of positive cells is typically low (Wolff et al., (1989) *Science* 247:247). Cationic lipids have been demonstrated to aid in introduction of DNA into some cells in culture (Feigner and Ringold, (1989) *Nature* 337:387). Injection of cationic lipid plasmid DNA complexes into the circulation of mice has been shown to result in expression of the DNA in lung (Brigham et al., (1989) *Am. J. Med. Sci.* 298:278). One advantage of plasmid DNA is that it may be introduced into non-replicating cells.

In a representative embodiment, a nucleic acid molecule (e.g., a plasmid) may be entrapped in a lipid particle bearing positive changes on its surface and, optionally, tagged with antibodies against cell surface antigens of the target tissue (Mizuno et al., (1992) *No Shinkei Geka* 20:547; PCT publication WO 91/06309; Japanese patent application 1047381; and European patent publication EP-A-43075).

Liposomes that consist of amphiphilic cationic molecules are useful non-viral vectors for nucleic acid delivery in vitro and in vivo (reviewed in Crystal, *Science* 270: 404-410 (1995); Blaese et al., *Cancer Gene Ther.* 2: 291-297 (1995); Behr et al., *Bioconjugate Chem.* 5: 382-389 (1994); Remy et al., *Bioconjugate Chem.* 5: 647-654 (1994); and Gao et al., *Gene Therapy* 2: 710-722 (1995)). The positively charged liposomes are believed to complex with negatively charged nucleic acids via electrostatic interactions to form lipid:nucleic acid complexes. The lipid:nucleic acid complexes have several advantages as gene transfer vectors. Unlike viral vectors, the lipid:nucleic acid complexes can be used to transfer expression cassettes of essentially unlimited size. Since the complexes lack proteins, they may evoke fewer immunogenic and inflammatory responses. Moreover, they cannot replicate or recombine to form an infectious agent and have low integration frequency. A number of publications have demonstrated that amphiphilic cationic lipids can mediate nucleic acid delivery in vivo and in vitro (Feigner et al., *Proc. Natl. Acad. Sci. USA* 84: 7413-17 (1987); Loeffler et al., *Methods in Enzymology* 217: 599-618 (1993); Feigner et al., *J. Biol. Chem.* 269: 2550-2561 (1994)).

Several groups have reported the use of amphiphilic cationic lipid:nucleic acid complexes for in vivo transfection both in animals and in humans (reviewed in Gao et al., *Gene Therapy* 2: 710-722 (1995); Zhu et al., *Science* 261: 209-211 (1993); and Thierry et al., *Proc. Natl. Acad. Sci. USA* 92: 9742-9746 (1995)). U.S. Pat. No. 6,410,049 describes a method of preparing cationic lipid:nucleic acid complexes that have prolonged shelf life.

IV. Production of Recombinant Lysosomal Polypeptides.

As indicated above, recombinant lysosomal polypeptides such as GAA can be produced in, and optionally purified from, cultured cells or organisms for a variety of purposes. Methods of delivering a recombinant nucleic acid encoding a lysosomal polypeptide for therapeutic methods are described in more detail below. The isolated nucleic acid may be carried by a delivery vector as described in the preceding section.

Those skilled in the art will appreciate that the isolated nucleic acid encoding the lysosomal polypeptide can be operably associated with appropriate expression control sequences, e.g., transcription/translation control signals, which can be included in the isolated nucleic acid or by a vector backbone. For example, specific initiation signals are generally required for efficient translation of inserted protein coding sequences. These exogenous translational control sequences, which may include the ATG initiation codon and adjacent sequences, can be of a variety of origins, both natural and synthetic.

The isolated nucleic acid can further, comprise a polyadenylation signal. (e.g., a signal for polyA polymerase to add the polyA tail to the 3' end of the transcribed mRNA). It is common, however, that the polyadenylation signal is provided by a vector backbone into which the coding sequence is inserted (e.g., a plasmid or a recombinant viral genome) and, therefore, in particular embodiments a polyadenylation signal may not be present in the isolated nucleic acid molecule.

A variety of promoter/enhancer elements may be used depending on the level and tissue-specific expression desired. The promoter can be constitutive or inducible (e.g., the metallothionein promoter or a hormone inducible promoter), depending on the pattern of expression desired. The promoter may be native or foreign and can be a natural or a synthetic sequence. By foreign, it is intended that the transcriptional initiation region is not found in the wild-type host into which the transcriptional initiation region is introduced. The promoter is chosen so that it will function in the target cell(s) of interest. Promoters that function in liver (for example, liver parenchyma, e.g., alpha-1 antitrypsin promoter), skeletal muscle, cardiac muscle, smooth muscle, diaphragm muscle, endothelial cells, intestinal cells, pulmonary cells (e.g., smooth muscle or epithelium), peritoneal epithelial cells and fibroblasts are preferred. The promoter may further be "specific" for these cells and tissues, in that it may only show significant activity in the specific cell or tissue type.

The isolated nucleic acid can be operatively associated with a cytomegalovirus (CMV) major immediate-early promoter, an albumin promoter, an Elongation Factor 1-$\alpha$ (EF1-$\alpha$) promoter, a P$\gamma$K promoter, a MFG promoter, or a Rous sarcoma virus promoter. A hybrid promoter containing the CMV major immediate-early enhancer and chicken beta-actin (CB) promoter is also suitable. It has been speculated that driving heterologous nucleotide transcription with the CMV promoter results in down-regulation of expression in immunocompetent animals (see, e.g., Guo et al., (1996) *Gene Therapy* 3:802). Accordingly, it may be advantageous to operably associate the isolated nucleic acid with a modified CMV promoter that does not result in this down-regulation of transgene expression.

The isolated nucleic acids of the invention can comprise two or more coding sequences. In embodiments wherein there is more than one coding sequence, the coding sequences may be operatively associated with separate promoters or, alternatively, with a single upstream promoter and one or more downstream internal ribosome entry site (IRES) sequences (e.g., the picornavirus EMC IRES sequence).

In particular embodiments of the invention, the total size of the isolated nucleic acid is less than about 5, 4.8, 4.7, 4.6, 4.5, 4.3, 4.2, 4, 3.8, 3.7, 3.6, 3.5, 3.2, 3 or 2.8 kb or less in length. Relatively small expression cassettes can be particularly advantageous for delivery by AAV vectors.

An isolated nucleic acid of the invention can be introduced into a host cell, e.g., a cell of a primary or immortalized cell line. The recombinant cells can be used to produce the encoded polypeptide. Generally, the isolated nucleic acid is incorporated into an expression vector (viral or nonviral as described above).

Expression vectors can be designed for expression of polypeptides in prokaryotic or eukaryotic cells. For example, polypeptides can be expressed in bacterial cells such as *E. coli*, insect cells (e.g., in the baculovirus expression system), yeast cells or mammalian cells. Some suitable host cells are discussed further in Goeddel, Gene Expression Technology: Methods in Enzymology 185, Academic Press, San Diego, Calif. (1990). Examples of vectors for expression in yeast *S. cerevisiae* include pYepSecl (Baldari et al., (1987) *EMBO J.* 6:229-234), pMFa (Kurjan and Herskowitz, (1982) *Cell* 30:933-943), pJRY88 (Schultz et al., (1987) *Gene* 54; 113-123), and pYES2 (Invitrogen Corporation, San Diego, Calif.). Baculovirus vectors available for expression of proteins in cultured insect cells (e.g., Sf 9 cells) include the pAc series (Smith et al., (1983) *Mol. Cell. Biol.* 3:2156-2165) and the pVL series (Lucklow, V. A., and Summers, M.d. (1989) *Virology* 170:31-39).

Examples of mammalian expression vectors include pCDM8 (Seed, (1987) *Nature* 329:840) and pMT2PC (Kaufman et al. (1987), *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40.

In addition to the regulatory control sequences discussed above, the recombinant expression vector can contain additional nucleotide sequences. For example, the recombinant expression vector may encode a selectable marker gene to identify host cells that have incorporated the vector.

Vector DNA can be introduced into prokaryotic or eukaryotic cells via conventional technique including but not limited to calcium phosphate or calcium chloride co-precipitation, DEAE-dextran-mediated transfection, lipofection, electroporation, microinjection and viral-mediated transfection and transduction. Suitable methods for transforming or transfecting host cells can be found in Sambrook et al. (Molecular Cloning: A Laboratory Manual, 2nd Edition, Cold Spring Harbor Laboratory press (1989)), and other laboratory manuals.

Often only a small fraction of cells (in particular, mammalian cells) integrate the foreign DNA into their genome. In order to identify and select these integrants, a nucleic acid sequence that encodes a selectable marker (e.g., resistance to antibiotics) can be introduced into the host cells along with the gene encoding the protein of interest. Preferred selectable markers include those that confer resistance to drugs, such as G418, hygromycin and methotrexate. Nucleic acids encoding a selectable marker can be introduced into a host cell on the same vector as that encoding the protein of interest or can be introduced on a separate vector. Cells stably transfected with the introduced nucleic acid can be identified by drug selection (e.g., cells that have incorporated the selectable marker gene will survive, while the other cells die).

A. Transgenic Animals.

The lysosomal polypeptide may be produced in a non-human transgenic animal (i.e., containing a nucleic acid introduced by human intervention using recombinant nucleic acid techniques). Methods for generating non-human transgenic animals are known in the art. DNA constructs can be introduced into the germ line of an avian or mammal to make a transgenic animal. For example, one or several copies of the construct can be incorporated into the genome of an embryo by standard transgenic techniques.

It is often desirable to express the transgenic polypeptide in the milk of a transgenic mammal. Mammals that produce large volumes of milk and have long lactating periods are preferred. Preferred mammals are ruminants, e.g., cows, sheep, camels or goats (including goats of Swiss origin, such as the Alpine, Saanen and Toggenburg breed goats). Other preferred mammals include oxen, rabbits and pigs.

In an exemplary embodiment, a transgenic non-human animal is produced by introducing a transgene into the germ line of the non-human animal. Transgenes can be introduced into embryonal target cells at various developmental stages. Different methods are used depending on the stage of development of the embryonal target cell. The specific line(s) of any animal used should, if possible, be selected for general good health, good embryo yields, good pronuclear visibility in the embryo, and good reproductive fitness.

Introduction of the transgene into the embryo can be accomplished by any of a variety of means known in the art such as microinjection, electroporation, lipofection or a viral vector. For example, the transgene can be introduced into a mammal by microinjection of the construct into the pronuclei of the fertilized mammalian egg(s) to cause one or more copies of the construct to be retained in the cells of the developing mammal(s). Following introduction of the transgene construct into the fertilized egg, the egg can be incubated in vitro for varying amounts of time or reimplanted into the surrogate host, or both. One common method is to incubate the embryos in vitro for about 1-7 days, depending on the species, and then reimplant them into the surrogate host.

The progeny of the transgenically manipulated embryos can be tested for the presence of the construct, e.g., by Southern blot analysis of a segment of tissue. An embryo having one or more copies of the exogenous cloned construct stably integrated into the genome can be used to establish a permanent transgenic animal line carrying the transgenic construct.

Litters of transgenically altered mammals can be assayed after birth for the incorporation of the construct into the genome of the offspring. This can be done by hybridizing a probe corresponding to the transgenic sequence to chromosomal material from the progeny. Those mammalian progeny found to contain at least one copy of the construct in their genome are grown to maturity. The female species of these progeny will produce the desired polypeptide in or along with their milk. The transgenic mammals can be bred to produce other transgenic progeny useful in producing the desired polypeptides in their milk.

Transgenic females may be tested for polypeptide secretion into milk, using any art-known assay technique, e.g., a Western blot or enzymatic assay.

Useful transcriptional promoters for expressing the polypeptide in the milk of a transgenic animal are those promoters that are preferentially activated in mammary epithelial cells, including promoters that control the genes encoding milk polypeptides such as caseins, beta-lactoglobulin (Clark et al., (1989) *Bio/Technology* 7:487-492), whey acid protein (Gorton et al., (1987) *Bio/Technology* 5: 1183-1187), and lactalbumin (Soulier et al., (1992) *FEBS Lets.* 297:13). The alpha-, beta-, gamma- or kappa-casein gene promoters of any mammalian species can be used to provide mammary expression; a preferred promoter is the goat beta-casein gene promoter (DiTullio, (1992) *Bio/Technology* 10:74-77). Other milk-specific polypeptide promoter or promoters that are specifically activated in mammary tissue can be isolated from cDNA or genomic sequences.

DNA sequence information is available for mammary gland specific genes listed above, in at least one, and often in several organisms. See, e.g., Richards et al., *J Biol. Chem.* 256, 526-532 (1981) (rat alpha-lactalbumin); Campbell et al., *Nucleic Acids Res.* 12, 8685-8697 (1984) (rat WAP); Jones et al., *J. Biol. Chem.* 260: 7042-7050 (1985) (rat beta-casein); Yu-Lee & Rosen, *J. Biol. Chem.* 258, 10794-10804 (1983) (rat gamma-casein); Hall, *Biochem. J.* 242, 735-742 (1987) (human alpha-lactalbumin); Stewart, *Nucleic Acids Res.* 12, 389 (1984) (bovine alpha S1 and kappa casein cDNAs); Gorodetsky et al., *Gene* 66, 87-96 (1988) (bovine beta-casein); Alexander et al., *Eur. J. Biochem.* 178, 395-401 (1988) (bovine kappa-casein); Brignon et al., *FEBS Lett.* 188, 48-55 (1977) (bovine alpha S2 casein); Jamieson et al., *Gene* 61, 85-90 (1987), Ivanov et al., *Biol. Chem.* Hoppe-Seyler 369, 425-429 (1988), Alexander et al., *Nucleic Acids Res.* 17, 6739 (1989) (bovine beta lactoglobulin); Vilotte et al., *Biochimie* 69, 609-620 (1987) (bovine alpha-lactalbumin). The structure and function of the various milk protein genes are reviewed by Mercier & Vilotte, *J. Dairy Sci.* 76, 3079-3098 (1993). If additional flanking sequence is useful in optimizing expression, such sequences can be cloned using the existing sequences, as probes. Mammary-gland specific regulatory sequences from different organisms can be obtained by screening libraries from such organisms using known cognate nucleotide sequences, or antibodies to cognate polypeptides, as probes.

According to this embodiment, the isolated nucleic acid may be operatively associated with a milk-specific signal sequence, e.g., from a gene which encodes a product secreted into milk. For example, signal sequences from genes coding for caseins (e.g., alpha-, beta-, gamma- or kappa-caseins). beta-lactoglobulin, whey acid protein, and lactalbumin are useful in the present invention.

The polypeptide can be expressed from an illustrative expression construct that includes a promoter specific for mammary epithelial cells, e.g., a casein promoter (for example, a goat beta-casein promoter), a milk-specific signal sequence, e.g., a casein signal sequence (for example, beta-casein signal sequence), and a sequence encoding the polypeptide.

The transgenic polypeptide can be produced in milk at relatively high concentrations and in large volumes, providing continuous high level output of normally processed polypeptide that is easily harvested from a renewable resource. There are several different methods known in the art for isolation of polypeptides from milk.

Milk polypeptides usually are isolated by a combination of processes. Raw milk first is fractionated to remove fats, for example, by skimming, centrifugation, sedimentation (H. E. Swaisgood, Developments in Dairy Chemistry, I: Chemistry of Milk Protein, Applied Science Publishers, NY, 1982), acid precipitation (U.S. Pat. No. 4,644,056) or enzymatic coagulation with rennin or chymotrypsin (Swaisgood, ibid.). Next, the major milk proteins may be fractionated into either a clear solution or a bulk precipitate from which the specific protein of interest may be readily purified.

U.S. Ser. No. 08/648,235 discloses a method for isolating a soluble milk component, such as a protein, in its biologically active form from whole milk or a milk fraction by tangential flow filtration. Unlike previous isolation methods, this eliminates the need for a first fractionation of whole milk to remove fat and casein micelles, thereby simplifying the process and avoiding losses of recovery and bioactivity. This method may be used in combination with additional purification steps to further remove contaminants and purify the component of interest.

B. Production of Transgenic Polypeptides in the Eggs of a Transgenic Avian.

Recombinant polypeptide can also be produced in the eggs of a transgenic avian, e.g., a transgenic chicken, turkey, duck, goose, ostrich, guinea fowl, peacock, partridge, pheasant, pigeon, quail using methods known in the art (Sang et al., *Trends Biotechnology,* 12:415-20, 1994). Genes encoding polypeptides specifically expressed in the egg, such as yolk-protein genes and albumin-protein genes, can be modified to direct expression of the lysosomal polypeptides of the invention.

Useful promoters for producing polypeptides in avian eggs are those promoters that are preferentially activated in the egg, including promoters that control the genes encoding egg polypeptides, e.g., ovalbumin, lysozyme and avidin. Promoters from the chicken ovalbumin, lysozyme or avidin genes are preferred. Egg-specific promoters or the promoters that are specifically activated in egg tissue can be from cDNA or genomic sequences.

DNA sequences of egg specific genes are known in the art (see, e.g., Burley et al., "The Avian Egg", John Wiley and Sons, p. 472, 1989, the contents of which are incorporated herein by reference). Egg specific regulatory sequences from different organisms can be obtained by screening libraries from such organisms using known cognate nucleotide sequences, or antibodies to cognate polypeptides, as probes.

C. Transgenic Plants.

Recombinant polypeptides can be expressed in a transgenic plant in which the transgene is inserted into the nuclear or plastidic genome. Plant transformation is known as the art. See, in general, Methods in Enzymology Vol. 153 ("Recombinant DNA Part D") 1987, Wu and Grossman Eds., Academic Press and European Patent Application EP 693 554.

Foreign nucleic acids can be introduced into plant cells or protoplasts by several methods. For example, nucleic acid can be mechanically transferred by microinjection directly into plant cells by use of micropipettes. Foreign nucleic acid can also be transferred into a plant cell by using polyethylene glycol which forms a precipitation complex with the genetic material that is taken up by the cell (Paszkowski et al. (1954) *EMBO J.* 3:2712-22). Foreign nucleic acid can also be introduced into a plant cell by electroporation (Fromm et al. (1985) *Proc. Natl. Acad. Sci. USA* 62:5824). In this technique, plant protoplasts are electroporated in the presence of plasmids or nucleic acids containing the relevant genetic construct. Electrical impulses of high field strength reversibly permeabilize biomembranes allowing the introduction of the plasmids. Electroporated plant protoplasts reform the cell wall, divide, and form a plant callus. Selection of the transformed plant cells with the transformed gene can be accomplished using phenotypic markers.

Cauliflower mosaic virus (CaMV) can be used as a vector for introducing foreign nucleic acids into plant cells (Hohn et al. (1982) "Molecular Biology of Plant Tumors," Academic Press, New York, pp. 549-560; Howell, U.S. Pat. No. 4,407,956). CaMV viral DNA genome is inserted into a parent bacterial plasmid creating a recombinant DNA molecule which can be propagated in bacteria. The recombinant plasmid can be further modified by introduction of the desired DNA sequence. The modified viral portion of the recombinant plasmid is then excised from the parent bacterial plasmid, and used to inoculate the plant cells or plants.

High velocity ballistic penetration by small particles can be used to introduce foreign nucleic acid into plant cells. Nucleic acid is disposed within the matrix of small beads or particles, or on the surface (Klein et al. (1987) *Nature* 327:70-73). Although typically only a single introduction of a new nucleic acid segment is required, this method also provides for multiple introductions.

A nucleic acid can be introduced into a plant cell by infection of a plant cell, an explant, a meristem or a seed with *Agrobacterium tumefaciens* or *Agrobacterium rhizogenes* transformed with the nucleic acid. Under appropriate conditions, the transformed plant cells are grown to form shoots, roots, and develop further into plants. The nucleic acids can be introduced into plant cells, for example, by means of the Ti plasmid of Agrobacteria. The Ti plasmid is transmitted to plant cells upon infection by Agrobacteria, and is stably integrated into the plant genome (Horsch et al. (1984) "Inheritance of Functional Foreign Genes in Plants," *Science* 233:496498; Fraley et al. (1983) *Proc. Natl. Aced. Sci. USA* 80:4803).

Plants from which protoplasts can be isolated and cultured to give whole regenerated plants can be transformed so that whole plants are recovered which contain the transferred foreign gene. Some suitable plants include, for example, species from the genera *Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Hyoscyamus, Lycopersicon, Nicotiana, Solanum, Petunia, Digitalis, Majorana, Ciohorium, Helianthus, Lactuca, Bromus, Asparagus, Antirrhinum, Hererocallis, Nemesia, Pelargonium, Panicum, Pennisetum, Ranunculus, Senecio, Salpiglossis, Cucumis, Browaalia, Glycine, Lolium, Zea, Triticum, Sorghum*, and *Datura*.

Plant regeneration from cultured protoplasts is described in Evans et al. "Protoplasts Isolation and Culture," Handbook of Plant Cell Cultures 1:124-176 (MacMillan Publishing Co. New York 1983); M. R. Davey, "Recent Developments in the Culture and Regeneration of Plant Protoplasts," Protoplasts (1983)—Lecture Proceedings, pp. 12-29, (Birkhauser, Basal 1983); P. J. Dale, "Protoplast Culture and Plant Regeneration of Cereals and Other Recalcitrant Crops." Protoplasts (1983)—Lecture Proceedings, pp. 31-41, (Birkhauser, Basel 1983); and H. Binding, "Regeneration of Plants," Plant Protoplasts, pp. 21-73, (CRC Press, Boca Raton 1985).

Regeneration from protoplasts varies from species to species of plants, but generally a suspension of transformed protoplasts containing copies of the exogenous sequence is first generated. In certain species, embryo formation can then be induced from the protoplast suspension, to the stage of ripening and germination as natural embryos. The culture media can contain various amino acids and hormones, such as auxin and cytokinins. It can also be advantageous to add glutamic acid and praline to the medium especially for such species as corn and alfalfa. Shoots and roots normally develop simultaneously. Efficient regeneration will depend on the medium, on the genotype, and on the history of the culture. If these three variables are controlled, then regeneration is fully reproducible and repeatable.

In vegetatively propagated crops, the mature transgenic plants can be propagated by the taking of cuttings or by tissue culture techniques to produce multiple identical plants for trailing, such as testing for production characteristics. Selection of a desirable transgenic plant is made and new varieties are obtained thereby, and propagated vegetatively for commercial sale. In seed propagated crops, the mature transgenic plants can be self crossed to produce a homozygous inbred plant. The inbred plant produces seed containing the transgene. These seed can be grown to produce plants that have the selected phenotype. The inbreds according to this invention can be used to develop new hybrids. In this method a selected inbred line is crossed with another inbred line to produce the hybrid.

Parts obtained from a transgenic plant, such as flowers, seeds, leaves, branches, fruit, and the like are covered by the invention, provided that these pats include cells which have been so transformed. Progeny and variants, and mutants of the regenerated plants are also included within the scope of this invention, provided that these parts comprise the introduced nucleic acid sequences. Progeny and variants, and mutants of the regenerated plants are also included within the scope of this invention.

Selection of transgenic plants or plant cells can be based upon a visual assay, such as observing color changes (e.g., a white flower, variable pigment production, and uniform color pattern on flowers or irregular patterns), but can also involve biochemical assays of either enzyme activity or product quantitation. Transgenic plants or plant cells are grown into plants bearing the plant part of interest and the gene activities are monitored, such as by biochemical assays (Northern blots); Western blots, and enzyme assays. Appropriate plants are selected and further evaluated. Methods for generation of genetically engineered plants are further described in U.S. Pat. Nos. 5,283,184, 5,482,852, and European Patent Application EP 693 554, all of which are incorporated herein by reference.

V. Subjects, Pharmaceutical Formulations, Vaccine and Modes of Administration.

The present invention finds use in veterinary and medical applications. Suitable subjects include both avians and mammals, with mammals being preferred. The term "avian" as used herein includes, but is not limited to, chickens, ducks, geese, quail, turkeys and pheasants. The term "mammal" as used herein includes, but is not limited to, non-human primates, bovines, ovines, caprines, equines, felines, canines, lagomorphs, rats, mice etc. Human subjects are preferred. Human subjects include neonates, infants, juveniles, and adults. In representative embodiments, the subject is a human subject that has or is believed to have a lysosomal polypeptide (e.g., GAA) deficiency.

In particular embodiments, the present invention provides a pharmaceutical composition comprising an isolated nucleic acid or vector of the invention in a pharmaceutically-acceptable carrier and, optionally, other medicinal agents, pharmaceutical agents, carriers, adjuvants, dispersing agents, diluents, and the like. For injection, the carrier will typically be a liquid, such as sterile pyrogen-free water, pyrogen-free phosphate-buffered saline solution, bacteriostatic water, or Cremophor EL[R] (BASF, Parsippany, N.J.). For other methods of administration, the carrier may be either solid or liquid.

By "pharmaceutically acceptable" it is meant a material that is not biologically or otherwise undesirable, i.e., the material may be administered to a subject along with the isolated nucleic acid or vector without causing any undesirable biological effects such as toxicity. Thus, such a pharmaceutical composition can be used, for example, in transfection of a cell ex vivo or in administering an isolated nucleic acid or vector directly to a subject.

In the case of a viral vector, virus particles may be contacted with the cells at the appropriate multiplicity of infection according to standard transduction methods appropriate for the particular target cells. Titers of virus to administer can vary, depending upon the target cell type and the particular virus vector, and can be determined by those of skill in the an without undue experimentation. Typically, at least about $10^3$ virus particles, at least about $10^5$ particles, at least about $10^7$ particles, at least about $10^9$ particles, at least about $10^{11}$ particles, or at least about $10^{12}$ particles are administered to the cell. In exemplary embodiments, about $10^7$ to about $10^{15}$ particles, about $10^7$ to about $10^{13}$ particles, about $10^8$ to about $10^{12}$ particles, about $10^{10}$ to about $10^{15}$ particles, about $10^{11}$ to about $10^{15}$ particles, about $10^{12}$ to about $10^{14}$ particles, or about $10^{12}$ to about $10^{13}$ particles are administered.

The cell to be administered the vectors of the invention can be of any type, including but not limited to neuronal cells (including cells of the peripheral and central nervous systems), retinal cells, epithelial cells (including dermal, gut, respiratory, bladder, pulmonary, peritoneal and breast tissue epithelium), muscle (including cardiac, smooth muscle, including pulmonary smooth muscle cells, skeletal muscle, and diaphragm muscle), pancreatic cells (including islet cells), hepatic cells (including parenchyma), cells of the intestine, fibroblasts (e.g., skin fibroblasts such as human skin fibroblasts), fibroblast-derived cells, endothelial cells, intestinal cells, germ cells, lung cells (including bronchial cells and alveolar cells), prostate cells, stem cells, progenitor cells, dendritic cells, and the like. Alternatively, the cell is a cancer cell (including tumor cells). Moreover, the cells can be from any species of origin, as indicated above.

Mammalian cells include but are not limited to CHO cells, 293 cells, HT1080 cells, HeLa cells or C10 cells.

In particular embodiments of the invention, the cell has been removed from a subject, the vector is introduced therein, and the cell is then replaced back into the subject. Methods of removing cells from subjects for treatment ex vivo, followed by introduction back into the subject are known in the art (see, e.g., U.S. Pat. No. 5,399,346 for the teaching of ex vivo virus vector administration). As a further alternative, the cells that are manipulated and then introduced into the subject are provided from another subject or cell line as a cell-based form of therapy.

A further aspect of the invention is a method of treating subjects in vivo with the inventive nucleic acids or delivery vectors. Administration of the nucleic acid or delivery vectors of the present invention to a human subject or an animal can be by any means known in the art. The subject can be a mammalian subject, more particularly a human subject. In other embodiments, the subject is in need of treatment, for example, has been diagnosed with or is suspected of having a lysosomal polypeptide (e.g., GAA) deficiency.

Dosages will depend upon the mode of administration, the severity of the disease or condition to be treated, the individual subject's condition, the particular vector, and the gene to be delivered, and can be determined in a routine manner (see, e.g., Remington, *The Science And Practice of Pharmacy* ($9^{th}$ Ed. 1995)). In particular embodiments, the isolated nucleic acid or vector is administered to the subject in a therapeutically effective amount, as that term is defined above.

Typically, with respect to viral vectors, at least about $10^3$, at least about $10^5$, at least about $10^7$, at least about $10^9$, at least about $10^{11}$ virus particles, or at least about $10^{12}$ virus particles are administered to the subject per treatment. Exemplary doses are virus titers of about $10^7$ to about $10^{15}$ particles, about $10^7$ to about $10^{14}$ particles, about $10^8$ to about $10^{13}$ particles, about $10^{10}$ to about $10^{15}$ particles, about $10^{11}$ to about $10^{15}$ particles, about $10^{12}$ to about $10^{14}$ particles, or about $10^{12}$ to about $10^{13}$ particles.

In particular embodiments of the invention, more than one administration (e.g., two, three, four, or more administrations) may be employed to achieve therapeutic levels of nucleic acid expression.

Exemplary modes of administration include oral, rectal, transmucosal, topical, transdermal, inhalation, parenteral, e.g., intravenous, subcutaneous, intradermal, intramuscular (i.e., administration to cardiac, skeletal, diaphragm and/or smooth muscle), and intraarticular administration, and the like, as well as direct tissue (e.g., muscle) or organ injection (e.g., into the liver, into the brain for delivery to the central nervous system), alternatively, intrathecal, direct intramuscular (e.g., into cardiac, skeletal, or diaphragm muscle), intraventricular, intravenous, intraperitoneal, intranasal, or intraocular injections. Administration to the liver (discussed below) is another representative mode of administration.

Injectables can be prepared in conventional forms, either as liquid solutions or suspensions, solid forms suitable for solution or suspension in liquid prior to injection, or as emulsions. An injection medium will typically be an aqueous liquid that contains the additives usual for injection solutions, such as stabilizing agents, salts or saline, and/or buffers.

For oral administration, the isolated nucleic acid or vector can be administered in solid dosage forms, such as capsules, tablets, and powders, or in liquid dosage forms, such as elixirs, syrups, and suspensions. Active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that may be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Oral administration of AAV vectors has been described by U.S. Pat. No. 6,110,456 (incorporated by reference herein in its entirety).

The isolated nucleic acid or vector may alternatively be formulated for nasal administration or otherwise administered to the lungs of a subject by any suitable means, but is preferably administered by an aerosol suspension of respirable particles comprising the vector, which the subject inhales. The respirable particles may be liquid or solid. The term "aerosol" includes any gas-borne suspended phase, which is capable of being inhaled into the bronchioles or nasal passages. Specifically, aerosol includes a gas-borne suspension of droplets, as may be produced in a metered dose inhaler or nebulizer, or in a mist sprayer. Aerosol also includes a dry powder composition suspended in air or other carrier gas, which may be delivered by insufflation from an inhaler device, for example. See Ganderton & Jones, *Drug Delivery to the Respiratory Tract*, Ellis Horwood (1987); Gonda (1990) *Critical Reviews in Therapeutic Drug Carrier Systems* 6:273-313; and Raeburn et al. (1992) *J. Pharmacol. Toxicol. Methods* 27:143-159. Aerosols of liquid particles comprising the isolated nucleic acid or vector may be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the isolated nucleic acid or vector may likewise be produced with any solid particulate medicament aerosol generator, by techniques known in the pharmaceutical art.

Alternatively, one may administer the isolated nucleic acid or vector in a local rather than systemic manner, for example, in a depot or sustained-release formulation.

In particular embodiments of the invention, the isolated nucleic acid or vector is delivered to the liver of the subject. Administration to the liver can be achieved by any method known in the art, including, but not limited to intravenous administration, intraportal administration, intrabiliary administration, intra-arterial administration, injection into the liver parenchyma, and intrasplenic injection.

Intramuscular delivery and intracardiac delivery to skeletal muscle or cardiac muscle, respectively, or direct injection into diaphragm muscle is also preferred. In other particular embodiments, intraperitoneal administration is used to deliver the isolated nucleic acid or vector to diaphragm muscle.

In particular embodiments, the isolated nucleic acid (e.g., carried by an Ad, AAV or hybrid Ad/AAV vector) encoding a lysosomal polypeptide is introduced into a depot organ or tissue (e.g., liver, skeletal muscle, lung) and the polypeptide is expressed therein and secreted into the circulatory system, where it is optionally delivered to target tissues, preferably, in a therapeutically effective amount. Intramuscular delivery to skeletal muscle or delivery to the liver are illustrative for the practice of this embodiment of the invention. Alternatively, the isolated nucleic acid or vector can be administered to the brain (e.g., to treat MPS disorders such as Sly disease), where the polypeptide can be expressed and secreted by transformed or transduced cells (e.g., neurons, glial cells) and taken up by other brain cells.

Having now described the invention, the same will be illustrated with reference to certain examples, which are included herein for illustration purposes only, and which are not intended to be limiting of the invention.

EXAMPLE 1

Materials and Methods

Cell Culture. 293 cells and C-7 cells (Amalfitano and Chamberlain. (1997) *Gene Ther.* 4:258-263) were maintained in Dulbecco's modified Eagle medium supplemented with 10% fetal bovine serum, 100 U penicillin per milliliter, and 100 µg streptomycin per milliliter at 37° C. in a 5% $CO_2$-air atmosphere. C-7 cells were grown in the presence of hygromycin, 50 µg/ml. HeLa cells were maintained in minimum essential medium Eagle supplemented with 10% fetal bovine serum, 1 mM minimum essential medium sodium pyruvate, 0.1 mM minimum essential medium non-essential amino acids, 100 U penicillin per milliliter, and 100 µg streptomycin per milliliter at 37° C. in a 5% $CO_2$-air atmosphere.

Construction of an AAV Vector Plasmid Encoding hGAA. The hGAA cDNA was subcloned with the CMV promoter from pcDNA3-hGAA (Van Hove et al., (1996), *Proc. Natl. Acad. Sci. USA* 93:65-70) into an AAV vector plasmid, as an NruI-EcoRV fragment, upstream of the human growth hormone intron 4 and polyadenylation sequence (Brinster et al. (1988), *Proc. Natl. Acad. Sci. USA* 85: 836-840). The resulting transcriptional unit was flanked by the AAV2 terminal repeat (TR) sequences in pAAV-ChGAAGH. A 530 bp deletion spanning the human growth hormone intron 4 was generated by EcoRV and partial PvuII digestion followed by blunting of ends with T4 DNA polymerase and ligation with T4 DNA ligase to generate pAAV-ChGAAG (–). The hybrid CMV enhancer/chicken β-actin (CB) promoter was amplified by polymerase chain reaction from pTriEx1 (Novagen, Madison, Wis.) with primers that introduced unique upstream XbaI and downstream KpnI restriction sites, and the CB promoter was subcloned as a KpnI-XbaI fragment to replace the CMV promoter in pAAV-ChGAAG(–), to generate pAAV-CBhGAAG(–). Next, in order to reduce the packaging size further, the plasmid pAAV-CBhGAAG(–) was linearized at a unique AflII site in the 3' untranslated sequence of the hGAA cDNA and partially digested with NspI to introduce a 411 bp deletion in the 3' untranslated sequence of the hGAA cDNA, followed by blunting of ends with T4 DNA polymerase and ligation with T4 DNA ligase to generate pAAV-CBGAApA. Finally, the vector sequences from pAAV-CBGAApA were isolated as a 4.4 kbp fragment from a partial BglII digest, and ligated with the calf intestinal alkaline phosphatase-dephosphorylated BglII site of pShuttle (He et al. (1998). *Proc. Natl. Acad. Sci. USA* 95:2509-2514).

Construction of a hybrid [E1-, polymerase-, preterminal protein-] Ad-AAV vector encoding hGAA. Kanamycin-resistant shuttle plasmids were constructed to contain within the Ad E1 region the CB promoter+hGAA cDNA+polyA transgene cassette flanked by the AAV2 TR sequences. The shuttle plasmid was digested with PmeI, and electroporated into the BJ5183 recombinogenic strain of *E. Coli* with the pAd[E1-, polymerase-, preterminal protein-] plasmid (Hodges et al. (2000), *J. Gene Med.* 2:250-259). Recombinant kanamycin-resistant clones were screened by restriction enzyme digestion (BstXI) to confirm successful generation of the full-length recombinant Ad vector genomes. These clones were digested with PacI and transfected as previously described into the E1, and E2b expressing cell line, C-7 (Hodges et al., (2000), *J. Gene Med.* 2:250-259). The vectors were amplified and confirmed to have the correct construction by restriction enzyme mapping of vector genomes, and subsequent functional assays in vitro and in vivo. Once isolated, the respective Ad vectors are serially propagated in increasing numbers of C-7 cells (Amalfitano et al. (1998) *J. Virol.* 72:926-933). Forty-eight hours after infection, infected cell pellets were harvested by low speed centrifugation, resuspended in 10 mM Tris-HCl pH 8.0, vector released from the cells by repeated freeze-thawing (×3) of the lysate, released by ultrasonification, and the vector containing supernatant subjected to two rounds of equilibrium density CsCl centrifugation (Amalfitano et al., (1998) *J. Virol.* 72:926-933). Two virus bands were visible. The virus bands were then removed, dialyzed extensively against 10 mM Tris-HCl pH 8.0 (or PBS), sucrose added to 1%, and aliquots stored at −80° C. The number of vector particles was quantified based on the $OD_{250}$ of vector contained in dialysis buffer with sodium dodecyl sulfate (SDS) disruption, and by DNase I digestion, DNA extraction, and Southern blot analysis.

Hybrid Ad-AAV vector DNA analysis consisted of vector DNA isolation and restriction enzyme digestion followed by Southern blotting to verify the presence of intact AAV vector sequences within the lower band in the cesium chloride gradient, including restriction enzymes that demonstrated the presence of AAV terminal repeat sequences flanking the transgene (AhdI and BssHII).

All viral vector stocks were handled according to Biohazard Safety Level 2 guidelines published by the NIH.

In vivo administration of hybrid Ad-AAV or AAV vector stocks. The vector was administered intramuscularly into both gastrocnemius muscles of 3-day-old GAA-KO mice (Raben et al. (1998) *J. Biol. Chem.*, 273:19086-19092). A total of $4 \times 10^{10}$ DNase I-resistant Ad-AAV vector particles were administered, divided between 2 equal injections per animal. Alternatively, a total of $10^{11}$ DNase I-resistant AAV vector particles was administered intramuscularly in the right gastrocnemius muscle of 6 week-old GAA-KO/SCID mice. For liver-targeted administration, a total of $10^{11}$ DNase I-resistant AAV vector particles was administered intravenously via the retroorbital sinus or via the portal vein to 3 month-old GAA-KO/SCID or GAA-KO mice as indicated. At the respective time points post-injection, plasma or tissue samples were obtained and processed as described below. All animal procedures were done in accordance with Duke University Institutional Animal Care and Use Committee-approved guidelines.

Determination of hGAA activity and glycogen content. Tissue hGAA activity was measured following removal of the tissue from control or treated mice, flash-freezing on dry ice, homogenization and sonication in distilled water, and pelleting of insoluble membranes/proteins by centrifugation. The protein concentrations of the clarified suspensions were quantified via the Bradford assay. hGAA activity in the muscle was determined as described (Amalfitano et al. (1999) *Proc. Natl. Acad. Sci. USA* 96:8861-8866). Glycogen content of tissues was measured using the *Aspergillus niger* assay system, as described (Kikuchi et al. (1998) *J. Clin. Invest.* 101:827-833). A two-tailed homscedastic Student's t-test was used to determine significant differences in hGAA levels and glycogen content between GAA-KO mice with or without administration of the vector encoding hGAA.

Western blotting analysis of hGAA. For direct detection of hGAA in tissues, samples (100 μg of protein) were electrophoresed overnight in a 6% polyacrylamide gel to separate proteins, and transferred to a nylon membrane. The blots were blocked with 5% nonfat milk solution, incubated with primary and secondary antibodies and visualized via the enhanced chemiluminescence (ECL) detection system (Amersham Pharmacia, Piscataway, N.J.).

ELISA detection of plasma anti-hGAA and anti-Ad antibodies. Recombinant hGAA (5 μg) in carbonate buffer was coated onto each well of a 96-well plate at 4° C. overnight. Alternatively, the wells were coated with $5 \times 10^8$ Ad vector particles per well at 4° C. overnight for detection of anti-Ad antibody. After washing with phosphate buffered saline (PBS) containing 0.05% Tween 20, serial dilutions of the plasma were added to the wells, and incubated for 1 hour at room temperature. The wells were washed with 0.05% Tween 20+PBS, incubated with a 1:2,500 dilution of alkaline phosphatase-conjugated sheep anti-mouse IgG (H+L) at room temperature for 1 hour, washed, and alkaline phosphatase substrate (p-nitrophenyl phosphate) added. The absorbance values of the plates were read at 405 nm with a Bio-Rad microplate reader ELISA (all samples yielded absorbance values that were within the linear range of the assay at this dilution) (Ding et al. (2002) *Mol. Ther.* 5:436-446). The titer of antibody was determined as the highest dilution where the value for absorbance exceeded 0.1.

EXAMPLE 2

Neonatal Muscle-Targeted Ad-AAV Administration and hGAA Production in GAA-KO Mice Muscle-targeted expression of hGAA with an Ad-AAV hybrid vector was evaluated in neonatal GAA-KO mice. While the Ad-AAV vector delivered muscle-targeted hGAA in these experiments, the hybrid Ad-AAV vector in question was developed to provide improved AAV vector packaging efficiency. Administration of the Ad-AAV vector in 3 day-aid mice reversed the effects of GSD II within the injected gastrocnemius muscle, and sustained hGAA expression provided long-term therapeutic results evidenced by generally reduced glycogen storage in the muscles of the hind limb.

The Ad-AAV vector encoding hGAA was targeted to both gastrocnemius muscles by intramuscular injection on day of life 3 in GAA-KO mice, and hGAA levels were analyzed at 6, 12, and 24 weeks of age. Western blot analysis of hGAA in the gastrocnemius, hamstrings and quadriceps muscle groups at 24 weeks of age showed hGAA of the ~110 kD, 76 kD and 67 kD isoforms following Ad-AAV vector administration, and hGAA was absent for the skeletal muscle of untreated GAA-KO mice (FIG. 1 Panel A). Apparently due to transduction of muscle adjacent to the gastrocnemius, the highest amount of hGAA was seen in the hamstrings, with slightly lower hGAA in the gastrocnemius and the lowest hGAA in the quadriceps. A similar pattern of introduced hGAA, was detected by Western Blot analysis of gastrocnemius and quadriceps muscle groups following Ad-AAV vector administration at 6 and 12 weeks of ace (not shown).

Western blot analysis of hGAA in heart, diaphragm, and liver at 6, 12, and 24 weeks of age following neonatal Ad-AAV vector administration demonstrated low, detectable levels of hGAA for the ~76 kD isoform of hGAA in 2 of 4 GAA-KO mice at 6 weeks (FIG. 1 Panel B; m1 and m4). Lower hGAA was present in the heart for 1 of 4 GAA-KO mice at 24 weeks (FIG. 1 Panel B) m12), and was not detected in the heart for 5 GAA-KO mice at 12 weeks of age (FIG. 1 Panel B) Finally, hGAA was not detected in plasma by Western blot at 3 weeks following vector administration (not shown).

Figure 2:
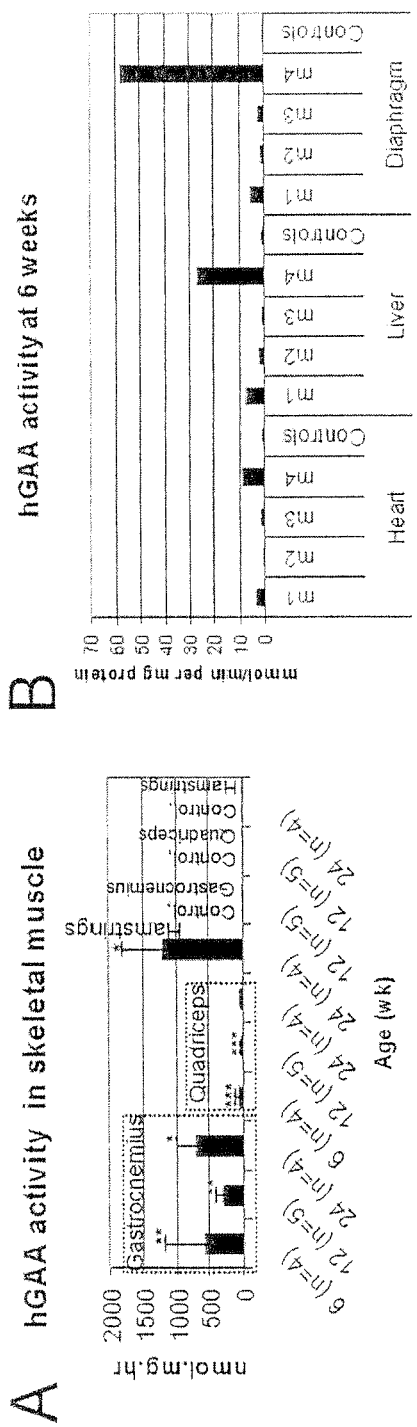
FIG. 2. GAA activity and glycogen content for skeletal muscle and other tissues in GAA-KO mice following neonatal Ad-AAV vector administration. (Panel A) The hGAA activity for gastrocnemius and quadriceps at 6, 12, and 24 weeks following vector administration, and for hamstrings at 24 weeks, compared to the hGAA activity in gastrocnemius, quadriceps, and hamstrings for untreated, GAA-KO mice. The average and standard deviation are shown. The p value is indicated as follows: *<0.05, <0.01, and *<0.001. The number of mice (n) is shown for each time point. (Panel B) The hGAA activity for heart, liver, and diaphragm in mice following Ad-AAV vector administration, and for controls. Controls were untreated, GAA-KO mice: n=4 for heart and liver, n=5 for diaphragm. The average and standard deviation are shown for controls.

The function of hGAA introduced by the Ad-AAV vector was analyzed by GAA enzyme assay, and GAA activity correlated with the relative amounts of hGAA protein detected by Western blot analysis (FIG. 2 Panel A). At 24 weeks, the highest GAA activity was present in hamstrings (1180+/−620 nmol/mg/hr), followed by gastrocnemius (717+/−275 nmol/mg/hr), and lowest in quadriceps (44+/−28 nmol/mg/hr). GAA activity was elevated in all muscle groups at 6, 12, and 24 weeks, compared to the same muscle groups in untreated, GAA-KO mice (FIG. 2 Panel B). The hGAA activity for hamstrings was approximately 50-fold elevated compared to the GAA activity in wild-type mouse skeletal muscle (Ding, E., et al. (2002) *Mol. Ther.* 5:436-446).

GAA activity was elevated in heart, diaphragm and liver at 6 weeks of age following Ad-AAV vector administration in 2 of 4 GAA-KO mice (FIG. 2 Panel B; m1 and m4). However, GAA activity in these tissues was much lower than for skeletal muscles in the hindleg closer to the site of Ad-AAV vector injection (FIG. 2 Panel B).

EXAMPLE 3

Anti-hGAA Antibodies Following Neonatal Ad-AAV Administration

Ant-hGAA antibody formation occurred during hGAA enzyme replacement in GSD II during a clinical trial (Amalfitano et al. (2001) *Genet. In Med.* 3:132-138) and in preclinical use of adenoviral vectors in GAA-KO mice (Ding et al. (2002) *Mol. Ther.* 5:436-446). Anti-hGAA antibodies were detected in GAA-KO mice at 6, 12, and 24 weeks after neonatal Ad-AAV vector administration (FIG. 3 Panel A, Neonatal intramuscular Ad-AAV), with 3 exceptions, while anti-hGAA antibodies were absent in untreated GAA-KO mice (FIG. 3 Panel A, Control). Adult GAA-KO mice that received the Ad-AAV vector intravenously were used as positive controls (FIG. 3 Panel A, Ad-AAV). These mice developed high-titer antihGAA antibodies as reported previously (Ding, E., et al. (2002) *Mol. Ther.* 5:436-446). The presence of hGAA antibodies at a titer of >1:4,000 was demonstrated for 10 of 13 mice following neonatal Ad-AAV vector administration (FIG. 3 Panel B, Neonatal intramuscular Ad-AAV), and for 3 of 3 adult GAA-KO mice following intravenous Ad-AAV vector administration (FIG. 3 Panel B, Ad-AAV). Only the 3 GAA-KO mice that failed to generate anti-hGAA antibodies following neonatal vector administration (m1, m4, and m12 in FIG. 3 Panel B) also featured significant hGAA by Western blot analysis in heart at 6 and 24 weeks of age (FIG. 1 Panel B). The formation of anti-hGAA antibodies appeared to be related to the persistent expression of the foreign transgene (hGAA), because GAA-KO mice failed to generate anti-Ad antibodies following neonatal, one-time exposure to the Ad-AAV vector (FIG. 3 Panel C).

EXAMPLE 4

Figure 4:
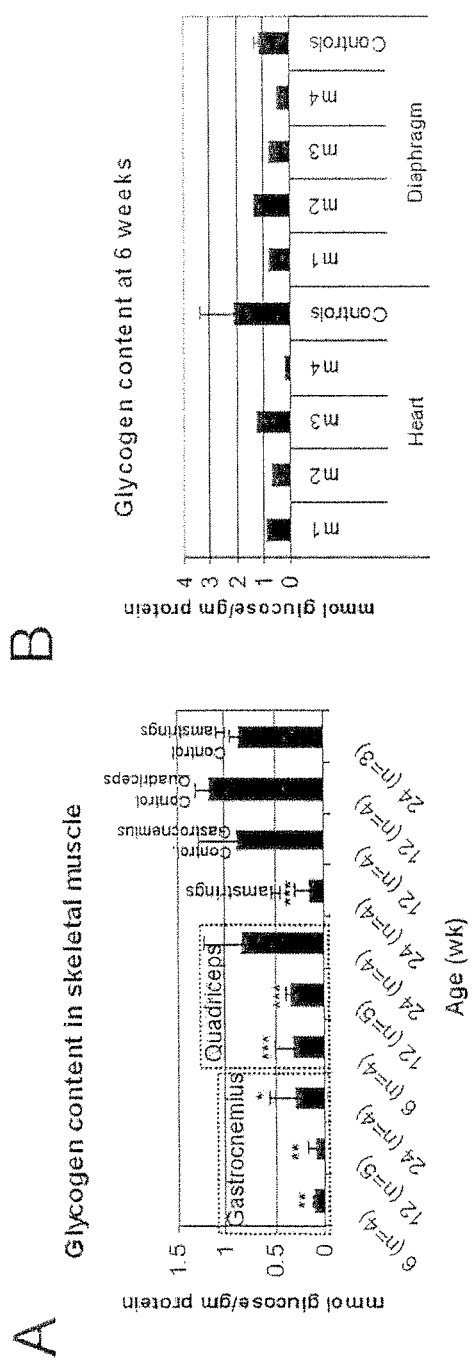
FIG. 4. The glycogen content for skeletal muscle and heart. (Panel A) Gastrocnemius and quadriceps at 6, 12, and 24 weeks following vector administration, and for hamstrings at 24 weeks, compared to the hGAA activity in gastrocnemius, quadriceps, and hamstrings for untreated, GAA-KO mice. The average and standard deviation are shown. The p value is indicated as follows: *<0.05, <0.01, and *<0.001. The number of mice (n) is shown for each time point. (Panel B) The glycogen content for heart and diaphragm, and for controls. Controls were untreated, GAA-KO mice (n=4). The average and standard deviation are shown for controls.

Reduced Glycogen Content in Skeletal Muscles of the Hind Limb Following Injection of the Gastrocnemius in Neonatal GAA-KO Mice The benefit of introduced hGAA in GSD II was shown by glycogen quantitation in skeletal muscle. Glycogen storage was reduced significantly for skeletal muscle groups at all time points except for the quadriceps at 24 weeks (FIG. 4 Panel A), when hGAA in the quadriceps was not as high as for other timepoints (FIG. 2 Panel A). Glycogen content was significantly reduced for the hamstrings, gastrocnemius, and quadriceps compared to untreated, GAA-KO mice (FIG. 4 Panel A). Glycogen content was reduced to 0.77+/−0.42 mmol glucose/gm protein in the heart of GAA-KO mice (n=4) 6 weeks after neonatal Ad-AAV vector administration, compared to 2.1+/1.3 mmol glucose/gm protein in untreated GAA-KO mice (n=3). Only 2 of 4 GAA-KO mice had detectable heart and diaphragm hGAA at 6 weeks by Western blot analysis (FIG. 1 Panel B; m1 and m4), and both the heart and diaphragm glycogen content was somewhat reduced in 1 of those mice (FIG. 4 Panel B; m4).

Figure 5:
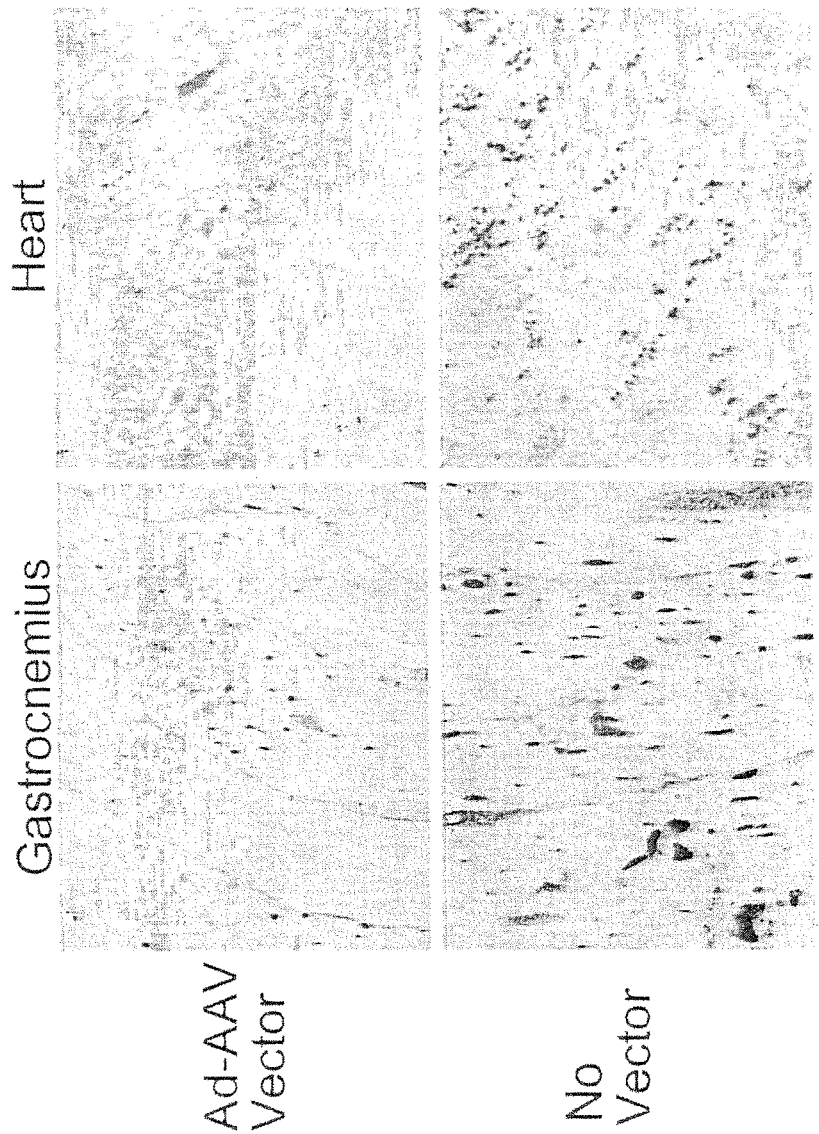
FIG. 5. Glycogen staining of skeletal muscle and heart. PAS staining showed glycogen accumulation in lysosomes, and pooling of glycogen outside lysosomes, that was corrected following Ad-AAV administration at the times indicated.

The correction of glycogen storage by introduced hGAA was evident by glycogen staining of gastrocnemius and heart. Periodic-acid Schiff (PAS) staining of gastrocnemius showed much less lysosomal accumulation of glycogen at 24 weeks following Ad-AAV vector administration compared to an untreated GAA-KO mouse (FIG. 5). In a GAA-KO mouse that had significant hGAA in heart at 6 weeks (FIG. 1 Panel B; m4), the glycogen accumulation in heart was less than for an untreated, GAA-KO mouse (FIG. 5). In aggregate, these data provide evidence for the continued benefit of hGAA introduced with a vector in muscle.

EXAMPLE 5

Construction of an AAV Vector Plasmid Encoding hGAA

The hGAA cDNA was subcloned with the CMV promoter from pcDNA3-hGAA (Van Hove et al. (1996). *Proc. Natl. Acad. Sci. USA* 93:65-70) into an AAV vector plasmid, as an NruI-EcoRV fragment, upstream of the human growth hormone intron 4 and polyadenylation sequence (Brinster et al. (1988). *Proc. Natl. Acad. Sci. USA* 85: 836-340). The resulting transcriptional unit was flanked by the AAV2 TR sequences in pAAV-ChGAAGH. A 530 bp deletion spanning the human growth hormone intron 4 was generated by EcoRV and partial PvuII digestion followed by blunting of ends with T4DNA polymerase and ligation with T4 DNA ligase to generate pAAV-ChGAAG(−). The hybrid CMV enhancer/chicken β-actin (CB) promoter was amplified by polymerase chain reaction from pTriEx1 (Novagen, Madison, Wis.) with primers that introduced unique upstream XbaI and downstream KpnI restriction sites, and the CB promoter was subcloned as a KpnI-XbaI fragment to replace the CMV promoter in pAAV-ChGAAG(−), to generate pAAV-CBhGAAG(−), in order to reduce the packaging size further, the plasmid pAAV-CBhGAAG(−) was linearized at a unique AflII site in the 3' untranslated sequence of the hGAA cDNA and partially digested with NspI to introduce a 411 bp deletion in the 3' untranslated sequence of the hGAA cDNA, followed by blunting of ends with T4 DNA polymerase and ligation with T4 DNA ligase to generate pAAV-CBGAApA. Finally, the vector sequences from pAAV-CBGAApA were isolated as a 4.4 kbp fragment from a partial BglII digest, and ligated with the calf intestinal alkaline phosphatase-dephosphorylated BglII site of pShuttle (He, T.-C., et al. (1998). *Proc. Natl. Acad. Sci. USA* 95:2509-2514).

EXAMPLE 6

Construction of a Hybrid [E1-, Polymerase-, Preterminal Protein-] Ad-AAV Vector Encoding hGAA Kanamycin-resistant shuttle plasmids were constructed to contain within the Ad E1 region the CB promoter+hGAA cDNA+polyA transgene cassette flanked by the AAV2 TR sequences. The shuttle plasmid was digested with PmeI, and electroporated into the BJ5183 recombinogenic strain of *E. Coli* with the pAd[E1-, polymerase-, preterminal protein-] plasmid (Hodges et al., (2000). *J. Gene Med.* 2:250-259). Recombinant kanamycin-resistant clones were screened by restriction enzyme digestion (BstXI) to confirm successful generation of the full-length recombinant Ad vector genomes. These clones were digested with PacI and transfected as previously described into the E1, and E2b expressing cell line, C-7 (Amalfitano et al. (1998), *J. Virol.* 72:926-933).

The vectors were amplified and confirmed to have the correct construction by restriction enzyme mapping of vector genomes, and subsequent functional assays in vitro and in vivo. Once isolated, the respective Ad vectors are serially propagated in increasing numbers of C-7 cells (Amalfitano et al. (1993), *J. Virol.* 72:925-933). Forty-eight hours after infection, infected cell pellets were harvested by low speed centrifugation, resuspended in 10 mM Tris-HCl pH 8.0, vector released from the cells by repeated freeze-thawing (×3) of the lysate, released by ultrasonification, and the supernatant containing vector was subjected to two rounds of equilibrium density CsCl centrifugation (Amalfitano et al. (1998). *J. Virol.* 72:926-933). Two virus bands were visible. The virus bands were then removed, dialyzed extensively against 10 mm Tris-HCl pH 8.0 (or PBS), sucrose added to 1%, and aliquots stored at −80° C. The number of vector particles was quantified based on the $OD_{260}$ of vector contained in dialysis buffer with sodium dodecyl sulfate [SDS] disruption, and by DNase I digestion, DNA extraction, and Southern blot analysis.

Hybrid Ad-AAV vector DNA analysis consisted of vector DNA isolation and restriction enzyme digestion followed by Southern blotting to verify the presence of intact AAV vector sequences within the lower band in the cesium chloride gradient, including restriction enzymes that demonstrated the presence of AAV terminal repeat sequences flanking the transgene (AhdI and BssHII) (Sun et al., (2003) *Mol Ther* 7:193-201).

EXAMPLE 7

Preparation of AAV Vectors

AAV vector stocks were prepared as described herein with modifications as described (Sun B D, Chen Y-T, Bird A, Xu F, Hou Y-X, Amalfitano A, and Koeberl D D. Packaging of an AAV vector encoding human acid α-glucosidase for gene therapy in glycogen storage disease type II with a modified hybrid adenovirus-adeno-associated virus vector. Mol Ther 7:467-477, 2003; Halbert C L, Alien J M, Miller A D. Adeno-associated virus type 6 (AAV) vectors mediate efficient transduction of airway epithelial cells in mouse lungs compared to that of AAV2 vectors. (Halbert et al., (2001) *J Virol* 75:6615-6624). Briefly, 293 cells were infected with the hybrid Ad-AAV vector (2000 DNase I-resistant vector particles/cell as quantitated by Southern blot analysis) containing the AAV vector sequences 15-30 minutes before transfection with an AAV packaging plasmid containing the AAV2 Rep and AAV2 or AAV6 (for AAV6 vector [Halbert et al. (2001) *J. Virol.* 75:6615-3624]). Cap genes were driven by heterologous promoters, which typically generate no detectable replication-competent AAV (rcAAV) (Allen et al. (2000) *Mol. Ther.* 1:88-95, Allen et al. (1997) *J. Virol.* 71:6816-6822). Cell lysate was harvested 48 hours following infection and freeze-thawed 3 times, isolated by iodixanol step gradient centrifugation before heparin affinity column purification (Zolotukhin et al. (1999) *Gene Ther.* 6:973-995; Halbert C L, Allen J M, Miller A D. Adeno-associated virus type 6 (AAV) vectors mediate efficient transduction of airway epithelial cells in mouse lungs compared to that of AAV2 vectors. *J Virol* 2001; 75:6615-6624.), and aliquots were stored at −80° C. The number of vector DNA containing-particles was determined by DNase I digestion, DNA extraction, and Southern blot analysis. Contaminating wt AAV particles were detected in recombinant AAV vector preparations by Southern blot analysis of extracted vector DNA, and by a sensitive PCR assay utilizing primers spanning the junction between the rep and cap genes. The level of rcAAV was less than 1 particle in $10^5$ AAV vector particles. All viral vector stocks were handled according to Biohazard Safety Level 2 guidelines published by the NIH.

EXAMPLE 8

In vivo Administration of AAV Vector Stocks

AAV vector was administered intramuscularly into the gastrocnemius muscle of 6 week-old GAA-KO mice (Raben et al. (1998) *J. Biol. Chem.* 273:19086-19092)/SCID mice. One hundred μl containing $1 \times 10^{11}$ DNase I-resistant AAV vector particles were injected per gastrocnemius. For portal vein injection, an AAV vector was administered via portal vein injection. At the respective time points post-injection, plasma or tissue samples were obtained and processed as described below. For intravenous administration, an AAV vector was administered via the retroorbital sinus. All animal procedures were done in accordance with Duke University Institutional Animal Care and Use Committee-approved guidelines.

EXAMPLE 9

Determination of hGAA Activity and Glycogen Content

Tissue hGAA activity was measured following removal of the tissue from control or treated mice, flash-freezing on dry ice, homogenization and sonication in distilled water, and pelleting of insoluble membranes/proteins by centrifugation. Untreated, affected controls were GAA-KO mice, 12 weeks old at the time of analysis except where noted otherwise. The protein concentrations of the clarified suspensions were quantified via the Bradford assay. hGAA activity in the muscle was determined as described (Kikuchi, T., et al. (1998) *J. Clin. Invest.* 101:827-833). Glycogen content of tissues was measured using the *Aspergillus niger* assay system, as described (Amalfitano et al. (1999) *Proc. Natl. Acad. Sci. USA* 968861-8866). A two-tailed homoscedastic Student's t-test was used to determine significant differences in hGAA levels and glycogen content between GAA-KO mice with or without administration of the vector encoding hGAA.

EXAMPLE 10

Western Blotting Analysis of hGAA

For direct detection of hGAA in tissues, samples (100 µg of protein) were electrophoresed overnight in a 6% polyacrylamide gel to separate proteins, and transferred to a nylon membrane. The blots were blocked with 5% nonfat milk solution, incubated with primary and secondary antibodies and visualized via the enhanced chemiluminescence (ECL) detection system (Amersham Pharmacia, Piscataway, N.J.).

EXAMPLE 11

Results with Abbreviated hGAA cDNA

High-level production of hGAA in muscle was shown with an AAV2/6 (AAV6) vector containing the shortened hGAA cDNA (FIG. 6). The hGAA level in skeletal muscle with the AAV6 vector is approximately 10-fold higher than the GAA level in normal mice. The hGAA and glycogen content was analyzed in GAA-knockout (GAA-KO)/SCID mice that were treated at 6 weeks of age, so these levels reflect the delivery of hGAA in adult animals. The analysis was done 6 weeks following intramuscular AAV6 injection, and demonstrated a trend toward long-term expression. In addition, glycogen content was significantly reduced ($p<0.002$), indicating a therapeutically-relevant effect from this level of hGAA, production in muscle at that time point. Furthermore, prolonged hGAA expression and complete reduction of glycogen content to normal was observed in the injected gastrocnemius muscle at 12 weeks after AAV6 vector administration (not shown).

These data indicate that intramuscular injection of AAV vector is efficacious in glycogen storage disease II.

Figure 7:
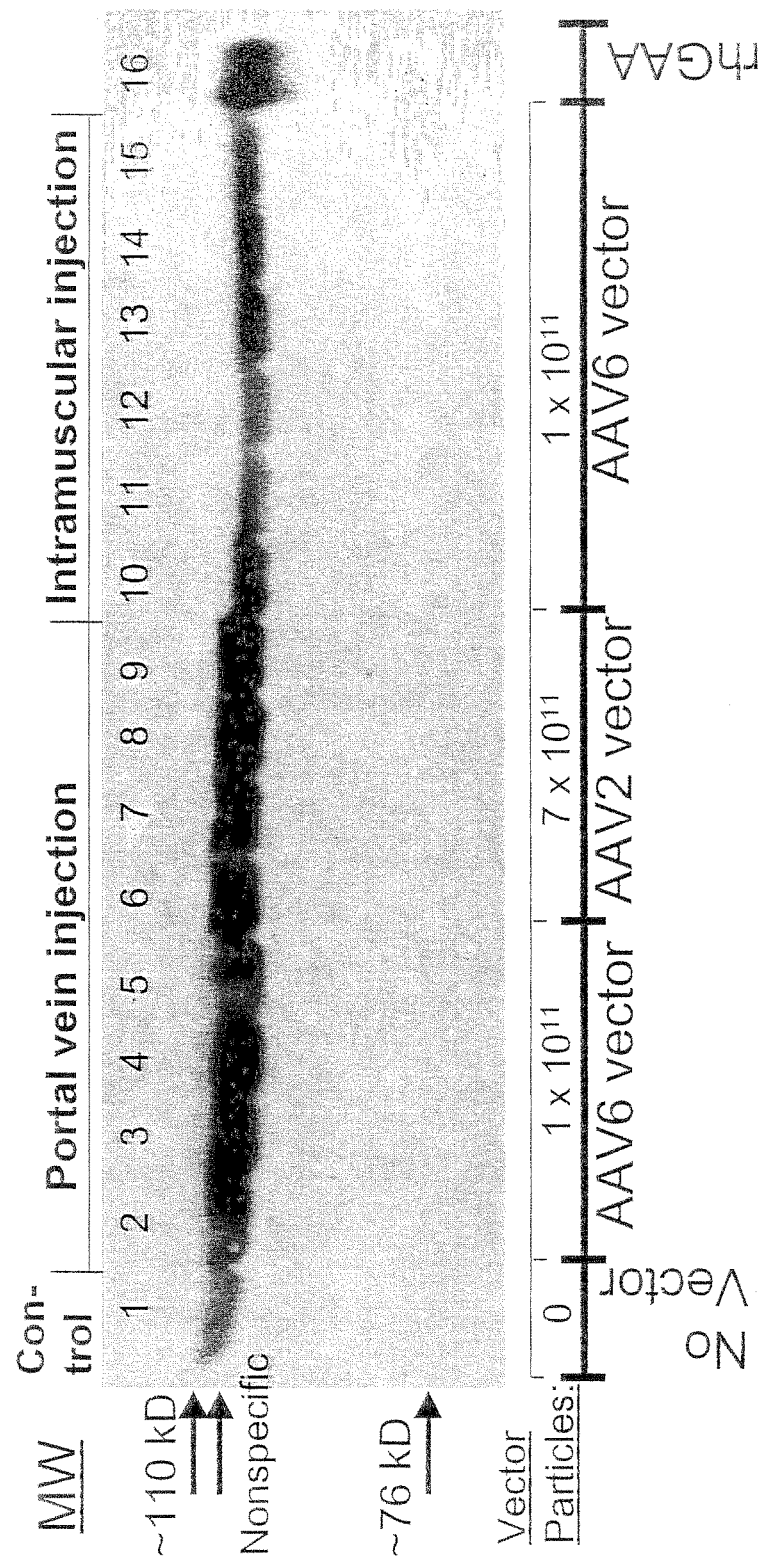
FIG. 7. Secretion of hGAA from liver into plasma in GAA-KO/SCID mice administered an AAV2/2 (AAV2) or AAV2/6 (AAV6) vector. Western blot analysis of plasma from GAA-KO/SCID mice following AAV vector administration, and from untreated GAA-KO/SCID mice (controls).

We have further shown secretion from liver with the AAV2/6 (AAV6) and AAV2/2 (AAV2) versions of the vector containing the shortened hGAA cDNA in GAA-KO/SCID mice following portal vein injection (FIG. 7). The abbreviated GAA vector was packaged within either an AAV2 or AAV6 capsid to generate two different vector stocks. Each stock was administered to a different mouse by portal vein injection. hGAA was detected in plasma from both mice by Western blot analysis. The data further demonstrate uptake of hGAA by skeletal muscle and heart with these vectors.

These results indicate that the liver can be used as a depot organ for hGAA production, with delivery to skeletal muscle and heart that results in a reduction in glycogen stores in these tissues due to uptake of secreted GAA.

EXAMPLE 12

Intramuscular versus Intraportal Delivery of AAV Vectors in GAA-KO Mice

An AAV2 vector packaged as AAV1 (AAV2/1) corrected glycogen storage when injected intramuscularly; however, the effect was observed only in the injected muscle (Fraites et al. (2002) *Mol. Ther.* 5:571-578). On the other hand, when we administered an AAV vector by portal vein injection in immunodeficient GAA-KO mice (GAA-KO/SCID mice), GAA was delivered to liver and other tissues (Sun et al. (2003) *Mol. Ther.* 2003; 7:467-477). Therefore, we investigated the difference in benefit between intramuscular and intraportal injection of the AAV vector, since the latter approach delivered GAA to multiple target tissues including skeletal muscles, the diaphragm and the heart.

We chose to evaluate the benefit of an AAV vector encoding the shortened GAA targeted to skeletal muscle or to liver in the GAA-KO/SCID mouse model. We administered an AAV vector encoding the shortened GAA by intramuscular or portal vein injection in GAA-KO/SCID mice, and analyzed GAA activity and glycogen content in tissues. The AAV2-derived vector was packaged as AAV2 (AAV2/2) or AAV6 (AAV2/6) for portal vein injections. Based on homology between the capsid proteins of AAV6 and AAV1, it was deemed likely that AAV2/6 would transduce myofibers more efficiently than AAV2/2 (Chao et al. (2000) *Mol. Ther.* 2:619-623; Rabinowitz et al. (2002) *J. Virol.* 76:791-801; Rutledge et al. (1998) *J. Virol.* 72:309-319). The AAV2/6 vector was injected intramuscularly. Glycogen content and GAA activity were analyzed in tissues at 6, 12, and 24 weeks after vector injection.

Results.

Figure 10:
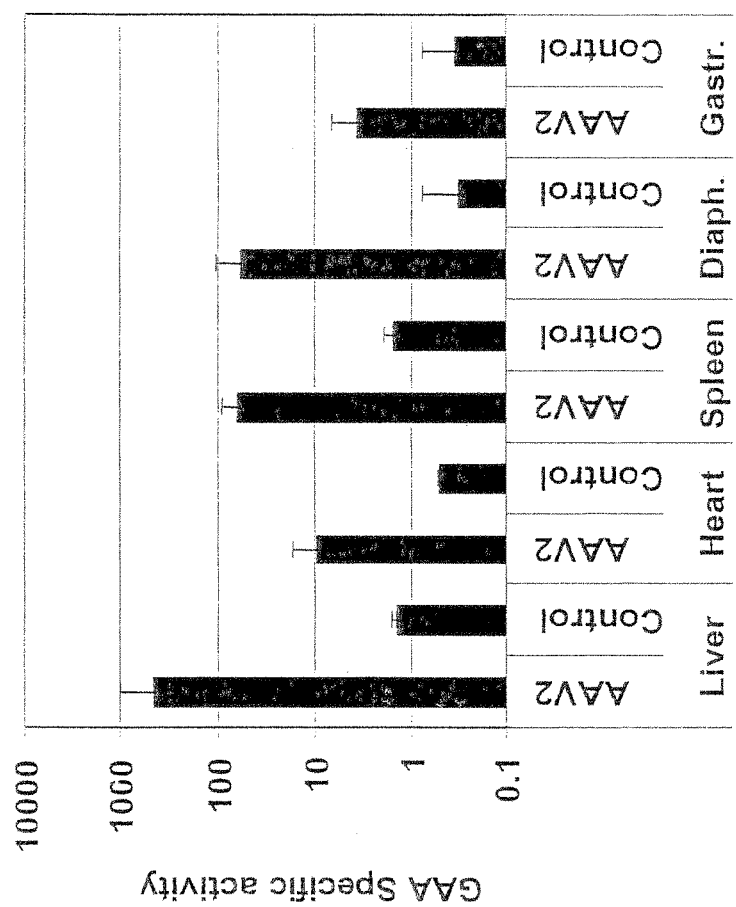
FIG. 10. GAA activity in liver and other tissues following portal vein injection of an AAV2/2 vector. GAA-KO/SCID mice received the vector packaged as AAV2 (AAV2/2) at 3 months of age (n=3), and were analyzed 12 weeks after injection. Controls were 3 month-old, untreated GAA-KO/SCID mice (n=3).
Figure 11:
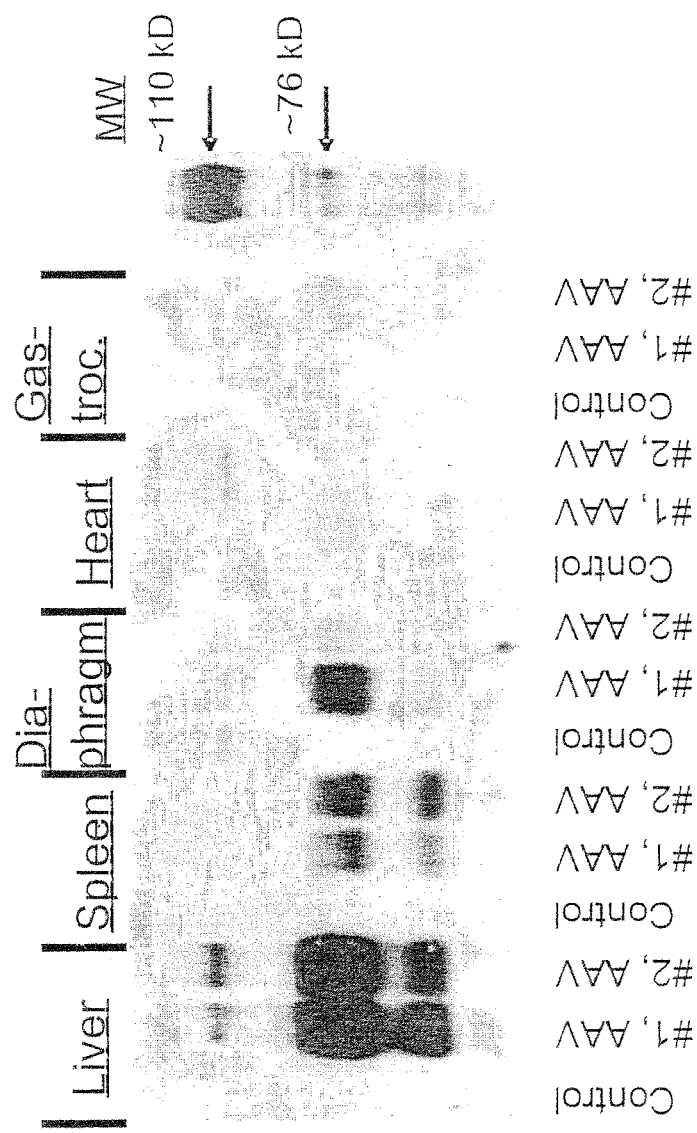
FIG. 11. Human GAA in liver and other tissues following portal vein injection of AAV vectors in GAA-KO/SCID mice. Western blot analysis of plasma from GAA-KO/SCID mice at the indicated times following AAV vector administration, and from untreated GAA-KO/SCID mice (controls). Recombinant hGAA (rhGAA) is shown as a standard.

Following portal vein injection of an AAV2/2 vector, secreted GAA was detectable by Western blot analysis of plasma starting at 2 weeks and persisted for 12 weeks (Data not shown). GAA activity was highly elevated in multiple tissues compared to baseline levels in untreated GAA-KO/SCID mice, and approximately 10-fold higher than wild-type levels in the liver at 12 weeks following vector administration (FIG. 10). Human GAA was detected by Western blot analysis of multiple tissues, including the target tissues of heart and diaphragm (FIG. 11). Enzyme analysis revealed that GAA activity was concordantly elevated in these tissues (FIG. 10). These results demonstrated the secretion and uptake of GAA following portal vein injection of the AAV vector, consistent with the model of the liver as a depot organ for GAA production in GAA-deficient states as established with an Ad vector.

Figure 12:
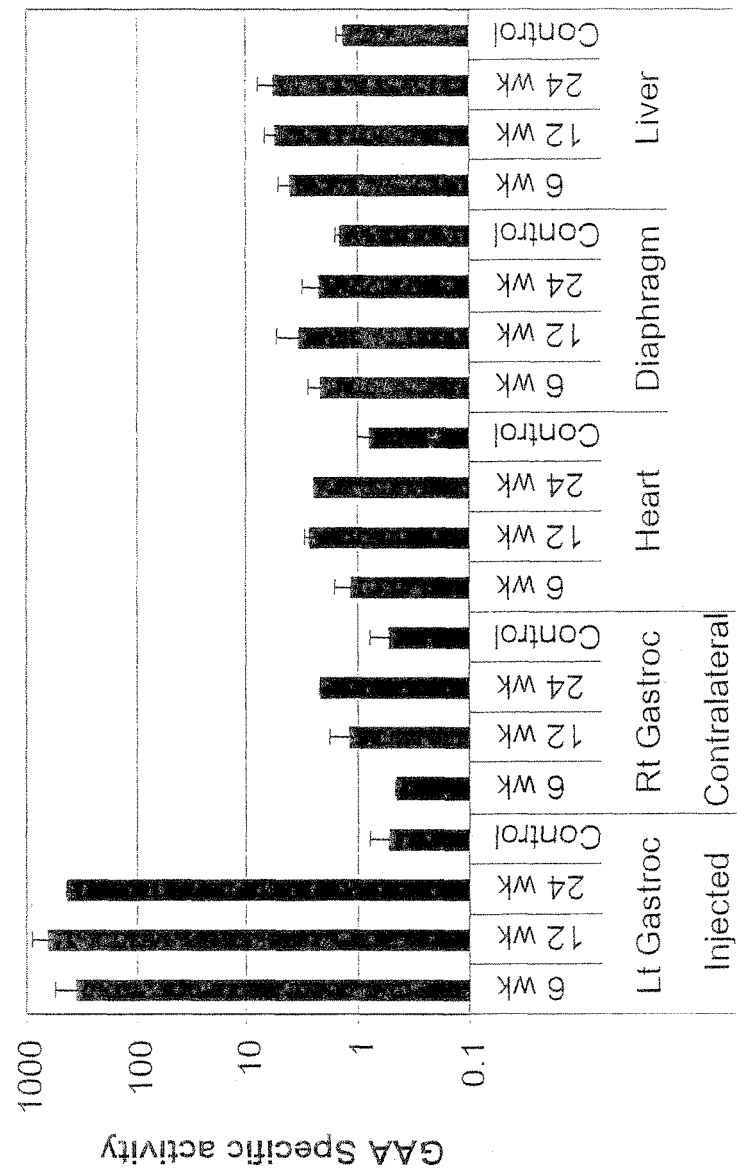
FIG. 12. GAA activity in gastrocnemius muscles (injected and uninjected) and other tissues following intramuscular injection of an AAV2/6 vector. GAA-KO/SCID mice received the vector packaged as AAV 6 (AAV2/6) at 6 weeks of age (n=8), and were analyzed at 6, 12 and 24 weeks after injection. Controls were 3 month-old, untreated GAA-KO/SCID mice (n=3).
Figure 13:
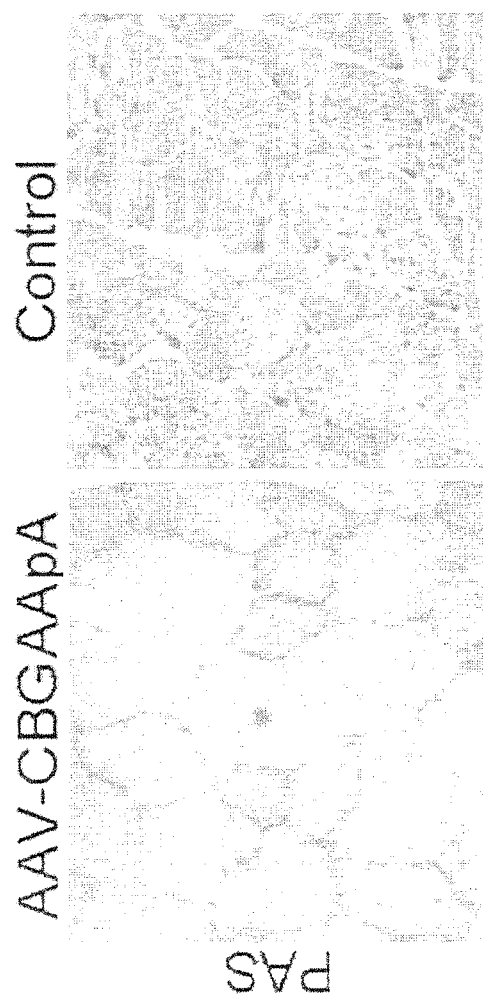
FIG. 13. Glycogen staining of skeletal muscle in GAA-KO/SCID mice. PAS staining showed glycogen accumulation in lysosomes, and pooling of glycogen outside lysosomes that was corrected following AAV2/6 administration.

Following intramuscular injection with the AAV2/6 vector, GAA activity in the gastrocnemius muscle exceeded normal levels by approximately 20-fold at 6, 12 and 24 weeks following vector administration (FIG. 12). In these mice the glycogen content in the injected muscle diminished to near-normal levels for up to 24 weeks following vector administration, and decreased glycogen accumulation as evidenced by decreased staining for glycogen (FIG. 13). Despite the achievement of high-level GAA production in skeletal muscle, the GAA activity in other tissues was not markedly increased (FIG. 12).

EXAMPLE 13 hGAA AAV Vectors with Altered Leader Signal Peptides

The peptide leader sequence (SEQ ID NO: 4, corresponding to amino acids 1-27, SEQ ID NO: 2) of hGAA was replaced with the synthetic peptide leader sequence SP38 (Barash et al., (2002) *Biochem. Biophys. Res. Comm.* 294: 835-42), as well as peptide leader sequences from erythropoietin, albumin, alpha-1-antitrypsin and factor IX. The amino acid sequences of these leader peptides are shown in Table 2.

TABLE 2

Amino acid sequences for leader peptides

| Leader sequence | Peptide sequence |
|---|---|
| hGAA | MGVRHPPCSHRLLAVCALVSLATAALL (SEQ ID NO: 4) |
| SP38 | MWWRLWWLLLLLLLLWPMVWA (SEQ ID NO: 5) |
| Human erythropoietin | MGVHECPAWLWLLLSLLSLPLGLPVLG (SEQ ID NO: 6) |
| Human albumin | MKWVTFISLLFLFSSAYS (SEQ ID NO: 7) |
| Human alpha-1-antityrpsin | MPSSVSWGILLLAGLCCLVPVSLA (SEQ ID NO: 8) |
| Human coagulation factor IX | MQRVNMIMAESPGLITCLLGYLLSAECT VFLDHENANKILNRPKR (SEQ ID NO: 9) |

Plasmid vectors that express hGAA in which the wild-type hGAA peptide leader sequence (SEQ ID NO: 4) is replaced with the different leader peptides listed in Table 2 were constructed using the plasmid AVCBhGAAG-delta as described briefly below. The resulting constructs encode a GAA peptide in which one of the peptides of SEQ ID NOS: 5-9 replaces the first 27 amino acids of SEQ ID NO: 1.

AVCBSP38GAAG-delta preparation strategy. A 0.37 kb PCR product from AVCBhGAAG-delta was amplified using the primers 5'-GCT GCA AAGCTT ggg cac atc cta ctc cat-3' (SEQ ID NO: 10) and 5'-cct gca gcc cct gct ttg cag gga tgt agc-3 (SEQ ID NO: 11). The resulting PCR product comprises nucleotide sequences that code for the region of the hGAA protein immediately downstream from the native hGAA, signal peptide (nucleotides 523-796, SEQ ID NO: 1) and adds a HindIII restriction site at the signal peptide cleavage site. This PCP product was digested with HindIII and SacII and gel-purified to produce DNA fragment 1.

A second DNA fragment coding for the SP38 leader sequence, KpnI-SP38-HindIII, 5'-AGC TGC TGA GGTACC TCA GCC ACC atg tgg tgg cgc ctg tgg tgg ctg ctg ctg ctg ctg ctg tgg ccc atg gtg tgg gcc AAGCTT CGA TGC TAC GTC-3', SEQ ID NO: 12, was hybridized with a reverse primer, 5'-GAC GTA GCA TCG AAG CTT-3', SEQ ID NO: 13. The resulting hybrid was extended Klenow DNA polymerase in the presence of dNTPs to form a double-stranded DNA fragment. The resulting DNA fragment contains a KpnI site near the 5' end followed by an optimal Kozak sequence (GCCACC) and the SP38 leader peptide coding sequence, followed with a HindIII site at the 3' end of the SP38 sequence. This DNA was digested with KpnI and HindIII and gel-purified to produce DNA fragment II.

DNA fragments I and II described above were then ligated into AVCBhGAAG-delta plasmid DNA digested with KpnI and SacII. The resulting ligation mixture was used to transform STBL2 cells (Gibco-BRL), and transformants containing AVCBSP38GAAG-delta were selected in the presence of antibiotics and structure confirmed by gel electrophoresis. The resulting construct codes for a GAA peptide in which the hGAA leader sequence (SEQ ID NO: 4) has been replaced with the SP38 leader sequence (SEQ ID NO: 5).

AVCBSP-hEpoGAAG-delta preparation strategy. The plasmid AVCBSP-hEpoGAAG-delta was prepared in the same manner as AVCBSP38GAAG-delta, wherein fragment II was replaced with the KpnI-HindIII digestion product of the double-stranded DNA fragment with sequence 5'-AGC TGC TGA GGTACC TCA GCC ACC atggggggtg cacgaatgtc ctgcctggct gtggcttctc ctgtccctgc tgtcgctccc tctgggcctc ccagtcctgg gc AAGCTT CGA TGC TAC GTC-3 (SEQ ID NO: 14). The resulting construct codes for a GAA peptide in which the hGAA leader sequence (SEQ ID NO: 4) has been replaced with the hEPO leader sequence (SEQ ID NO: 6).

AVCBSPantitrypsinGAAG-delta preparation strategy. The plasmid AVCBSPantitrypsinGAAG-delta was prepared in the same manner as AVCBSP38GAAG-delta, using the KpnI-HindIII digestion product of the double-stranded DNA fragment with sequence 5'-C TGA GGTACC T GCC ACC-at gccgtcttct gtctcgtggg gcatcctcct gctggcaggc ctgtgctgcc tggtccctgt ctccctggct-AAGCTT CGA T-3' (SEQ ID NO: 15) in lieu of fragment II. The resulting construct codes for a GAA peptide in which the hGAA leader sequence (SEQ ID NO: 4) has been replaced with the human alpha-1-antityrpsin leader sequence (SEQ ID NO: 7).

AVCBSPALBGAAG-delta preparation strategy. AVCBSPALBGAAG-delta was prepared in the same manner as AVCBSP38GAAG-delta, using the KpnI-HindIII digestion product of the double-stranded DNA fragment with sequence 5'-C TGA GGTACC T GCC ACC-a tgaagtgggt aacctttatt tcccttcttt ttctcttttag ctcgacttat tcc-AAGCTT CGA T-3' (SEQ ID NO: 16) in lieu of fragment II. The resulting construct codes for a GAA peptide in which the hGAA leader sequence (SEQ ID NO: 4) has been replaced with the human albumin leader sequence (SEQ ID NO: 8).

AVCBSPFIXGAAG-delta preparation strategy. Lastly, AVCBSPFIXGAAG-delta was prepared in the same manner as AVCBSP38GAAG-delta, using the KpnI-HindIII digestion product of the double-stranded DNA fragment with sequence 5'-C TGA GGTACC T GCC ACC atgcagcgcg tgaacatgat catggca-3' (SEQ ID NO: 17) in lieu of fragment II. The resulting construct codes for a GAA peptide in which the hGAA leader sequence (SEQ ID NO: 4) has been replaced with the human factor IX leader sequence (SEQ ID NO: 9).

The resulting plasmids were used to examine the effect of different leader sequences on the localization of hGAA in cells transfected with these plasmids.

EXAMPLE 14

Figure 14:
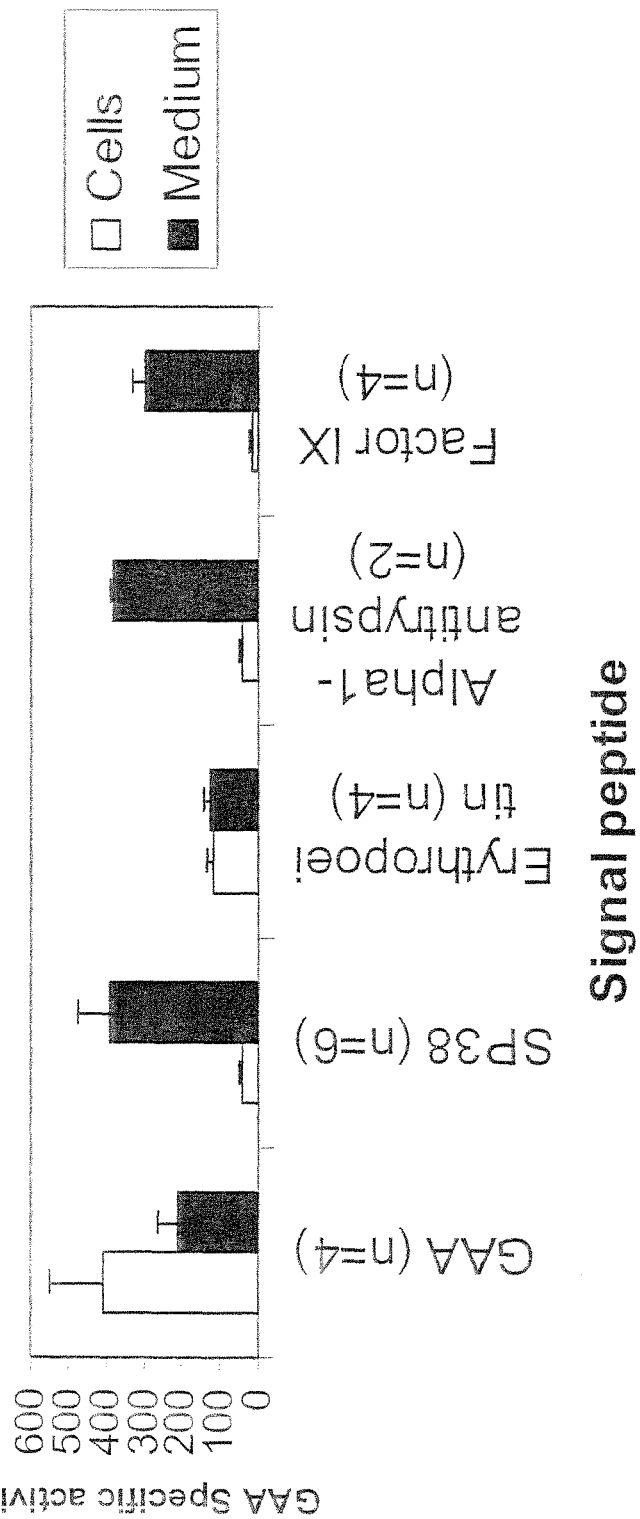
FIG. 14. Localization (cellular vs. secreted) of GAA with various leader sequences expressed in transfected 293 cells.

Relative Secretion of hGAA with Altered Leader Sequences in 293 Cells 293 cells were transfected with AAV vector plasmids described in Example 13 and were collected 40 hours post-transfection. Total hGAA activity was assayed both in the cells and in the medium. These results are depicted in FIG. 14 and the relative hGAA secretion is summarized in Table 3.

TABLE 3 hGAA secretion with different leader sequences

| Leader sequence | Proportion hGAA secreted (hGAA medium/hGAA cells) | % Total hGAA secreted | Increased hGAA secretion (fold) |
|---|---|---|---|
| HGAA | 0.53 | 34 | N/A |
| SP38.1 | 9.7 | 91 | 18 |
| Epo | 1.1 | 53 | 2.1 |
| α-1-antitrypsin | 8.5 | 90 | 16 |
| Factor IX | 14 | 93 | 26 |

Figure 15:
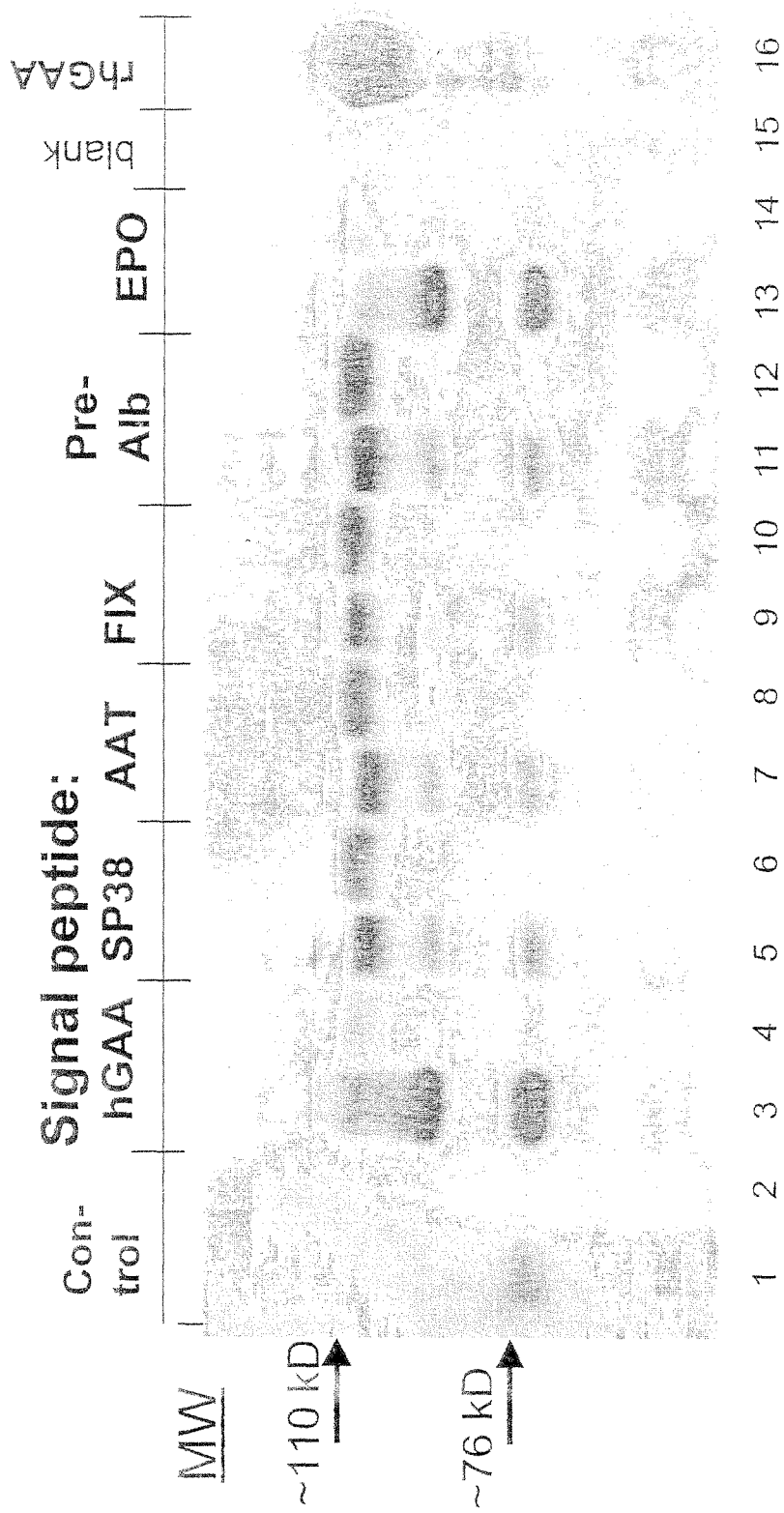
FIG. 15. Western blot analysis of GAA with various leader sequences. GAA expressed in transfected 293 cells with the constructs containing hGAA linked to the indicated signal peptides. For transfected 293 cells, in lanes 3-14, the first (odd-numbered) of 2 lanes for each construct represents the cell lysate and the second lane (even-numbered) is the medium. The control represents untransfected 293 cells, showing endogenous, processed hGAA. Recombinant human GAA (rhGAA) is shown as a standard.
Figure 16:
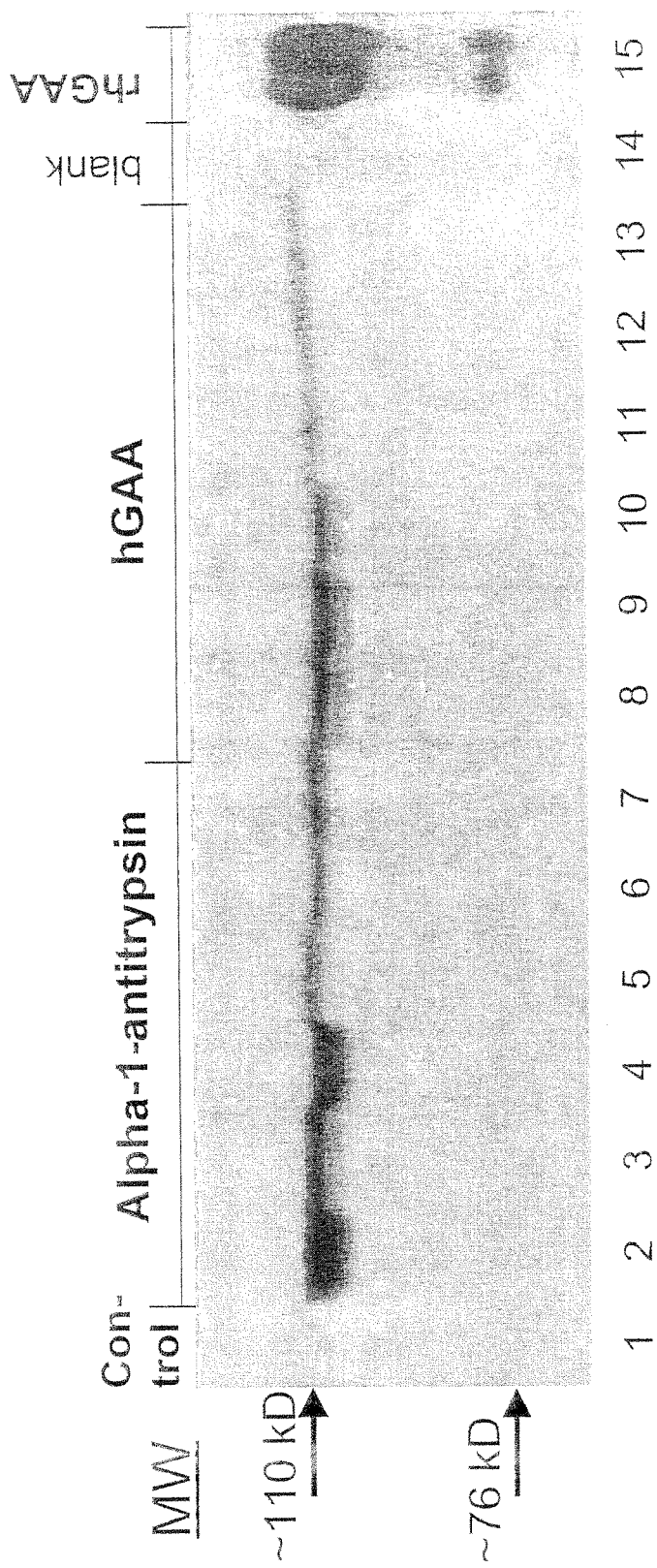
FIG. 16. Western blot analysis of plasma from GAA-KO/SCID mice at 2 weeks following vector administration, and from untreated GAA-KO/SCID mice (controls). Three-month-old GAA-KO/SCID mice received an AAV vector encoding the chimeric α-1-antitrypsin signal peptide linked to the hGAA cDNA (Alpha-1-antitrypsin, lanes 2-7), or an AAV vector encoding hGAA with its endogenous signal peptide (hGAA, lanes 8-13). Each lane represents an individual mouse. Lanes 5-7 and 11-13 were female mice. Recombinant human GAA (rhGAA) is shown as a standard.

Western blot analysis of cellular and secreted hGAA in 293 cells transfected with the AAV vector plasmids described in Example 13 demonstrated normal migration, consistent with unaltered glycosylation and processing of chimeric hGAA linked to alternative signal peptides (FIG. 15). This data supported the normal glycosylation of hGAA, despite the increased secretion and presumably shortened residence in the Golgi (Wisselaar et al., (1993) *J. Biol. Chem.* 268 (3): 2223-31). For further evidence of the normal glycosylation of hGAA produced with these constructs, we injected mice with the AAV2/8 vector encoding the chimeric α-1-antitrypsin signal peptide linked to the hGAA cDNA (minus the 27 amino acid GAA signal peptide), and hGAA was detected corresponding to the ~110 kD hGAA precursor (FIG. 16). The hGAA level was lower for female mice (lanes 5-7 and 11-13), as expected given lower transduction with AAV2/8 vectors in female mice. Significantly, hGAA secretion was higher for the vector containing the chimeric α-1-antitrypsin signal peptide (lanes 2-7), than for the vector containing the hGAA signal peptide (lanes 8-13).

Figure 17:
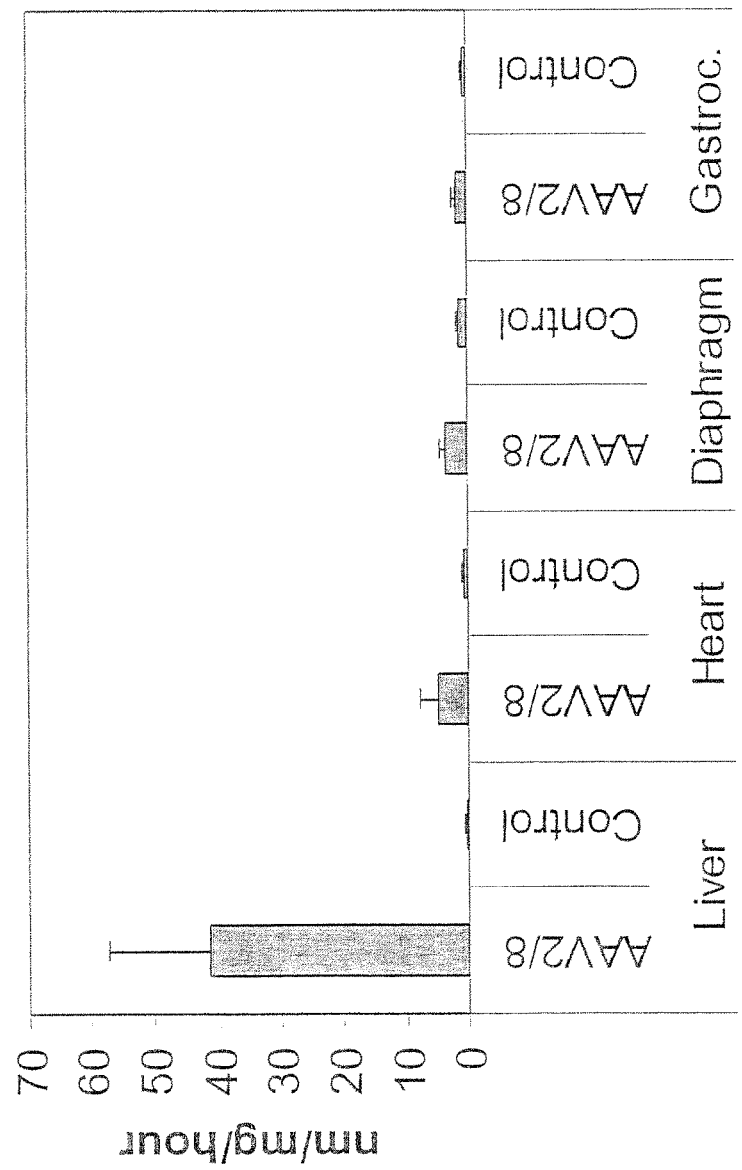
FIG. 17. GAA activity in liver and other tissues at 2 weeks following intravenous injection of an AAV2/8 vector encoding hGAA linked to the alpha-1-antitrypsin leader sequence. Male 3 month-old GAA-KO/SCID mice (n=3) received an AAV vector encoding the chimeric alpha-1-antitrypsin signal peptide linked to the hGAA cDNA (minus the 27 amino acid GAA signal peptide). Controls were untreated GAA-KO/SCID mice (n=3).

Tissue GAA activity was increased in tissues for the 3 male GAA-KO/SCID mice that received the AAV vector encoding the alpha-1-antitrypsin signal peptide linked to hGAA (corresponding to lanes 2-5 in FIG. 16). Significantly, liver GAA activity remained at near normal levels, despite increased GAA activity in tissues compared to controls (FIG. 17). These results were obtained at only 2 weeks following vector administration, as opposed to the later 6-week time point used in the other experiments, and indicated early uptake of secreted GAA in the target tissues of heart, diaphragm, and at lower levels, skeletal muscle. GAA uptake in target tissues is expected to increase after the 2-week time point, based on previous results. Finally, a Western blot of the target tissues showed appropriate processing of hGAA to ~76 kD and ~67 kD (data not shown). These data support the hypothesis that chimeric hGAA linked to alternative signal peptides will be appropriately secreted, processed and targeted to lysosomes in target tissues, despite the maintenance of normal GAA levels in liver. This novel development will reduce any potential toxicity for overexpression of hGAA in the depot organ, the liver, in contrast to all previous approaches to liver-targeted gene therapy in Pompe disease that produced extreme supraphysiological levels of GAA in the liver

EXAMPLE 15

Figure 18:
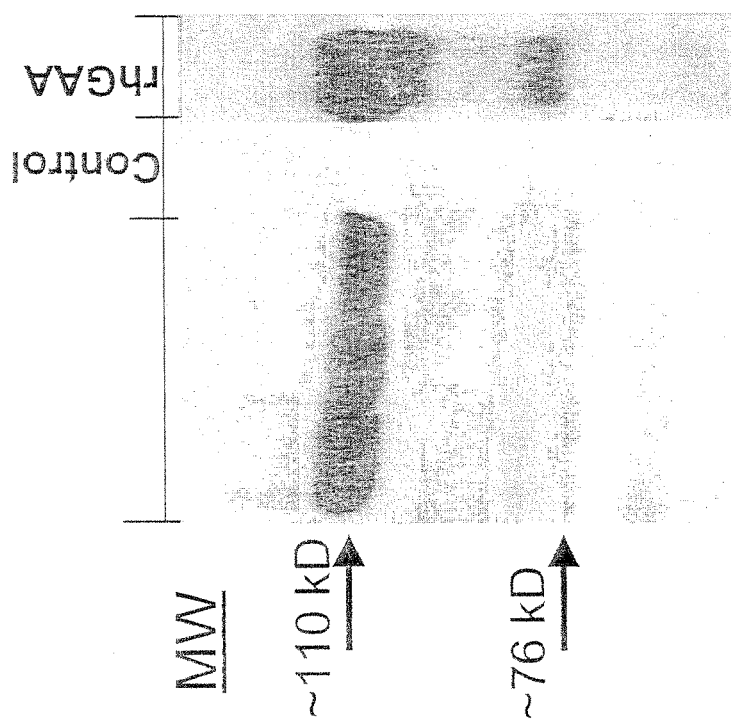
FIG. 18. Human GAA in liver and other tissues following intravenous injection of an AAV vector containing a liver-specific promoter to drive GAA expression in immunocompetent GAA-KO mice. Western blot analysis of plasma from GAA-KO mice at 3 weeks following AAV vector administration, and from untreated GAA-KO mice (controls). Recombinant human rhGAA (rhGAA) is shown as a standard.

Expression of hGAA with a Liver-specific Promoter in Immunocompetent GAA-KO Mice An AAV2/8 vector encoding hGAA driven by a liver-specific promoter (Wang L et al., (1999) *Proc Nat Acad Sci USA* 96:3906-10) was administered intravenously in GAA-KO mice. Contrary to previous experiments, where hGAA, was eliminated in plasma by anti-GAA antibodies in immunocompetent GAA-KO mice, hGAA persisted in plasma as detected by Western blot analysis (FIG. 18). Therefore, the limitation of GAA expression to the liver eliminated the antibody response and allowed persistent GAA secretion with implications for gene therapy in Pompe disease.

The foregoing is illustrative of the present invention, and is not to be construed as limiting thereof. The invention is defined by the following claims, with equivalents of the claims to be included therein.

That which is claimed is:

1. An adeno-associated virus (AAV) vector comprising a nucleic acid encoding a chimeric polypeptide comprising a secretory signal sequence of α1-antitrypsin having the sequence of SEQ ID NO:8 operably linked to a lysosomal acid α-glucosidase (GAA) polypeptide, wherein said secretory signal sequence replaces the first 27 amino acids of SEQ ID NO:2 of the native lysosomal GAA polypeptide.

2. The vector of claim 1 wherein said nucleic acid is operatively linked to a transcriptional control element operable in liver cells.

3. A pharmaceutical formulation comprising the vector of claim 1 in a pharmaceutically acceptable carrier.

4. An isolated cell comprising the vector of claim 1.

5. An in-vitro method of delivering a nucleic acid encoding a lysosomal GAA polypeptide to a cell, comprising contacting a cell in-vitro with the vector according to claim 1 under conditions sufficient for the vector to be introduced into the cell and for the nucleic acid to be expressed to produce the chimeric polypeptide comprising the secretory signal sequence of α1-antitrypsin having the sequence of SEQ ID NO:8 operably linked to the lysosomal GAA polypeptide wherein said secretory signal sequence replaces the first 27 amino acids of SEQ ID NO:2 of the native lysosomal GAA polypeptide.

6. A method of producing a lysosomal a-glucosidase (GAA) polypeptide in a cultured cell, comprising:
contacting a cultured cell with the vector according to claim 1 under conditions sufficient for the vector to be introduced into the cultured cell and for the nucleic acid to be expressed to produce the chimeric polypeptide comprising the secretory signal sequence of α1-antitrypsin having the sequence of SEQ ID NO:8 operably linked to the GAA polypeptide wherein said secretory signal sequence replaces the first 27 amino acids of SEQ ID NO:2 of the native lysosomal GAA polypeptide and the GAA polypeptide is secreted from the cultured, and collecting the GAA polypeptide secreted onto the cell culture medium.

7. A pharmaceutical formulation comprising the vector of claim 2 in a pharmaceutically acceptable carrier.

8. An isolated cell comprising the vector of claim 2.

9. An in-vitro method of delivering a nucleic acid encoding a lysosomal GAA polypeptide to a cell, comprising contacting a cell in-vitro with the vector according to claim 2 under conditions sufficient for the vector to be introduced into the cell and for the nucleic acid to be expressed to produce the chimeric polypeptide comprising the secretory signal sequence of α1-antitrypsin having the sequence of SEQ ID NO:8 operably linked to the lysosomal GAA polypeptide wherein said secretory signal sequence replaces the first 27 amino acids of SEQ ID NO:2 of the native lysosomal GAA polypeptide.

10. A method of producing a lysosomal α-glucosidase (GAA) polypeptide in a cultured cell, comprising: contacting a cultured cell with the vector according to claim 2 under conditions sufficient for the vector to be introduced into the cultured cell and for the nucleic acid to be expressed to produce the chimeric polypeptide comprising the secretory signal sequence of α1-antitrypsin having the sequence of SEQ ID NO:8 operably linked to the GAA polypeptide wherein said secretory signal sequence replaces the first 27 amino acids of SEQ ID NO:2 of the native lysosomal GAA polypeptide and the GAA polypeptide is secreted from the cultured, and collecting the GAA polypeptide secreted onto the cell culture medium.

11. The vector of claim 1 wherein GAA secretion is increased relative to the native lysosomal GAA polypeptide of SEQ ID NO:2.

* * * * *